(12) United States Patent
Hunter et al.

(10) Patent No.: US 8,877,636 B1
(45) Date of Patent: Nov. 4, 2014

(54) PROCESSING OF NANOSTRUCTURED DEVICES USING MICROFABRICATION TECHNIQUES

(75) Inventors: Gary W Hunter, Oberlin, OH (US); Jennifer C Xu, Olmsted Township, OH (US); Laura J Evans, Fairview Park, OH (US); Michael H Kulis, Shaker Heights, OH (US); Gordon M Berger, Akron, OH (US); Randall L Vander Wal, State College, PA (US)

(73) Assignee: The United States of America as Represented by the Adminstrator of National Aeronautics and Space Administration, Washington, DC (US)

( * ) Notice: Subject to any disclaimer, the term of this patent is extended or adjusted under 35 U.S.C. 154(b) by 765 days.

(21) Appl. No.: 13/036,887

(22) Filed: Feb. 28, 2011

Related U.S. Application Data

(60) Provisional application No. 61/308,438, filed on Feb. 26, 2010.

(51) Int. Cl.
    *H01L 23/495* (2006.01)

(52) U.S. Cl.
    USPC ............ 438/666; 438/665; 977/778; 977/785

(58) Field of Classification Search
    CPC .......................... H01L 21/288; H01L 21/2885
    USPC .......... 438/665, 666; 977/742, 778, 785, 936, 977/953, 957
    See application file for complete search history.

(56) References Cited

U.S. PATENT DOCUMENTS 8,211,765 B2 * 7/2012 Somu et al. .................... 438/257
2009/0294966 A1 * 12/2009 Liu et al. ........................ 257/746

* cited by examiner

*Primary Examiner* — Matthew E Warren
(74) *Attorney, Agent, or Firm* — Robert H. Earp, III

(57) ABSTRACT

Systems and methods that incorporate nanostructures into microdevices are discussed herein. These systems and methods can allow for standard microfabrication techniques to be extended to the field of nanotechnology. Sensors incorporating nanostructures can be fabricated as described herein, and can be used to reliably detect a range of gases with high response.

7 Claims, 36 Drawing Sheets

702

704

PROCESSING OF NANOSTRUCTURED DEVICES USING MICROFABRICATION TECHNIQUES

CROSS-REFERENCE TO RELATED APPLICATIONS

This application claims the benefit of U.S. Provisional Patent application Ser. No. 61/308,438 entitled "SYNTHESIS METHODS, MICROSCOPY CHARACTERIZATION AND DEVICE INTEGRATION OF NANOSCALE METAL OXIDE SEMICONDUCTORS FOR GAS SENSING IN AEROSPACE APPLICATIONS" and filed Feb. 26, 2010. The entirety of the above-noted application is incorporated by reference herein.

ORIGIN OF THE INVENTION

The invention described herein was made by employees of the United States Government and may be manufactured and used by or for the Government for Government purposes without the payment of any royalties thereon or therefor.

BACKGROUND

Nanotechnology is a field of study related to materials on an atomic or molecular scale. Typically size ranges involved are on the scale of from approximately 1 nanometer (1 nm) to distances on the order of 400 nm or less. Nanotechnology has potential applications in a wide range of areas, including medicine, electronics, biomaterials, and energy production.

One area of potential application for nanotechnology is in connection with chemical sensors. Metal oxide semiconductors (MOSs) (such as semiconducting tin oxide) have been used as chemical sensors for a number of years and have been shown to respond to relevant chemical species such as oxygen ($O_2$), carbon monoxide (CO), ethanol ($C_2H_5OH$), mono-nitrogen oxides ($NO_x$), $C_3H_6$, and $H_2$. Applications of chemical sensors include environmental monitoring, automotive applications, fire detection, and aerospace vehicles. High surface area and controlled structure are the aspects particularly relevant to sensors. Surface area is critical to gas adsorption. Correspondingly, high surface area translates into high sensitivity because the depletion layer becomes a significant fraction of the particle with decreasing particle size. Controlled structure provides the reactive sites for adsorption and their modulation of the overall conductance. Relative to micronsized grains, powders, layers, or films, nanostructures can offer 10 to 100-fold increases in each parameter. Additionally, nanostructures are more stable and less likely to sinter, thus they can yield a more stable sensor.

Moreover, nanostructures often possess unusual reactivities due to size and surface structure, reflecting defects, interstitial atoms, and incomplete bonding. Such activity can further enhance sensitivity and lower temperature operation. Operation at lower temperature can save power, and also extend operating lifetime and maintain reproducibility by preventing grain growth by sintering. Finally, lower temperature combined with structure control can advantageously yield selectivity.

Therefore, the use of nanostructures (e.g., nanotubes or nanorods) can decrease particle growth while, given the increased number of chemically sensitive particle boundaries, improving sensor sensitivity, stability, and response time. Moreover, carrier depletion (or replenishment) throughout the "bulk" nanostructure can expand the sensor dynamic range by the virtue of adsorbates leading to full charge depletion (or replenishment) with corresponding infinite or near-zero resistance, respectively. Thus, the potential advantages of nanostructures for sensor applications are clear.

However, despite the apparent advantages of nanostructures in a wide variety of applications, including sensor applications, significant challenges remain to widespread application. When creating sensor structures using nanostructures, one recognized challenge is integration of the nanostructures in a time efficient, cost effective manner. When using nanostructures as the sensing device, no matter how well the material performs as a sensor, if the ability to implement it into a sensor structure is limited, the sensing applicability will be limited as well.

Concurrent control of micro- and nanotechnology is necessary in order to achieve reliable interfaces with nanostructures. Currently nanostructures (e.g., carbon nanotubes) are often deposited onto materials primarily by adding them to a suspension, then applying the suspension in a thin film. The resulting sensor structure is random and uncontrolled, resembling straw dropped on the floor rather than a reproducibly processed material. The contacts to the sensing nanostructure are poorly defined and not reproducible.

Different approaches have been developed in an attempt to address these issues. One approach has included attempting to align nanostructures with atomic force microscopes or laser tweezers. However, this is a labor intensive approach and cannot be used for mass fabrication. Other work has involved using hydrodynamics or other methods such as traditional dielectrophoresis to align nanostructures on an existing microplatform. These techniques are performed separate from the standard microfabrication processing, and also present significant challenges to mass fabrication.

In still other cases, through random alignment, nanostructures have been buried under metallic contacts on microstructures. More recent work has involved E-Beam processing with nanodimensioned linewidth. Again, the use of these techniques are outside of standard microfabrication techniques. Other techniques, including use of the Langmuir-Blodgett method or a deposition technique known as Superlattice Nanowire Pattern Transfer (SNAP) have also been suggested to align nanostructures, but have yet to be combined with non high-resolution microfabrication techniques.

A common aspect of all previously known fabrication methods is that they do not involve standard microprocessing techniques involving over a micron in linewidth of resolution to align and form microsensors using nanostructures. Thus, the use of standard silicon processing techniques including batch processing have not been applied to nanotechnology.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises systems and methods that introduce standard microfabrication techniques to the field of nanotechnology.

In one embodiment, the subject innovation comprises a method of creating a microstructure incorporating a nanotechnology. The method can include forming a pattern of bottom electrodes on a substrate of the microstructure. One or more regions of the pattern of bottom electrodes can have a relatively high electric field gradient. Additionally, the method can include applying a suspension of nanostructures in a photoresist to the microstructure. In aspects, the method can also include performing dielectrophoresis on the suspension of nanostructures in the photoresists to create at least one aligned nanostructure.

In other aspects, the subject innovation can comprise a device, for example, a chemiresistor or other chemical sensor, a transistor, a Schottky diode, or thermal device. The sensor (or other device) can comprise a plurality of bottom electrodes that are arranged in a pattern that creates one or more regions with a high electric field gradient In addition, the sensor (or other device) can also include one or more aligned nanostructures that bridge opposing electrodes of the plurality of bottom electrodes. Top electrodes can also be included, and can be situated over at least a portion of the aligned nanostructures.

Systems and methods of the subject innovation have many possible applications, including emissions monitoring, leak detection, engine monitoring, security, fire detection, extra-vehicular-activity (EVA) applications, personal health monitoring, and environmental monitoring. Because this process is compatible with low temperatures and thin-film supports, it can be used in thin films for conductive coatings requiring electrical connections.

To accomplish the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
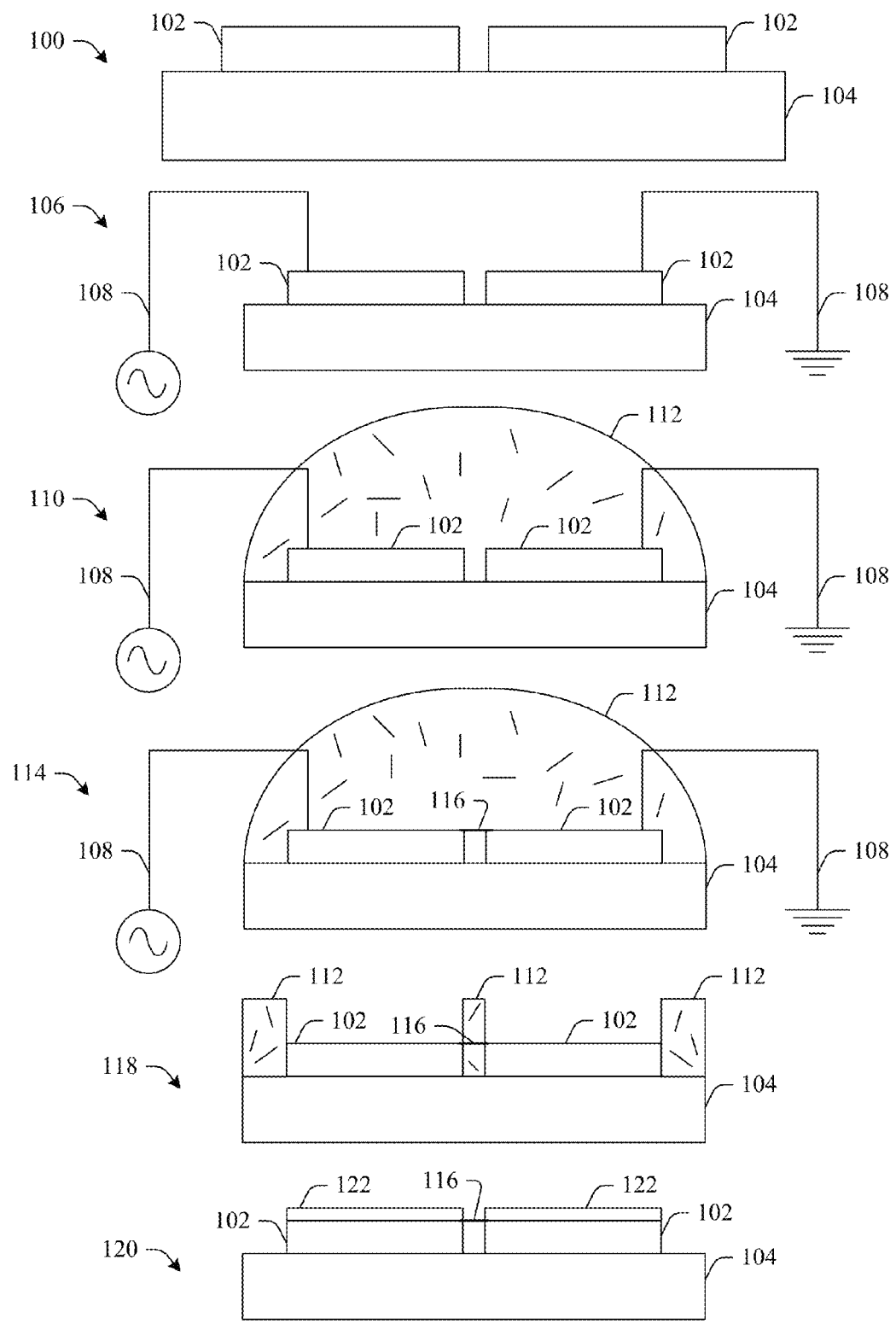
FIG. 1 illustrates a method of fabricating a device incorporating a nanostructure in accordance with an embodiment of the subject innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

In some embodiments, the innovation comprises a processing approach that can enable nanostructures to be used in conjunction with microfabrication techniques. As described further herein, dielectrophoresis (DEP) may be combined with standard microfabrication processing and materials to achieve reproducible, time-efficient fabrication of devices incorporating nanostructures.

In aspects described further herein, these systems and methods may be used in fabrication of micro sensors with nanostructures. Utilizing one or more approaches, standard microfabrication techniques can be applied to the repeated manufacture of nanostructured sensors on a microplatform by integrating standard microfabrication techniques with aligned nanostructures. In various embodiments of the subject innovation, DEP can be combined with conventional photolithography in order to fabricate chemical gas sensors with an ordered arrangement of nanostructures (e.g., nanorods, nanowires, or nanofibers), as well as dependable contacts.

In view of the aspects and features described, methodologies that may be implemented in accordance with embodiments of the subject innovation will be better appreciated with reference to the figures. While for purposes of simplicity of explanation, the methodologies are shown and described as a series of drawings representing steps or acts associated with the methodologies, it is to be understood and appreciated that the claimed subject matter is not limited by the order of the drawings, as some drawings may occur concurrently with other drawings and/or in different orders than what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated drawings may be required to implement the methodologies described hereinafter.

Turning to FIG. 1, in one embodiment, the innovation includes a method of fabricating a device incorporating a nanostructure. At act 100, a pattern of bottom electrodes 102 can be formed on a substrate 104 using microfabrication techniques (e.g., sputter deposition, etc.). Optionally, one or more regions of the pattern can be configured to so as to have a relatively high electric field gradient. As explained further below, subsequent alignment of nanostructures can be facilitated by such a pattern. One example of such a pattern 102 could be an interdigitated pattern with parallel "fingers": portions of pattern 102 that are, for example, straight or saw toothed in design. In some embodiments, the array of interdigitated fingers on a given wafer may be electrically connected so that a field applied across one set of fingers can be simultaneously applied to the full array of fingers on the wafer. The pattern of bottom electrodes 102 can be of most any of a variety of conducting materials as described further herein (e.g., Pt, Pd, etc.), and the substrate 104 can be of a semiconducting or insulating material (e.g., $Al_2O_3$, etc.).

With continued reference to FIG. 1, at act 106, a voltage source 108 can be connected to the pattern of bottom electrodes 102. At act 110, a suspension 112 of nanostructures in a photoresist can be applied to the microstructure, covering at least a portion of the pattern 102 and substrate 104. Photoresist suspension 112 may include nanostructures added to standard photoresist, with nanostructures to a sufficient consistency so as to be able to form a dilute suspension within the photoresist, as described further herein. At act 114, while the photoresist suspension has not solidified, an alternating electric field can be applied across the electrodes. In this manner, dielectrophoresis may be performed on the nanostructures within the photoresist suspension and on the wafer. This can align the nanostructures on the wafer as part of the standard microfabrication process, causing one or more aligned nanostructures 116 to bridge two or more electrodes of pattern 102. Considerations at this step include maintaining proper thickness and fluidity of the photoresist. After dielectrophoresis, the photoresist suspension can be allowed to solidify in a standard fashion to form a film on the wafer. Optionally, the suspension can be dispersed, for example by using spin coating techniques to form a film with a desired thickness (e.g., 6500-7500 Å), which can be determined by substantially any means (e.g., a stylus profilometer).

Continuing the discussion of FIG. 1, at act 118, processing of the wafer may continue, for example, by exposing the photoresist suspension 112 to allow the deposition of a second layer of electrodes on top of the pattern of bottom electrodes 102 already on the substrate 104. Such exposure can remove the photoresist suspension 112 from the pattern 102, but leave the aligned nanostructures 116 to be held in place by the remaining photoresist suspension 112, for example, by use of a mask to expose the pattern of bottom electrodes 102. The one or more aligned nanostructures 116 can be held in place by the photoresist but be exposed on the pattern of bottom electrodes 102 as the photoresist is developed in those regions. At act 120, a second layer of metal can be deposited over the pattern of bottom electrodes 102 to form a pattern of top electrodes 122 using standard photoresist processing techniques. This optional step can bury one or more contacts of the aligned nanostructures bridging the fingers between two layers of metal. After performing one or more of the above steps, further development of the device and removal of residual photoresist can be completed.

Figure 2:
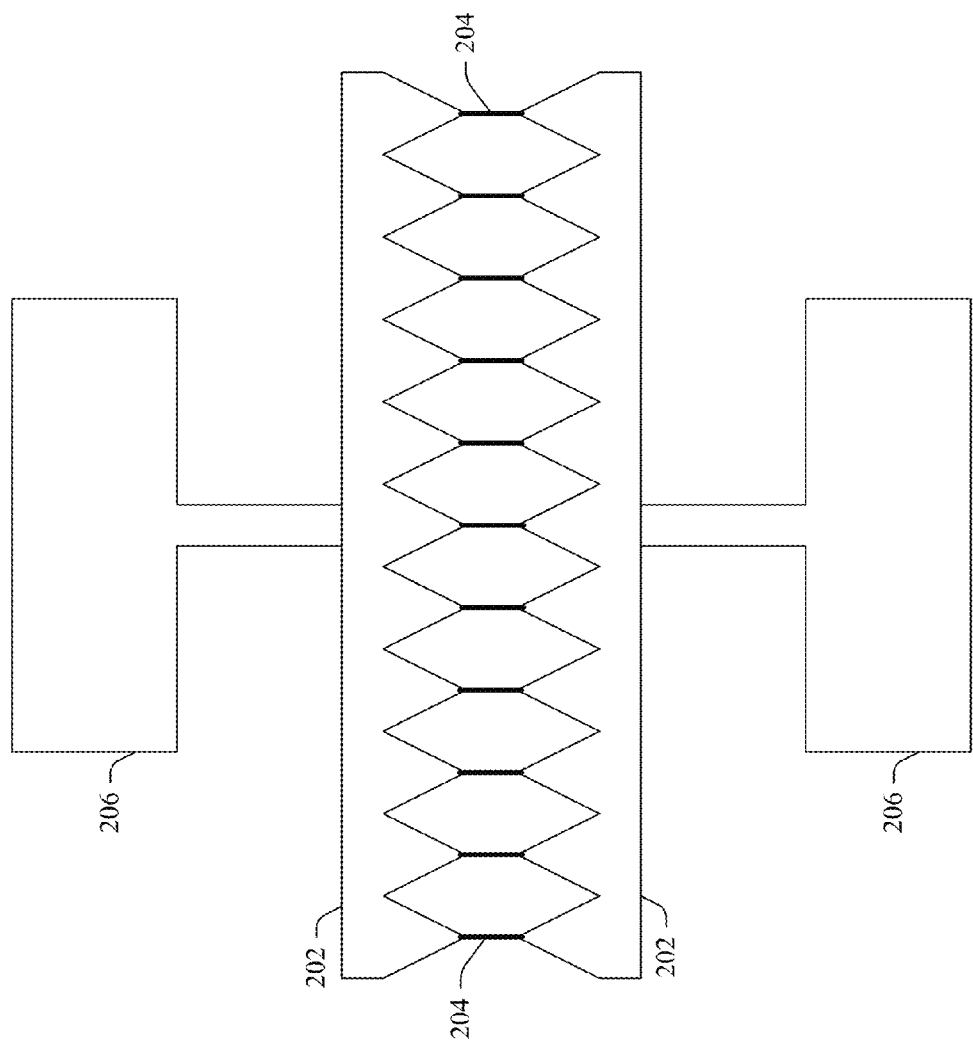
FIG. 2 illustrates a schematic of a chemiresistor sensor in accordance with aspects of the subject innovation.

FIG. 2 illustrates an example schematic of a chemiresistor sensor in accordance with aspects of the subject innovation. Although a chemiresistor sensor is shown, in other aspects of the present innovation, other types of devices can be constructed. As shown, a plurality of bottom electrodes 202 can be arranged in a pattern that creates one or more regions with a high electric field gradient, such as a sawtooth pattern with opposing points aligned near one another. One or more aligned nanostructures 204 can bridge opposing points. Additionally, contact pads 206 that are electrically connected to the plurality of bottom electrodes can be included so that a voltage can be applied across the bottom electrodes 202 and aligned nanostructures 204. Although not shown in FIG. 2, top electrodes can be situated over at least a portion of the aligned nanostructures in order to bury the contacts of the nanostructures. These top electrodes can be configured in a variety of manners, for example, in the same pattern as the bottom electrodes (e.g., sawtooth when the bottom electrodes are sawtoothed), or in a different pattern (e.g., rectangular when the bottom electrodes are sawtoothed). As described further herein, a chemiresistor sensor such as that depicted in FIG. 2 (or other type of device, e.g., a transistor, a Schottky diode, or thermal device) can provide a highly responsive sensor for detection. Such a sensor can be produced using multiple parallel nanostructures, or depending upon the lithographic patternation, can provide parallel processing for a number of individual sensor units, or both. In some embodiments of the subject innovation, either or both of these parallel options may alternatively be used in other (i.e., non-sensor) applications.

Different configurations of top electrodes as described above can have differing implications for a sensor or other device. For example, one consideration when using a matching pattern between top and bottom electrodes (e.g., both as sawteeth) is that the alignment of top and bottom electrodes may be slightly mismatched so that the top metal does not directly overlap the bottom electrode. This may be evidenced by curling top metal contacts and offset parallel metal patterns that can be seen in SEM images. Slight misalignment of a photoresist processing step can lead to a misalignment of the top and bottom electrodes, either exposing the bottom layer or leaving an overhanging film. Overall, however, this does not affect the ability to bury the electrical contacts for at least some of the nanowires, although it may reduce the efficiency of the process slightly by leaving other nanowires unsecured by the top layer of metal.

An alternate approach to the use of a matching pattern can address the misalignment issue. In such an approach, the bottom electrode can be covered with a larger overlapping pattern of top electrodes. For example, if the bottom pattern is sawtoothed, the top pattern could be a rectangular pattern that covers the sawteeth. The use of an overlapping top electrode can still allow the same type of bridging across the electrodes and can reduce the effects of misalignment while increasing the yield of the nanowires bridging the entire sensor. Sensors of this type were fabricated with similar properties to those of the matching pattern, both in terms of structure, as well as in overall sensor response. One feature of this approach is that more nanowires can be captured in the sensor structure; while still localized in the region of the electrodes, a top electrode with a larger overlapping pattern can bury nanowires of a variety of orientations.

The method of FIG. 1 can be used to fabricate gas sensors such as the chemiresistor sensors illustrated in FIG. 2 (or other types of devices, e.g., a transistor, a Schottky diode, or thermal device) and as described further herein. Additionally, systems and methods described herein can be employed in a wide range of other application. For example, dispersing metal oxide semiconductors using standard photolithographic techniques allows for ease of integration of the nanostructure into thin films for conductive coatings requiring electrical connections. One example application is to potentially replace fluor-doped $SnO_2$ (FTO) used as anode backing in bulk heterojunction solar cells. Moreover, the processes described herein are compatible with low temperature, thin film supports, such as flexible backings for electronics.

There are at least several advantages to fabrication via methods associated with the subject innovation. One important feature is the inclusion of "intact" nanorods where their aspect ratio is preserved. This can be particularly important for bridging electrical contact wires and minimizing the necessary electrical interface connections. A second point is that the use of a suspension of nanostructures in a photoresist compound is compatible with other mechanical fabrication methods, including drop coating, spin-coating, dip coating, jet-printing, and even transfer patternation (e.g., contact printing).

In various embodiments, systems and methods of the subject innovation can be used to produce an array of aligned nanostructures on a microplatform produced by standard microfabrication techniques. In accordance with aspects described herein, nanostructures can be aligned and fabricated on microplatforms as part of a standard microfabrication process, without requiring highly refined equipment beyond standard clean room processing equipment, removal of the devices from a clean room environment, or alignment of the nanostructures by hand. Additionally, through techniques described herein, including control of photoresist density, nanostructure concentration/dispersion, and the applied electric field, reproducible and batch fabricated sensor devices using nanostructures can be produced. In some embodiments, by burying the nanostructures in a sandwich of metallic contacts to the electrodes (e.g., interdigitated fingers), reproducible and reliable contacts to the nanostructures can be produced.

What follows is a more detailed discussion of systems, methods, and apparatuses associated with aspects of the subject innovation. To aid in the understanding of aspects of the subject innovation, theoretical analysis and experimental results associated with specific experiments that were conducted are discussed herein. However, although for the purposes of obtaining the results discussed herein, specific choices were made as to the selection of various aspects of the experiments and associated setups—such as choice of specific nanostructures (e.g., nanorods, nanowires, nanofibers, etc.), choice of circuit geometry (e.g., sawtooth electrodes, etc.), choice of materials (e.g., for nanostructures, catalysts, substrates, etc.), design and application of device (e.g., gas sensors, etc.), as well as other aspects—the systems and methods described herein can be employed in other contexts, as well. For example, aspects of the subject innovation can be utilized to incorporate nanostructures into devices made via microfabrication techniques, independent of the ultimate application of those devices. In another example, sensors and other devices discussed herein could be constructed with different choices of materials (e.g., for nanostructures, catalysts, substrates, etc.) than those used in the experiments discussed herein, and may have differing characteristics, as explained in greater detail below.

Microfabrication of Devices Incorporating Nanostructures

Nanostructures used in connection with the subject innovation can be produced by a variety of methods, including without limit methods described further herein. Additionally, although one-dimensional nanostructures (e.g., nanorods, nanofibers, nanowires, etc.) are primarily discussed herein, various systems and methods of the subject innovation can be applicable to other nanostructures.

Different compositions of nanostructures were used in the experiments, including both multiwalled carbon nanotubes (MWCNT) and metal oxide nanostructures. Although specific nanostructures were used in the experiments, others could be used, for example, nanostructures that include a metal oxide including but not limited to tin dioxide, titanium dioxide, indium dioxide, iron oxide, indium tin oxide, zinc oxide, or molybdenum trioxide, chemically reactive metals or alloys of palladium, platinum, gold or silver, or a carbon-based material such as carbon nanotubes, coated carbon nanotubes, or doped carbon nanotubes. The diameter of the MWCNTs typically ranged from 100-250 nm with lengths typically ranging from 10 to 40 microns. The MWCNTs were grown at 750° C. in a gas flow of humid carbon monoxide, hydrogen, ethylene, and carbon dioxide. The iron catalyst was removed from the MWCNTs by subsequent annealing at 1700° C. This post treatment also removed defects in the sidewalls of the tubes, allowing for more reproducible physisorption of analytes onto the tubes in preference to charge transfer effects that could otherwise occur at defect sites.

In one example, an experimental setup discussed herein utilized $SnO_2$ nanorods produced using a thermal evaporation-condensation (TEC) approach. Tin (IV) oxide was evaporated within a small flow of argon and 5% oxygen in a tube furnace from 700-1000° C. While in the vapor phase, the oxide self-assembled into coherent rods several micrometers in length (i.e., nanorods, with lengths typically in the tens of microns) along with other geometries. In some situations without the presence of a catalyst, growth proceeded by self-catalyzed vapor-solid (VS) mechanism with the boat providing heteroepitaxial nucleation sites. After growth, the nanorods were separated from the resulting material using gravimetric separation. The rods varied in length from 3 μm to a typical range of 10 μm-100 μm (some as high as 500 μm), with diameters ranging from 40 to 300 nm. Structural characterization of the nanostructures was performed with transmission electron microscopy (TEM) and morphology examined with scanning electron microscopy (SEM) prior to processing.

DEP was used to align multiple nanorods within a photoresist-based suspension between platinum (Pt) electrodes on a polished alumina ($Al_2O_3$) substrate (alternatively, other semiconductors or insulators may be used as substrates, e.g., silicon, silicon carbide, silicon dioxide, silicon on insulator, gallium nitride, aluminum oxide, quartz, sapphire, germanium, gallium arsenide (GaAs), an alloy of silicon and germanium, indium phosphide, insulator coated metals, etc.). The base sensor layout was designed to assist in the alignment of the nanorods by selectively enhancing the electric field strength and allowing for the quick production of sensor arrays. A second layer of metal was incorporated using the DEP suspension in standard microfabrication methods immediately after alignment. This enabled burial of the ends of the nanorods (which were in contact with the underlying electrodes) within another, thinner layer of Pt. Although Pt was selected for the electrodes for the purpose of the experiment based on its catalytic and other properties discussed below, other conducting materials could be selected based upon properties that may be important in specific applications (e.g., bulk properties, catalytic properties, cost, etc.). For example, high temperature application environments may require noble metal electrodes to avoid degradation. For the experimental results that follow, MWCNT sensors used a bottom platinum (Pt) electrode sputtered with a thickness of 1800 Å, and a top electrode of titanium (Ti) with a thickness of 500 Å. Metal oxide sensors used a bottom layer of copper (Cu), Pt, or a combination of platinum oxide and platinum ($PtO_x$/Pt, e.g., at 2500 Å), and the top layer can be Pt or Ti. Electrical contact was verified during testing by the response to $H_2$, $C_3H_6$, and $NO_x$ gases at a range of temperatures. Testing was performed on a stage with temperature control and tungsten probes were used for electrical connection. Gas flowed into the testing chamber at a flow rate of 4000 sccm (standard cubic centimeters per minute). Response of the sensor was measured by current output at a constant voltage. In some example sensors constructed with a sawtooth pattern for experiments, the number of aligned nanostructures bridging each sawtooth varied. For instance, in an example sensor constructed using MWCNTs as the nanostructures, the number varied between 1 and 11 bridging each sawtooth, with an average of approximately 4. For an example $SnO_2$ sensor, the number varied between 0 and 10 bridging each sawtooth, with an average of approximately 4.

DEP alignment is applicable to a range of nanoscale materials and morphologies, unlike electrophoresis, which describes the movement of charged particles during the application of an electric field. During DEP, an induced dipole interacts with the applied electric field gradient, resulting in a time-dependent force, as shown in equation 1:

$$F_{dep} = (p(t) \cdot \nabla) E(t) \tag{1}$$

where $F_{dep}$ is the time-dependent force in an alternating current (AC) field, $E(t)$ is the electric field, and $p(t)$ is the dipole. In the case of a nanostructure such as a nanowire or nanorod, the induced dipole is dependent on nanowire dimensions, the difference in the dielectric constant between the nanowires and suspending medium, and the electric field gradient, as seen in equation 2:

$$p(t) = 4\pi \in_m l r^2 Re(K_a) \nabla |E_{rms}|^2 \tag{2}$$

where $\in_m$ is the permittivity of the suspending medium, l and r are the length and radius of the nanowire, respectively, and $E_{rms}$ is the root mean square of the electric field. The $K_a$ factor depends on the complex permittivity of both the particle and the medium.

In various embodiments, both the electrode geometry and the solvent used for DEP can be selected so as to facilitate fabrication of devices incorporating nanostructures. Because the dipole depends upon the gradient of the electric field, selection of the electrode geometry used (e.g., the irregular geometry of the sawtooth pattern) can help create an E-field gradient that can result in movement of the nanostructures (e.g., $SnO_2$ nanorods). Alignment on portions of the electrode geometry associated with certain E-field gradients (e.g., between sawteeth on a sawtooth pattern) can occur due to the differential hydrodynamic drag force dictated by the rod aspect ratio, as well as a torque induced within the AC electric field as the nanorod rotates out of line to the E-field. An AC field can be used to prevent electrochemical reactions at electrode surfaces.

Traditionally, the suspending medium used in DEP to suspend the nanostructures is either dimethylformamide (DMF) or a light alcohol. However, in aspects of the subject innovation, photoresist can be used as a suspending medium for DEP in order to assist with subsequent processing steps. By controlling the amount of nanorods added into the photoresist-based suspension, a suspension of $SnO_2$ nanorods can be achieved and shown to be compatible with subsequent DEP and conventional micro-processing steps, as described further herein. An outline of the fabrication steps is illustrated in FIG. 1, as described above.

The bottom electrodes can be fabricated by substantially any means. For the purposes of obtaining the experimental results discussed herein, the bottom electrodes were sputter deposited (at 32 W DC, a pressure of 4 mTorr, with a $Ar/O_2$ (80%/20%) mixture for the first 3.5 min to assist with adhesion on the substrate) on a polished alumina substrate and patterned using conventional lift-off techniques. The bottom electrodes were arranged in a sawtooth pattern with spacing between the sawteeth of approximately 5 μm for the purposes of the experiment, which was a small enough distance to capture the shorter nanorods as well as generate a stronger electric field then a larger distance would. An alumina substrate was used in the experiment to ensure isolation between electrodes, as well as prevent any substrate effects due to interaction of the tube with the surface. Platinum (Pt 2450 Å thick) was used for both the bottom electrode metal and the top layer of metal (used to sandwich the nanorod ends and ensure electrical contact) due to its stability and compatibility to the other materials used, as well as its capability to enhance the reaction of the nanorods through its catalytic properties. Although multiple photoresists could be used, the photoresist (PR) Shipley S1805 was used as the dispersing medium for the $SnO_2$ nanorods because of its low viscosity. It was experimentally determined that a concentration of 0.03 g of $SnO_2$ nanorods in 15 mL of S1805 was optimal for maintaining fluidity of the suspension as well as preventing undesired clumping of rods. The suspension was sonicated to thoroughly mix the rods and to break up any clumps. After the suspension was prepared, it was deposited onto the existing electrode pattern using a pipette, although the suspension may be placed on the pattern by any means by which photoresist can be applied. Tungsten probes were placed on the contact pads using a standard probe station, and an AC field (with a frequency of 20 MHz, and a peak-to-peak voltage of $10V_{p-p}$) was generated for twenty minutes using a function generator, after which approximately 50 to 85% of sawteeth were bridged by nanorods. A sinuosoidal signal was used because it makes use of the linear relationship between the effective dipole moment and the electric field. The probes were removed, and the suspension underwent typical photoresist processing steps (i.e., spun at 6000 rpm 60 s, soft-bake at 115° C. for 2 min, exposure 4 s at 8 mW, and developing in MF319 developer). A top layer of Pt (1000 Å thick) was then sputter deposited (at 32 W DC, a pressure of 4 mTorr, with Ar only) and selectively patterned by removing the excess photoresist-based suspension, leaving the desired sensor structure. The top contacts were in a rectangular shape, to reduce the possibility of alignment errors as well as capturing excess nanorods that could be in various orientations.

Figure 3:
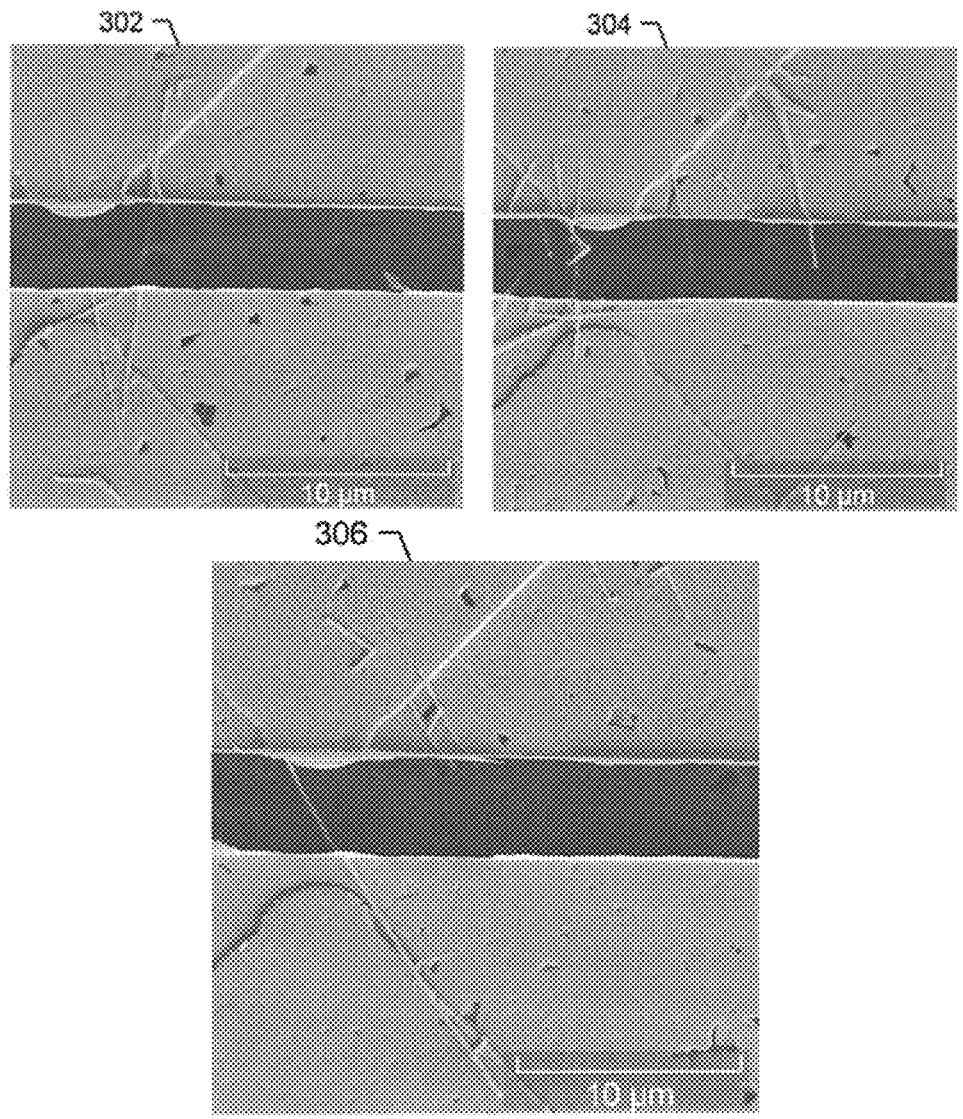
FIG. 3 shows scanning electron microscope images of a sensor fabricated using a method of the subject innovation.

The resulting chemical sensor included two electrodes with $SnO_2$ nanorods bridging between and nanorod ends sandwiched between two layers of Pt. Optionally, the density and type of nanostructures bridging the electrodes can be influenced with several techniques. The density of nanorods bridging electrodes can be increased in a number of ways, for example, by applying multiple coatings of the suspension and application of DEP, as well as by changing the concentration of nanorods within the low-viscosity photoresist suspension. When using the multiple coating approach, after act 114 of FIG. 1 a gentle solvent rinse can be performed to remove the existing suspension and any loose nanorods. The sample can then undergo steps 106, 110, and 114 of FIG. 1, repeating until a desired density is reached. Optionally, between these steps the sample can be examined under high magnification to check on the bridging progress. The greater the density of nanorods on the sample, the easier it is to image. It was also found that frequency influences the length of nanorods aligned between teeth. For lengths matching the ranges made using the TEC technique (approximately 3 to 10 µm), higher frequencies are found to capture the greatest variety of lengths. At low frequencies (e.g., 20 Hz) the majority of tubes aligned are limited to lengths greater than 10 µm. For SnO2 nanowires with lengths of 5 µm and 4 µm, preferred frequencies for alignment were found at 20 kHz and 2 MHz, respectively. When the frequency is increased, shorter rods are also captured between the sawteeth. FIG. 3 shows scanning electron microscope images 302, 304, and 306 of a sensor fabricated using a method of the subject innovation. In the figure, multiple nanorods are aligned between the electrodes with contacts achieved by sandwiching the nanorod ends between two layers of metal.

As noted, the length of the nanostructures deposited across the electrode gap can be affected by the AC frequency used to align the nanostructures. Thus, this can allow for the possibility of reproducible manipulation at a single point or over an array of devices. In some aspects, different portions of a pattern of bottom electrodes can have varying lengths of gaps between portions of the pattern (e.g., sawteeth). This can optionally be combined with selecting varying lengths of nanostructures based on the response to AC frequency, in order to facilitate selective manipulation of nanostructures at one or more points on the pattern of bottom electrodes.

Sensors fabricated using the methods outlined above can be used in a resistor-based sensor platform for sensing chemical species of interest in a wide range of fields, including environmental monitoring, fire detection, emissions monitoring, and biochemical sensing. For example, the detection of nitric oxide (NO) is biologically relevant given its importance related to the monitoring of asthma conditions. In particular, as a free radical that reacts with oxidants and antioxidants, NO in exhaled breath reflects the state of the airway and has been proposed as a marker of airway inflammation and a guide for anti-inflammatory therapy in asthma. High levels of NO are well documented in asthma, and decrease in response to treatment with corticosteroids. NO is produced by nitric oxide synthases (NOS), including constitutive and inducible enzymes, all isoforms of which are present in the lung. Further, the measurement of both NO and $NO_2$ ($NO_x$) is of considerable interest related to engine exhaust emissions and is an indicator of the combustion processes within the engine. Reduction of $NO_x$ emissions is an objective for the NASA Supersonics program.

Figure 4:
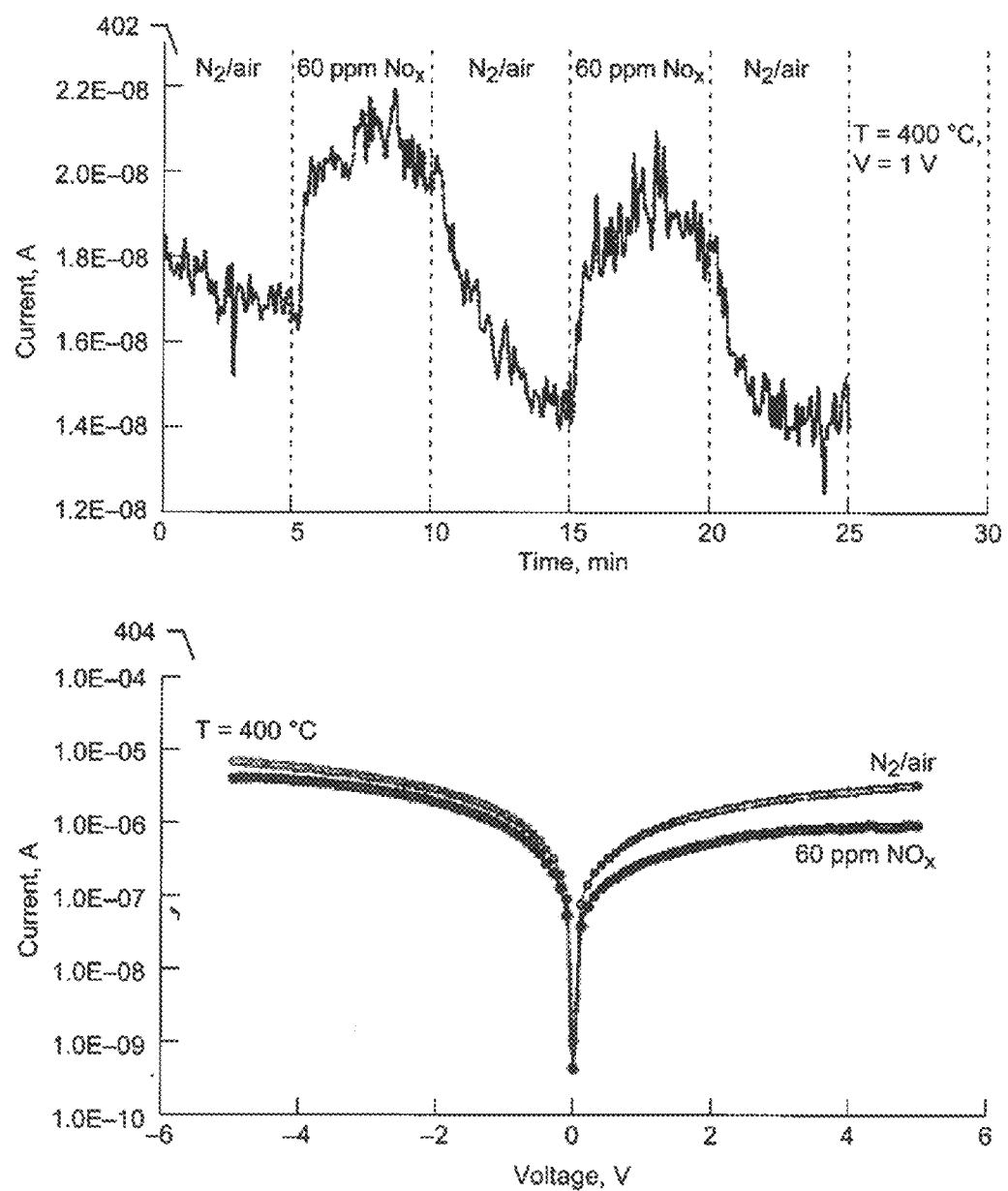
FIG. 4 depicts two graphs illustrating the response to $NO_x$ of an example $SnO_2$ sensor fabricated according to aspects of the subject innovation.

FIG. 4 depicts two graphs illustrating the response to $NO_x$ of an example $SnO_2$ sensor fabricated according to aspects of the subject innovation. Graph 402 depicts the current in logarithmic scale against time in minutes at 1V after exposure to 60 ppm $NO_x$. at a temperature of 400° C. Graph 404 measures the absolute value of the current (in amperes) in logarithmic scale against voltage (in volts) for −5V to 5V at 400° C. for the $SnO_2$ sensor in the presence of both $N_2$/Air (light gray line) and 60 ppm $NO_x$ (dark gray line). This data demonstrates the effectiveness of sensors produced in accordance with aspects of the subject innovation. In addition to the $NO_x$ testing results shown in FIG. 4, the sensors were tested with and showed response to $H_2$ and $C_3H_6$. Detection of at least 200 ppm for both $H_2$ and $C_3H_6$ was achieved up to 600° C., and, as shown by FIG. 4, successful detection of 60 ppm $NO_x$ occurred at 400° C. Response was found to be the most stable and repeatable for all three of the tested species ($H_2$, $C_3H_6$, and $NO_x$) at 400° C.

As shown by FIG. 4 and the above discussion, nanostructures (e.g., semiconducting $SnO_2$ nanorods) integrated into a microsensor platform via aspects of the subject innovation have been demonstrated and sensing response occurred at a range of temperatures (for the $SnO_2$ nanorods, up to 600° C.). They are sensitive to a range of chemical species. In some embodiments, response and selectivity of sensors can be enhanced in a number of ways. Examples of ways to increase response and/or selectivity include the use of a sputtered catalyst, lower temperatures, and/or different nanorods that have shown increased sensitivity to $NO_x$ (e.g., Indium Tin Oxide or Tungsten Oxide).

Figure 5:
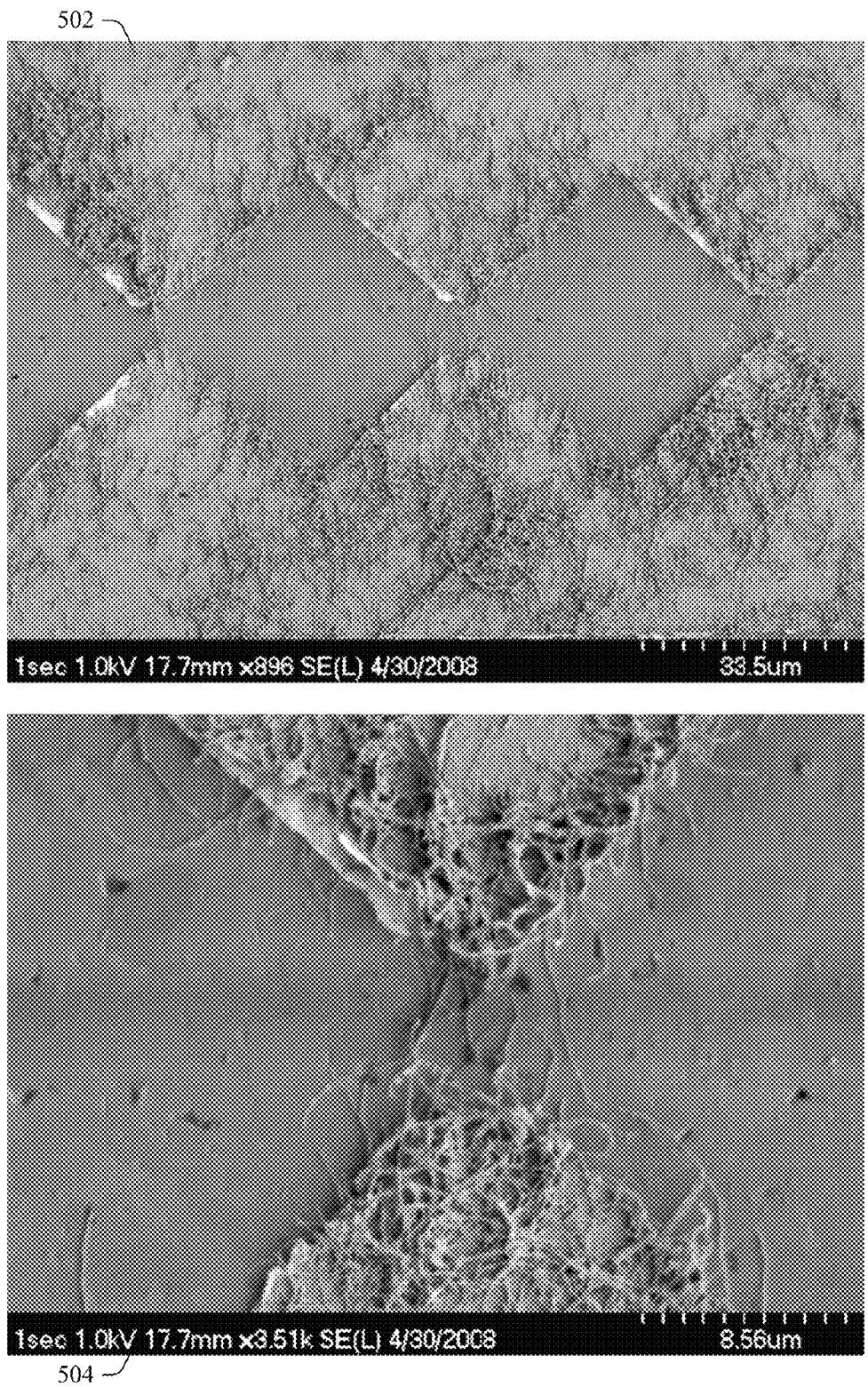
FIG. 5 shows Scanning Electron Micrographs (SEM) of sawtooth interdigitated finger patterns with multiwalled carbon nanotubes (MWCNT) bridging the electrodes.
Figure 6:
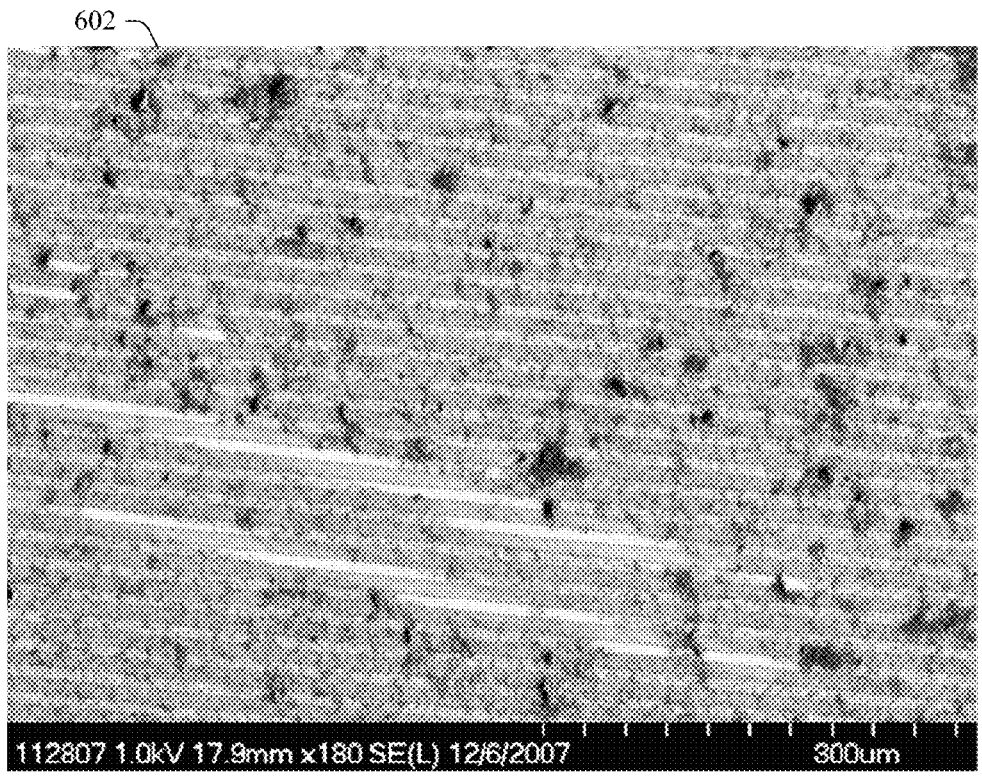
FIG. 6 contains SEMs showing carbon nanotubes deposited on a substrate by a prior art method of dispersing them in a suspension and depositing the suspension on a substrate.
Figure 6:
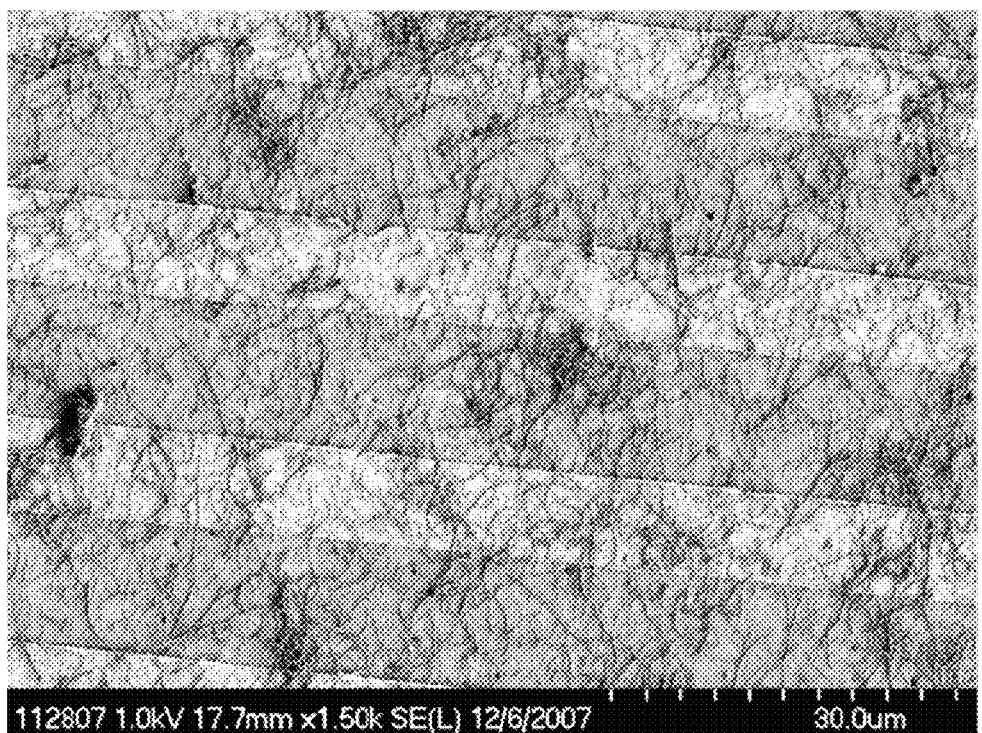

FIG. 5 shows Scanning Electron Micrographs (SEM) 502 and 504 of sawtooth interdigitated finger patterns with multiwalled carbon nanotubes (MWCNT) bridging the electrodes. In the setup used to obtain the images of FIG. 5, the substrate 104 was alumina ($Al_2O_3$), the pattern of bottom electrodes 102 was platinum (Pt) at 1,850 Å (arranged in a sawtooth interdigitated finger pattern, as indicated above and in FIG. 5), titanium (Ti) at 500 Å was used for the pattern of top electrodes 122, and MWCNTs as the nanostructured material forming the aligned nanostructures 116. As seen in micrographs 502 and 504, contact between the aligned nanostructures 116 with the pattern of bottom electrodes 102 is secured by depositing the pattern of top electrodes 122 over both the aligned nanostructures 116 end and pattern of bottom electrodes 102. Nanotubes are seen to bridge across the electrodes for multiple electrodes in FIG. 5. For comparison, FIG. 6 contains SEMs showing carbon nanotubes deposited on a substrate by a prior art method of dispersing them in a suspension and depositing the suspension on a substrate. The resulting sensor structure in FIG. 6 is random and uncontrolled, resembling straw dropped on the floor rather than a reproducibly processed material. The contacts to the sensing nanostructure in FIG. 6 are poorly defined and not reproducible. In contrast to FIG. 6, control of the nanotube alignment in FIG. 5 is seen to have significantly improved and bridging of the contacts by the aligned nanostructures 116 is restricted to the small gaps between the teeth of the pattern of bottom electrodes 102.

Figure 7:
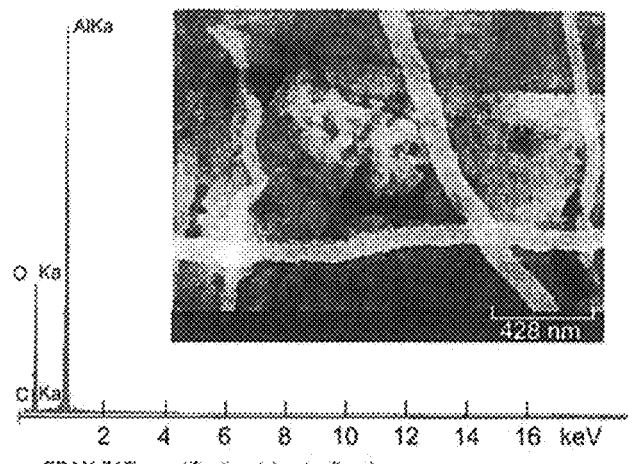
FIG. 7 shows a sampling of data obtained from energy dispersive spectroscopy by X-ray (EDS) to verify the chemical composition of each component of the structure in FIG. 5.
Figure 7:
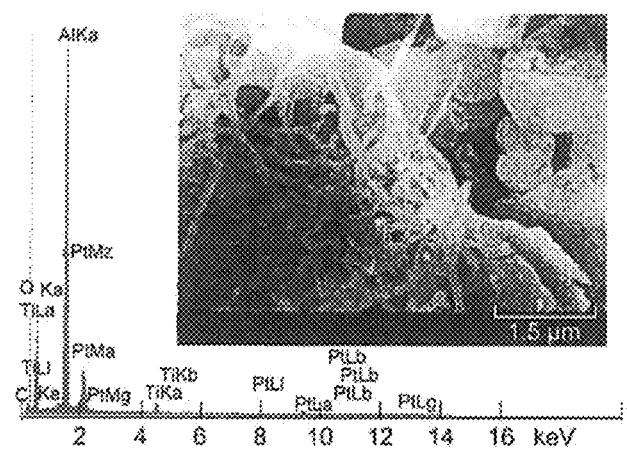

FIG. 7 shows a sampling of data obtained from energy dispersive spectroscopy by X-ray (EDS) to verify the chemical composition of each component of the structure in FIG. 5. As seen in numerical results 702 and 704, the top and bottom electrodes are shown to be metallic, the aligned nanostructures 116 (in this case, the bridging nanotubes) are seen to indeed be carbon, and the areas surrounding the nanotubes are the original $Al_2O_3$ substrate 104 with no deposition of metal between the electrodes. In other words, the data from EDS confirms the successful fabrication of a sensor which has the metal electrodes with buried carbon nanotube contacts and bridging carbon nanotubes across the electrodes.

Structure of Metal Oxide Semiconductors Nanostructures

Nanostructures used in connection with the systems and methods of the subject innovation can have varying structure, morphology, and composition. As discussed in greater detail below, comparisons were made between $SnO_2$, ZnO, and $TiO_2$ single-crystal nanowires and $SnO_2$ polycrystalline nanofibers in the context of gas sensing. Both of these nanostructures (i.e., the nanowires and the nanofibers) possess a one-dimensional morphology. Different synthesis methods can be used to produce these materials: thermal evaporation-condensation (TEC), controlled oxidation, and electrospinning, each having different advantages and limitations, as discussed below. The term TEC is used to more accurately describe the process of nanowire formation traditionally referred to as chemical vapor deposition (CVD). Additionally, practical concerns associated with harvesting, purification, and integration of these materials into microscale devices (e.g., sensing devices) are discussed below. Moreover, in experiments discussed infra, these materials were surface coated with Pd and Pt nanoparticles for comparison to the nascent (i.e., uncoated) form. Gas sensing tests, with respect to $H_2$, were conducted at ambient and elevated temperatures. As shown below, comparative normalized responses and time constants for the catalyst and noncatalyst systems can be used for selection of a metal-oxide nanostructure and catalyst combination. With temperature-dependent data, Arrhenius analyses were made to determine activation energies for the catalyst-assisted systems. However, although the experiments and accompanying results discussed below indicate materials with desirable sensing characteristics, in some situations, other materials may be selected based on a variety of considerations, including, for example, cost, availability of materials, intended application, etc.

Adsorption of $O_2$ on a MOS (e.g., $SnO_2$) is accompanied by electronic charge transfer from the conduction band to the surface. Hence, a surface region is depleted in electron density and is called the depletion layer. In the presence of a reducing gas, a chemical reaction between gas molecules and negatively charged adsorbed oxygen species (O⁻ . . . , $O_2^-$ . . . ) leads to electron transfer back into the surface, thereby increasing the conductivity. Therein, the fundamental sensing mechanism of metal-oxide-based gas sensors relies upon this change in electrical conductivity in response to ambient gases. These processes are generically expressed by reactions 3 and 4 below:

$$\frac{1}{2}O_2(g)+e^-(cb) \rightleftharpoons O^-(ad) \quad (3)$$

$$H_2(g)+O^-(ad) \rightarrow H_2O(g) \quad (4)$$

Traditional MOS gas sensors have often used thin films. However, films, which typically have large grains, have multiple drawbacks, suffering from the variability in accessible surface area, grain size, pore size, and film thickness. Most importantly, sintering leads to lack of long-term stability because of enlargement of the grains and the resulting changes in the grain boundaries and sensor response. Furthermore, in polycrystalline and thick-film devices, only a relatively small fraction of the material near the grain boundaries is active in modifying the electrical transport properties, which limits the sensitivity of the MOS gas sensor. Because of the drawbacks associated with film-based based gas sensors, superior sensors can be constructed by controlling the morphology and crystallinity with uniformity. Ideally, this sensing element would present a linear, one-dimensional morphology for device integration. This can be accomplished via utilizing nanostructures such as those fabricated in accordance with systems and methods of the subject innovation.

Because an increase in the number of chemisorption (reaction) sites leads to an increase in the electronic charge transfer, reduction of the grain size leads to an increase in the sensitivity. Compared to other structures, nanostructures such as nanocrystalline materials provide a tremendous increase in the surface/bulk ratio for a material. Nanostructures have multiple aspects that are particularly relevant to sensors, including high surface area and controlled structure. Surface area is critical to gas adsorption. Correspondingly, high surface area translates into high sensitivity because the depletion layer becomes a significant fraction of the particle with decreasing particle size. Controlled structure provides the reactive sites for adsorption and their modulation of the overall conductance. Relative to micron-sized grains, powders, layers, or films, nanoparticles offer 10 to 100-fold increases in each parameter. Additionally, nanoparticles are more stable and less likely to sinter, yielding a more stable sensor. Moreover, nanostructures often possess unusual reactivities due to size and surface structure, reflecting defects, interstitial atoms, and incomplete bonding. Such activity further enhances sensitivity and lowers operation temperature. Operation at lower temperature saves power. It also extends operating lifetime and maintains reproducibility by preventing grain growth by sintering. Finally, lower temperature combined with structure control can advantageously yield selectivity. In summary, the use of nanocrystalline material decreases particle growth while, given the increased number of chemically sensitive particle boundaries, improving sensor sensitivity, stability, and response time. Moreover, carrier depletion (or replenishment) throughout the "bulk" nanostructure will expand the sensor dynamic range by the virtue of adsorbates leading to full charge depletion (or replenishment) with corresponding infinite or near-zero resistance, respectively. Thus, the potential advantages of nanostructures for sensor applications are clear.

Despite the perceived advantage of single-crystal nanowires relative to polycrystalline nanofibers or other particle-based assemblies, other factors require consideration. For example, the depletion layer thickness of a single-crystal nanowire is comparatively small, relative to nearly all nanowire diameters. Though dependent upon temperature and surface defect density, it is generally considered to be –5 to 20 nm, dependent upon temperature and material crystallinity. Thus even a 100-nm diameter nanowire may possess an unaltered central core. With regards to particle-based morphologies, this scenario is undesirable as the material is underutilized and worse, has large shorts between particles. Sensing is strictly limited to the junctions between particles or grains. However, if the material is highly crystalline with few defects, its conductivity may be low and conduction may be effectively restricted to the near-surface region, an optimal condition for transduction of chemisorption with oxidizing and reducing species. Nonetheless, for oxides with dopants or a high concentration of defects, all portions of the nanowire or particle contribute to the overall conductivity. Depending upon the degree of necking between the particles, varied contributions of the particle core and oxidizable/reducible shell can contribute to the conductivity as modulated by ambient gases.

A common misconception is that these metal oxide materials are inherently semiconducting. However, in stoichiometric form, charge balance exists and perfect crystalline forms are insulating. As with silicon, dopants or lattice defects are required to impart free charge carriers to yield conductivity. Notably, vacancies are also quite effective in providing charge carriers. These are readily introduced by most bottom-up fabrication methods including thermal evaporation-condensation (TEC), solvothermal, etc., which have been shown by photocharacterization measurements. Cation interstitials or O-atom vacancies in particular are predominant defects. Different crystalline faces may expose unterminated valencies, which then allow for chemisorption of oxygen or water. The result is termination of these sites by either hydroxyl or O or $O_2$ groups.

The relative advantages of single-crystal and polycrystalline morphologies for reactive gas sensing are discussed further herein to aid in an understanding of the subject innovation. Numerous considerations affect the performance of these two morphologies. Conductance variation in the depletion layer along a nanowire may be considered as roughly linear with change in carrier concentration and hence, with ambient gas concentration at the very low concentrations generally of interest. Conductance across a junction potential between two crystalline nanoparticles or polycrystalline grains is exponentially dependent upon the width of the adjoining depletion layers. The width or thickness varies with free charge carrier concentration, again in response to ambient gas concentration. This variation in charge carrier concentration is exponentially amplified. Junction potentials vary depending upon the relative orientation of different crystalline grains, accessibility to ambient gases etc., while particle assemblies offer myriad parallel conducting paths. Following are detailed comparisons between one-dimensional elements of single and polycrystalline morphology.

In order to focus performance differences solely upon the nanostructure, the following comparisons were made between these two forms (single and polycrystalline) with the same morphology. The morphology of a one-dimensional filament that could bridge opposing electrodes was selected. Nanowires, produced by TEC and controlled oxidation, and nanofibers produced by electrospinning served as the basis for this comparison. A number of trends emerged for the nanowires and nanofibers with temperature, as discussed below.

Figure 8:
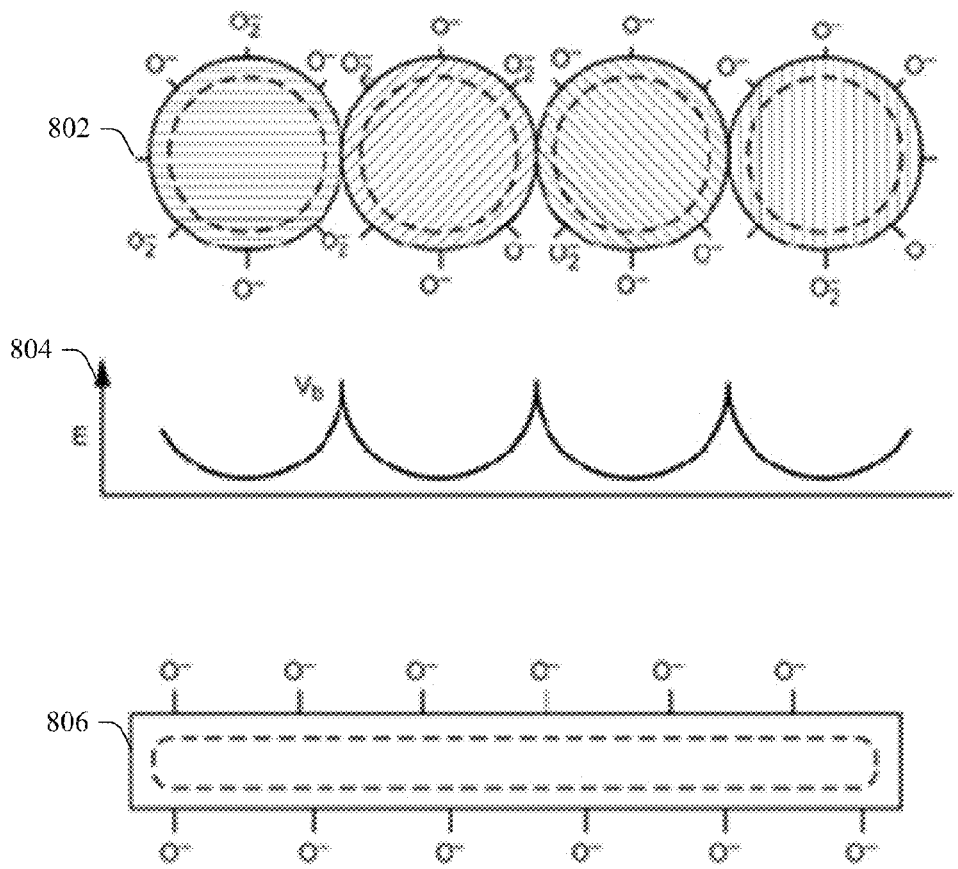
FIG. 8 illustrates structural differences between a single-crystal nanowire and a polycrystalline nanofiber.

FIG. 8 illustrates structural differences between a single-crystal nanowire and a polycrystalline nanofiber. FIG. 8 shows a schematic illustration of potential barriers between nanoparticles formed by the juxtaposition of depletion layers within a polycrystalline nanofiber at 802 and graphically at 804, and the continuous depletion layer surrounding the nanowire at 806. In the single-crystal case, a continuous depletion layer forms around the wire perimeter, as shown at 806. If it is of sufficiently small diameter, the entire wire is volumetrically depleted of electron density. In the case of the nanofiber, seen in 802 and graphically represented at 804, the net conductivity, σ, is the summation of the myriad potential barriers between particles and grains. This is described by Equation 5, $$\sigma \propto \sum_n \exp\left(\frac{-q|V_b|}{kT}\right) \quad (5)$$

where q is the elementary electron charge, $V_b$ is the grain boundary potential, k is the Boltzmann's constant, and T is the temperature. The nanowire can be considered as the limit of the summation describing the nanofiber case as suggested by Equation 6, $$\sigma \propto \lim_{n \to \infty} \sum_n \exp\left(\frac{-q|V_b|}{kT}\right) \quad (6)$$

In most situations, the nanowire diameter is generally larger than twice the depletion layer thickness. The crystalline structure may not support a high surface density of defect sites or concentration of chemisorbed oxygen species. Alternatively, in the polycrystalline nanofiber (or aggregates), not all particle and grain junctions may be accessible to adsorbates. Such spots can correspond to "shorts" whose resistances are unmodulated by adsorbates. Additionally, there can be a considerable variation in potential boundaries, given the random orientation of single-crystal particles with respect to each other. Necessarily, the resistance will be dominated by only the highest potential barriers.

The following experiments and results compare advantages and limitations of multiple nanostructure morphologies and corresponding synthesis methods for gas-sensing using an interdigitated array platform similar to that described above in connection with aspects of the subject innovation. Harvesting, purification (where applicable), integration into the device, and comparative sensing measurements discussed below involve oxides, for example, $SnO_2$, from each synthesis method (TEC and electrospinning), $TiO_2$ produced by controlled oxidation and ZnO produced by TEC. Although the experimental results discussed below relate to metal oxides, other nanostructures may also be used in various embodiments of the subject innovation. Using a chemiresistor approach, test results were obtained and compared on the basis of normalized response and rate constant. Catalyst advantages for response, sensitivity, and response rate were determined. Common to all studies was an interdigitated array and integral heater platform. The results discussed herein were judged on the basis of normalized response and response time. Advantages and limitations of each method are discussed and summarized below.

As used herein, the linear single-crystalline element formed by TEC and controlled oxidation is referred to as a "nanowire." Also as used herein, the linear polycrystalline element formed by calcining an electrospun fiber is referred to as a "nanofiber."

Synthesis Methods

There are multiple approaches that have been developed for synthesizing nanoforms of MOSs, including TEC synthesis, controlled oxidation, and electrospinning. Each method offers nanoscale sensor elements that can be incorporated into sensors such as those associated with various aspects of the subject innovation. Producing free-standing structures, issues of porosity or film thickness are negated. Additionally, the nanoscale materials permit rapid time response, limited only by gas diffusional and/or convective processes. As explained further herein, each synthesis method and product has attendant advantages and limitations. Apart from device fabrication and manufacturing issues, these methods produce elements that differ primarily in their crystallinity and morphology. TEC and controlled oxidation syntheses produce single-crystalline nanowires. Electrospinning produces polycrystalline elements upon calcination of the (as-spun) sol-gel fiber. As explained above, material crystallinity is the single largest performance factor and can have profound consequences upon the viability of the material for sensing and devices based on it.

Figure 9:
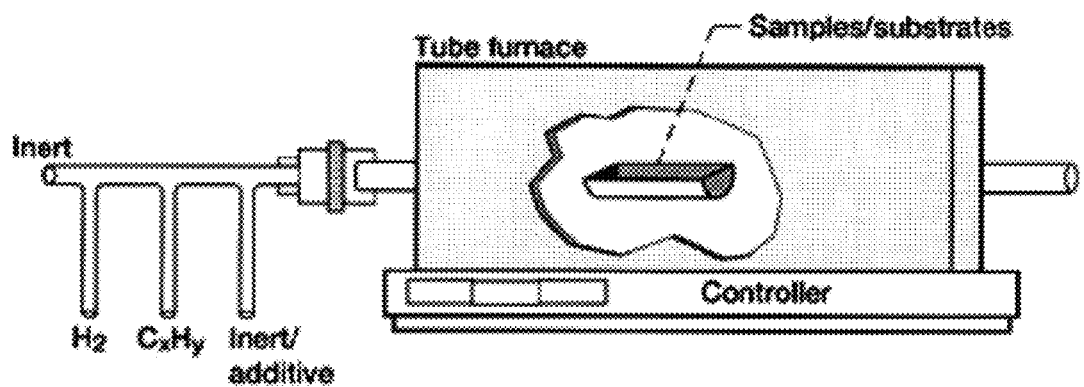
FIG. 9 illustrates a high-temperature furnace capable of synthesizing metal oxide and other semiconductors.

FIG. 9 illustrates a high-temperature furnace capable of synthesizing metal oxide and other semiconductors. Semiconductors may be synthesized through either vapor-solid (VS) or vapor-liquid-solid (VLS) mechanisms, utilizing such a high-temperature furnace. In either case, a substoichiometric oxide can be produced as a vapor at elevated temperature under reducing conditions. Through self-assembly, as guided by flow and temperature gradients, metal-oxide vapor can form the nanowire. The MOS nanostructures can grow in various geometries, depending upon factors such as the rate of vapor supply and the relative surface energies of different crystalline facets. These one-dimensional geometries favor changes in the electronic states of the surface to be observed by conductance measurements and optical techniques by virtue of the high surface area and charge depletion layer extending nearly throughout the nanostructure. There are multiple critical parameters common to TEC, including precursors, temperature, pressure, gas environment, and residence time.

Two approaches for nanowire synthesis are discussed herein: oxidation of the base metal and reduction of the higher oxide. Each approach offers particular advantages. Oxidation of the base metal provides advantages including more straightforward control of the metal vapor pressure and higher phase purity by the controlled oxidation. It also offers the opportunity to tailor the defect structure by the oxygen concentration during synthesis. The reduction of the higher oxide's advantages include that it is more straightforward experimentally, and provides better insight into the effect of temperature gradients in governing the nucleation and growth of the nanowires.

Specific examples of the two approaches include the synthesis of ZnO and $SnO_2$ nanowires, although, as explained, there are other alternatives. To produce zinc oxide, an alumina boat that holds the zinc powder within a quartz tube was placed horizontally within a tube furnace maintained at 500° C. or above. In the absence of catalysts, growth can occur via a VS mechanism, although an oxide-assisted mechanism may also contribute. Zinc oxide nanoforms may be collected downstream from plates positioned at lower temperature regions. Nanowires, nanoblades, or tetrapods may be formed depending upon the details of the furnace temperature, gasflow rate and temperature of the collection zone. To produce tin dioxide, SnO powder was similarly held within an alumina boat, but evaporated species formed nanowires within the same boat at temperatures of ~800° C. Nanowires formed along the boat edges and on the surface of the source material. Alternative approaches can include carbothermal reduction of the oxide mixed with powered graphite in either volumetric or molar ratios of 1:1.

In controlled oxidation, one-dimensional nanoelements can be formed from metal foils, films, wires, etc. These can be used in situ, as synthesized or harvested for subsequent processing. Potential oxidants can include $CO_2$, $H_2O$, or $O_2$. Mixtures and combinations of reducing and oxidizing agents can be easier to formulate if single-source precursors are used. Although referred to as controlled oxidation, the term is a bit of a misnomer, as overall reducing conditions can also result in nanowire formation, particularly with single-source precursors. Concentrations are critical and often only trace levels (<0.1 percent) may be sufficient. The temperature range can be mild, extending from ~400 to 600° C. for most materials. A large variety of starting materials can yield highly variable results. To be expected, temperature and reactant gas concentrations are critical to not only realizing nanowire growth, but also the morphology. Higher yields can be obtained through a variety of means, including preconditioning the metal substrate by either oxidation and/or reduction or by preapplication of catalyst particles. No specific experimental setup is required, as a variety of configurations can be used, ranging from tube furnaces to open flame to even laboratory bench hot plates.

As synthesized, the intimate nanowire attachment to the substrate requires energy-intensive processes such as ultrasound to facilitate their removal. In some cases, even mechanical action may be necessary. In such cases, considerable debris can be produced, often firmly bonded to the nanowires. An analogy is pulling a plant from the soil, yielding stem and roots with a clump of dirt still attached. Time-intensive gravitational sedimentation in conjunction with surfactants can aid separation of nanowires from particles or other ill-defined debris, but only if these are not physically bound together.

Figure 10:
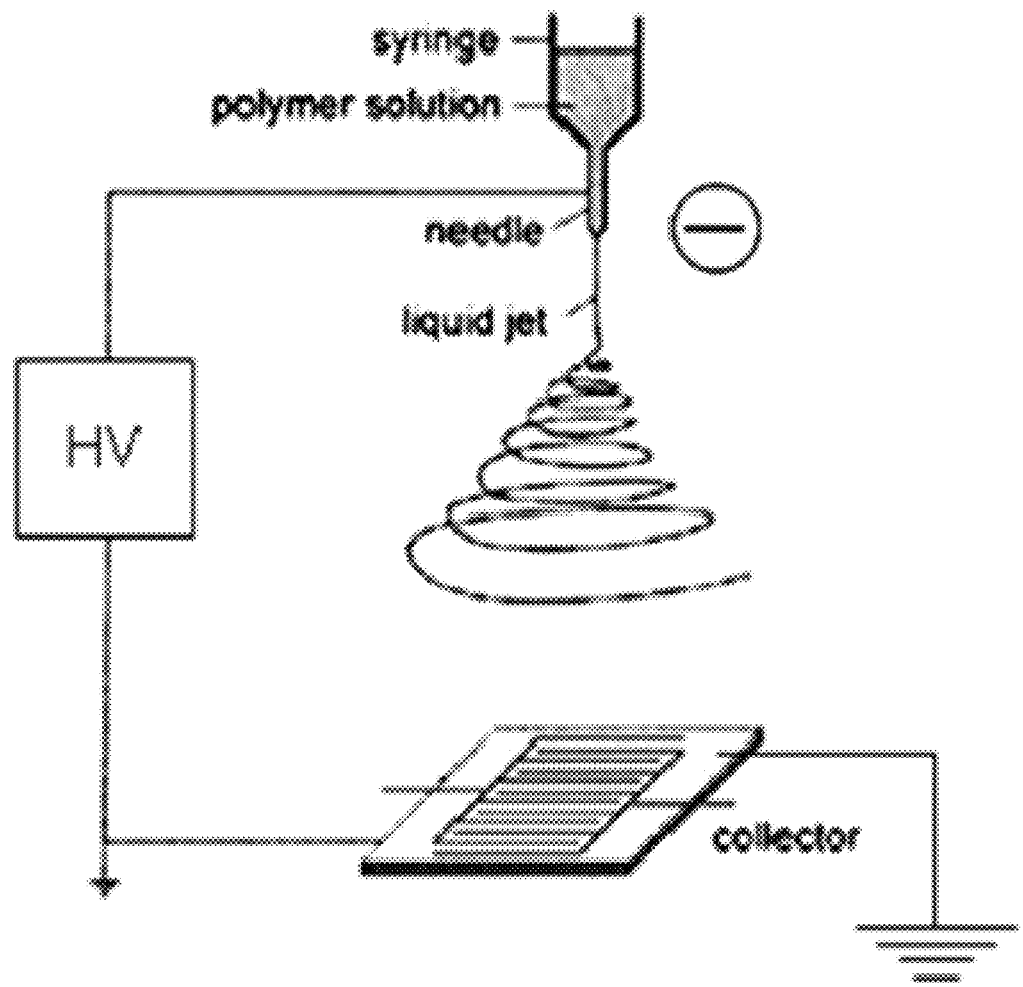
FIG. 10 illustrates an experimental setup useable to form nanostructures by means of electrospinning.

FIG. 10 illustrates an experimental setup useable to form nanostructures by means of electrospinning. Electrospinning is a process in which a high voltage is used to draw a thin filament of solution from a needle to a ground plane (in the experimental results discussed below, the sensor array). The needle can deliver the thin fluid stream from a reservoir aided by either mechanical or gas backing pressure. During the drawout process, the nanofiber is observed to whirl about the axis between the needle and substrate, hence the name electrospinning. As the fiber traverses the distance between the needle and substrate, solvent evaporates yielding a semi-solid nanofiber. The viscosity of the solution can be critical to its streaming from the nozzle in the form of a continuous filament rather than emerging as a spray. The composition of the spun filament can be determined by the precursors used. In the experimental results discussed herein, a polymer solution was used as a binder for a metal-oxide sol-gel solution. Upon calcination, the polymer was oxidized and the resulting sol-gel was solidified to form a metal-oxide, polycrystalline nanofiber.

Typically, in the electrospinning process, a mixture of metal alkoxide and polymer was used as the precursor mixture. These solutions were fed by a syringe pump to an electrified 22-gauge needle from which a filament emerged under the action of high negative voltage (15 to 20 kV) between the needle and sensor pattern serving as the ground electrode. Typical distances between the sensor pattern and needle ranged from 15 to 30 cm.

Harvesting and Integration

Different methods have been used to incorporate nanowires and nanofibers into sensing platforms. A prior requirement for reproducibility and reliability is harvesting and purification. A brief description of these processes as applied to nanostructures from each synthesis method follows next.

After synthesis, oxide materials were collected from the deposition substrate or boat and dispersed within a liquid for subsequent deposition upon the sensor interdigitated pattern. Initially an alcohol (e.g., methanol and ethanol) or acetone was used as the suspending medium. Subsequently, dimethylformamide (DMF) was found to form a better dispersion of metal-oxide nanowires and also proved compatible with subsequent dielectrophoresis. As explained above, proper selection of photoresist and suspension medium concentration can also be used in accordance with embodiments of the subject innovation. Using a pipette, a droplet of the suspension was placed upon a sensor pattern.

Nanowires were removed from their substrates by placing them in a small beaker with approximately 1.5 mL of solvent and sonicating for 1 hour. The sonication process removed nanowires as well as irregular-shaped particles that were undesirable. As was the case for TEC formed nanowires, DMF served as the suspending medium for metal oxides.

After sonication, the suspension sat for several hours, allowing large particles to settle. Particles with smaller aspect ratios also appeared to settle more rapidly, allowing small irregular-shaped particles to be separated from the nanowires as well as the large irregular-shaped particles. A decantation process was used to remove the irregular-shaped particles. Using a pipette, the remaining suspension was decanted from the beaker and placed in a narrow cylindrical vial. The narrow vial enhanced separation. The vials were placed in a secure holder and small samples of the suspension were removed periodically. The samples were inspected using an optical microscope to gauge purity. The suspensions were allowed to settle until there was a significant percentage of nanowires present.

Initial tests utilized nanostructures on a larger interdigitated electrode pattern with millimeter size gaps. Such electrode spacing was not compatible with dielectrophoretic alignment or an E-field induced torque, given the required field strengths. Initial integration of nanowires upon such patterns was performed by simple wet dispersal.

Basically, a suspension of nanowires was applied to the pattern and allowed to dry naturally. Dispersions were observed to be reasonably homogeneous without clumping. The drying process did not appear to redistribute the material, a fact attributed to the hydrophilic nature of the oxide nanowires and substrate. Hydrogen bonding likely occurred between both materials given both oxide surfaces were populated by hydroxyl groups. Electrical continuity was established by multiple bridging nanowires.

A significant feature of electrospinning is that a linear one-dimensional nanofilament is formed during the deposition process. This filament formed multiple bridges between the electrical contacts. Given the charged nature of the polymer solution, the nanofilament had a tendency to repel itself. This feature, combined with the formation of an image charge upon the electrodes filament, aided in the alignment of the fiber as roughly parallel strands formed between opposing electrical contacts. Upon calcination, the polymer was oxidized and the resulting sol-gel was solidified to form a metal-oxide, polycrystalline nanofiber. This structure served as the polycrystalline, one-dimensional sensor element to be compared with the one-dimensional single-crystal nanowires as formed by the TEC approach described previously.

As explained above, for the purposes of alignment, dielectrophoresis is a process applicable to a range of nanoscale morphologies including nanorods, particles, and branched structures. It can be applicable to nanowires and even nanofibers were they broken and dispersed into a suitable suspending medium (though this negates the direct deposition advantage of electrospinning). Dielectrophoresis relies upon the difference in dielectric constant of the suspending fluid medium and suspended material. Dielectrophoresis is distinct from electrophoresis, wherein charged particles migrate under the action of an applied field by virtue of electrostatic attraction or repulsion. Under the action of an applied electric field, material may either be drawn into or repelled from a region of high electric field by a force proportional to the gradient of the E-field. Notably, it may be applied in either DC or AC fashion. Dielectrophoresis can work with a range of nanostructure compositions, including carbon nanotubes (CNTs) and oxide materials. CNTs require additional considerations during dielectrophoresis, given their high self-adhesion and tendency towards clumping.

Polarization charges can be induced upon the nanowires and the resulting dipole interacts with the E-field gradient, as given by equation 1, reproduced here, $$F_{dep} = (p(t) \cdot \nabla) E(t) \quad (1)$$

where, as explained above, $F_{dep}$ is the time-dependent force in an AC field, $E(t)$ is an electric field, and $p(t)$ is the dipole.

Expansion of the induced dipole terms reveals the dependence upon the nanowire dimensions, difference in the dielectric constant between the nanowire and suspending medium, and electric field gradient. The expansion is given by equation 2, reproduced here, $$p(t) = 4\pi \in_m l r^2 Re(K_a) \nabla |E_{rms}|^2 \quad (2)$$

where, as explained above, $\in_m$ is the permittivity of the suspending medium, l and r are the length and radius of the nanowire respectively, and $E_{rms}$ is the root mean square of the electric field. The Ka factor depends on the complex permittivities of both the particle and the medium.

Dielectrophoresis can indirectly induce alignment if electrodes are designed to create an E-field gradient perpendicular to their gap. Such a gradient can be created depending upon electrode geometry, such as is the case for opposing electrodes with irregular geometries such as sawtooth or castellation patterns. As is shown by the above equations and accompanying discussion, for dielectrophoresis, the gradient is the driving force. For anisotropic nanoparticles, particularly for nanowires, the differential hydrodynamic drag force dictated by their extended aspect ratio can cause alignment. This is analogous to a log being pulled upriver. A concurrent indirect alignment mechanism is due to a torque induced within an AC electric field, as expressed by equation 7, $$\vec{T} = \vec{p} \times \vec{E} \quad (7)$$

where T is the torque vector, p is the dipole vector, and E is the electric field vector. The same induced charges can establish an induced dipole vector that seeks to align with the AC field to reach a minimum potential energy. Any slight angle between the nanowire and the E-field vector can result in differential forces on each end and the dipole vector p can align along the E-field vector E. Dielectrophoresis can then complete the integration of the nanowire to bridge opposing electrodes.

In the experiments discussed below, dielectrophoresis was used to align the nanowires produced by TEC and controlled oxidation to bridge the electrodes within the sensor pattern. The electrodes were arranged in an interdigitated comb pattern. An AC voltage was applied across the electrode grid using a function generator. For nanowires less than 10 µm long, 10 V AC at a frequency of 5 MHz was applied. For nanowires greater than 10 µm long, a lower frequency was used because it improved alignment. For example, lowering the frequency from 5 MHz to 500 KHz appeared to improve the alignment of $SnO_2$ nanowires that had a length greater than 20 µm long.

The suspending medium (typically DMF or a light alcohol) was allowed to evaporate with the voltage applied to the grid during this process. The resistance across the grid was measured after the solvent completely evaporates. Typically, a measurable resistance (less than 40 MΩ) was found after four drop/evaporation cycles were completed. After each deposition step, the nanowire placement on the interdigitated grid was observed using an optical microscope to verify deposition uniformity of nanowires.

Charge carrier density and energy levels may be adjusted by doping of heteroatoms into the band structure. Differences in charge state upon incorporation into the lattice matrix can either add to or be subtracted from the carrier charge concentration. Moreover, such atoms may also alter the reactivity of the exposed surface lattice structure apart from carrier density or energy levels by exerting a catalytic action. Generally, elements with valencies +1 or −1 relative to that of the main cation can be used to introduce either electrons (for n-type materials) or holes (for p-type materials). A consideration with this approach is that the primary effect is an increase in carrier concentration, second is higher carrier mobility, and third, though the primary motivation for doping, is reactivity. Lattice strain due to heteroatom doping can increase reactivity and hence sensitivity. As an alternative, metal nanoparticles may be formed independently from the nanowire synthesis and subsequently deposited via either physical vapor deposition or wet-chemical processes.

This discrete nanoparticle coating can permit exposure of the underlying metal oxide support and most importantly can create numerous interfacial junctions between the particle and support oxide. These junctions can be self-polarized by virtue of charge transfer due to differences in the metal work function and electron affinity of the semiconductor. This interface can be expected to be highly reactive for well-crystallized metal nanoparticles as the adsorbate is exposed to a polarized interface (Schottky junction) resembling a step or terrace upon single-crystal catalytic metals.

This approach has been used in catalysis where the noble metal nanoparticle and/or the interfacial region between the particle and oxide support greatly accelerates the reaction compared to the bare oxide surface. In the experiments discussed below, metal nanoparticles were created by sputter deposition to an effective film thickness of 0.5 nm as monitored by a quartz crystal film thickness monitor. Deposition was performed under argon at 10 mtorr using the appropriate metal target.

Comparisons Between Synthesis Methods

Nanostructured materials have a wide range of uses, for example, gas sensing, photodetection, etc. The results included herein compare varied materials, crystal structures, and morphologies. Direct comparison between these parameters provides a starting point for nanostructure integration into practical devices. Limitations and advantages of the synthesis methods discussed herein and associated implications for material integration are summarized below. As explained further below, these considerations have implications for the application of nanostructure in a variety of setting.

Synthesis via TEC approaches was highly sensitive to temperature and gas-phase transport processes; precise control of the morphology was very difficult to achieve. Given sensitivity to conditions and strong temperature dependence of the vapor generation and subsequent crystallization, doping of heteroelements is not controllable. Synthesis requires high temperatures, necessitating separate growth apart from substrate or other device architecture followed by redispersal and attachment for fabrication. Redispersal with alignment presents challenges. Techniques such as dielectrophoresis have demonstrated only partial success with specially designed electrode configurations. While the nanowires present uniform crystalline surfaces, the single-crystalline structure is actually less ideal for chemisorption than a polycrystalline one. Defect sites in the form of oxygen vacancies are, in principle, absent. Only via irregularities in the growth process are such sites created. Hence chemisorption on single-crystalline planes is less than that on a polycrystalline one. As a single-crystal combined with a relative lack of defect sites and associated chemisorption, conductance can be very low with the consequence of difficult impedance matching.

For controlled oxidation, orientation, placement, and density of nanostructures can be difficult to control, although pre-patternation can be advantageously used. Upon harvesting, high contamination can result, requiring extensive purification, generally with limited success. Diameters and lengths of the nanowires tend to be limited (<5 µm) in this growth process. Product morphology (e.g., nanowires versus nanoblades) can be highly dependent not only upon process conditions but also metal grain structure, pretreatment (including ambient exposure), and other subtleties such as furnace tube condition and trace gas composition.

Turning to electrospinning, within the polycrystalline fiber, there can be different degrees of overlap between grains. Although composed of nanocrystals, the nanofiber may be susceptible to sintering and resulting grain growth during operation. Sintering between grains may occur during calcinations resulting in "necks" between grains that remain isolated and provide a large independent resistance. The surface possesses a variety of adsorption sites (associated with different crystalline facets) with different energies resulting in a potential lack of sensitivity and selectivity towards chemisorption at these sites. It can require calcinations subsequent to deposition upon device.

Several consideration can be related to fabrication, including the adherence of the nanofiber to the contact pads and required expertise to obtain correct viscosity of the polymer-sol gel solution as the electrospun solution.

The single-crystalline structures obtained via TEC can offer 100 percent improvement in lifetime by resistance against the sintering, which can cause sensor drift. The manner by which the nanostructures react with the chemical species is uniform and controllable. This reflects the fact that the single-crystal nanowires expose well-defined crystalline planes. Hence the nanowires can adsorb oxidizing or reducing gases in a uniform fashion, as opposed to polycrystalline films, whose response mechanism can be highly dependent upon the grain boundaries crystal structure, film porosity, etc. While an optimization analysis could be applied to weigh these advantages and disadvantages to determine the optimal choice, the assignment of weighting factors would be arbitrary at best. Thus, depending on particular applications, some of the relative advantages and/or disadvantages may be more relevant than others.

Direct metal oxide nanowire growth by controlled oxidation can be possible upon a variety of foils, films, wires, and other pre-patterned metal deposits. Controlled oxidation offers the capability to grow materials not readily accessible via other conventional methods, for example, TEC. In particular, refractory oxides such as $Fe_2O_3$, $WO_3$, $NbO_2$, $TiO_2$, etc. can be readily fabricated. Nanowires including iron and nickel and copper and tin can also be fabricated. This synthesis method can also be integrated with microfabrication methods producing thin films, traces, and other pre-patterned areas as growth temperatures are mild by comparison to those required for CNT synthesis.

Electrospinning does not involve sensitive gas-phase transport processes and temperature-dependent crystallization. Composition control can be readily achieved by using different (e.g., metal oxide) precursor mixtures. A metal oxide nanofiber can easily be directly placed and/or aligned upon prefabricated contacts. Although a polycrystalline fiber, a nanofiber created via electrospinning does not have the irregular surface features of a film. The polycrystalline defect structure provides a greater number of reactive sites for chemisorption compared to single-crystalline material.

Despite the heterogeneity, the polycrystallinity of the nanofiber offers a higher concentration of charge carriers (electrons for n-type material). This lowers the baseline resistance, potentially aiding sensitivity and lowering operation temperature. Additionally, the polycrystallinity may offer enhanced reactivity, further aiding sensitivity.

Experimental Results

Figure 11:
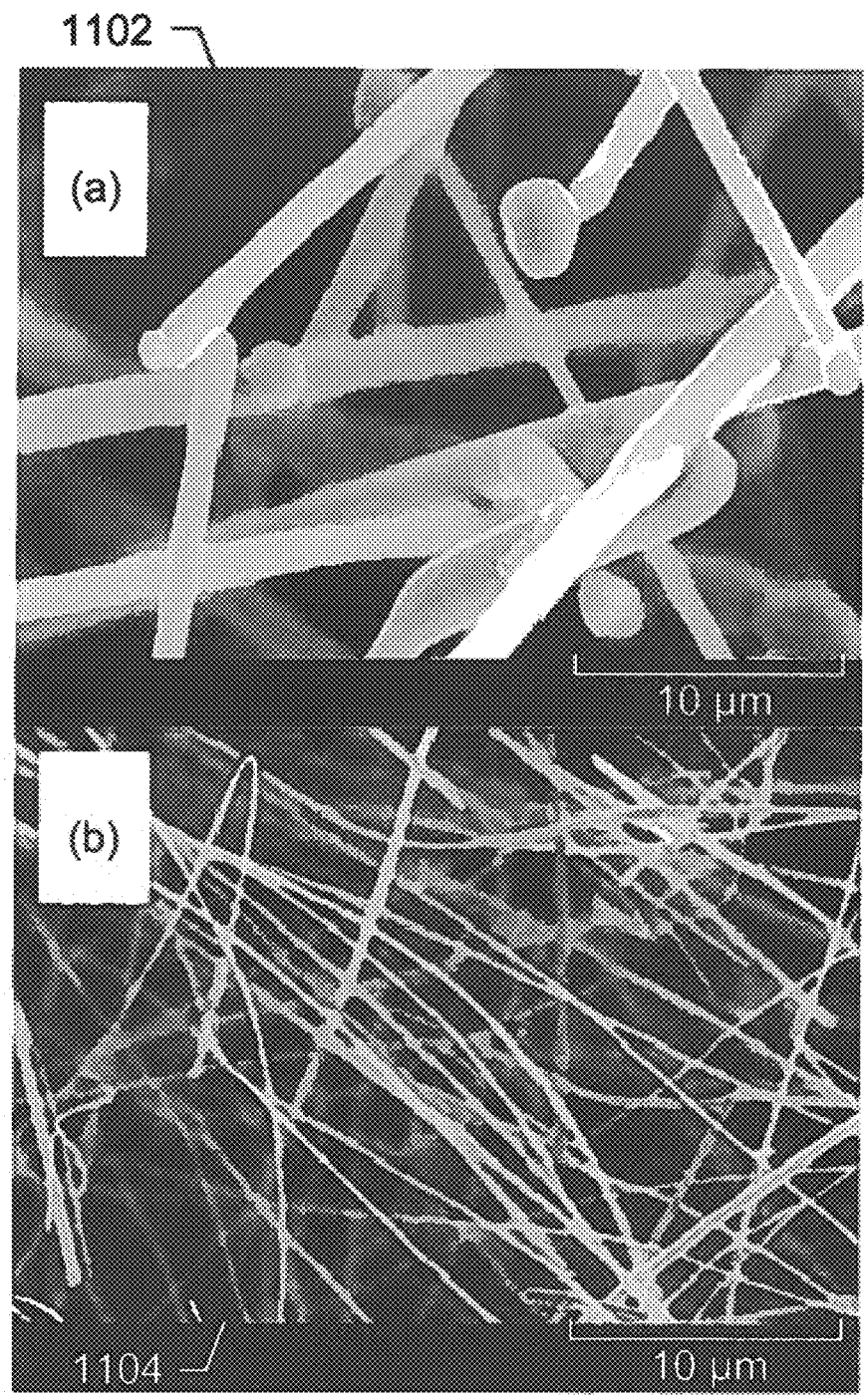
FIG. 11 illustrates SEM images of single-crystal $SnO_2$ nanowires obtained by the VLS mechanism and the VS mechanism.

FIG. 11 illustrates SEM images of single-crystal $SnO_2$ nanowires obtained by the VLS mechanism at 1102 and VS mechanism at 1104. TEC processes have been developed for the nanoscale materials of the semiconducting oxides. Metal oxide and other semiconductors have been synthesized through both VS or VLS mechanisms, similar to the $SnO_2$ nanowires shown in FIG. 11.

Common to the TEC process is the generation of a vapor phase precursor species using one of two approaches: reduction of the higher oxide and oxidation of the base metal. Each approach possesses advantages and limitations as discussed previously. In either case, a substoichiometric oxide vapor can be produced at elevated temperature by reduction of a precursor (higher) oxide or by partial oxidation of the nascent metal.

Through self-assembly, as guided by flow and temperature gradients, the metal-oxide vapor forms the nanostructure via the VLS and VS process. The former relies upon catalyst particles to form a eutectic mixture with the metal oxide while the latter represents direct crystallization of the metal oxide nanostructure from the gas-phase. Examples for $SnO_2$ nanowires are shown in images 1102 and 1104, respectively. Image 1102 shows scanning electron microscope (SEM) images of $SnO_2$ nanorods with Au catalysts at the tips. By definition, nanorods formed via the VS process do not contain catalyst impurity, as illustrated in image 1104. These two processes (VLS and VS) proceed with different growth rates. The prime advantage of controlled nanostructure growth rate is that growth may be regulated between thermodynamic versus kinetic control. The former (thermodynamic) describes growth as regulated by the surface energies of different exposed crystalline faces. The latter (kinetic) describes growth as governed by the rate of reagent supply.

Figure 12:
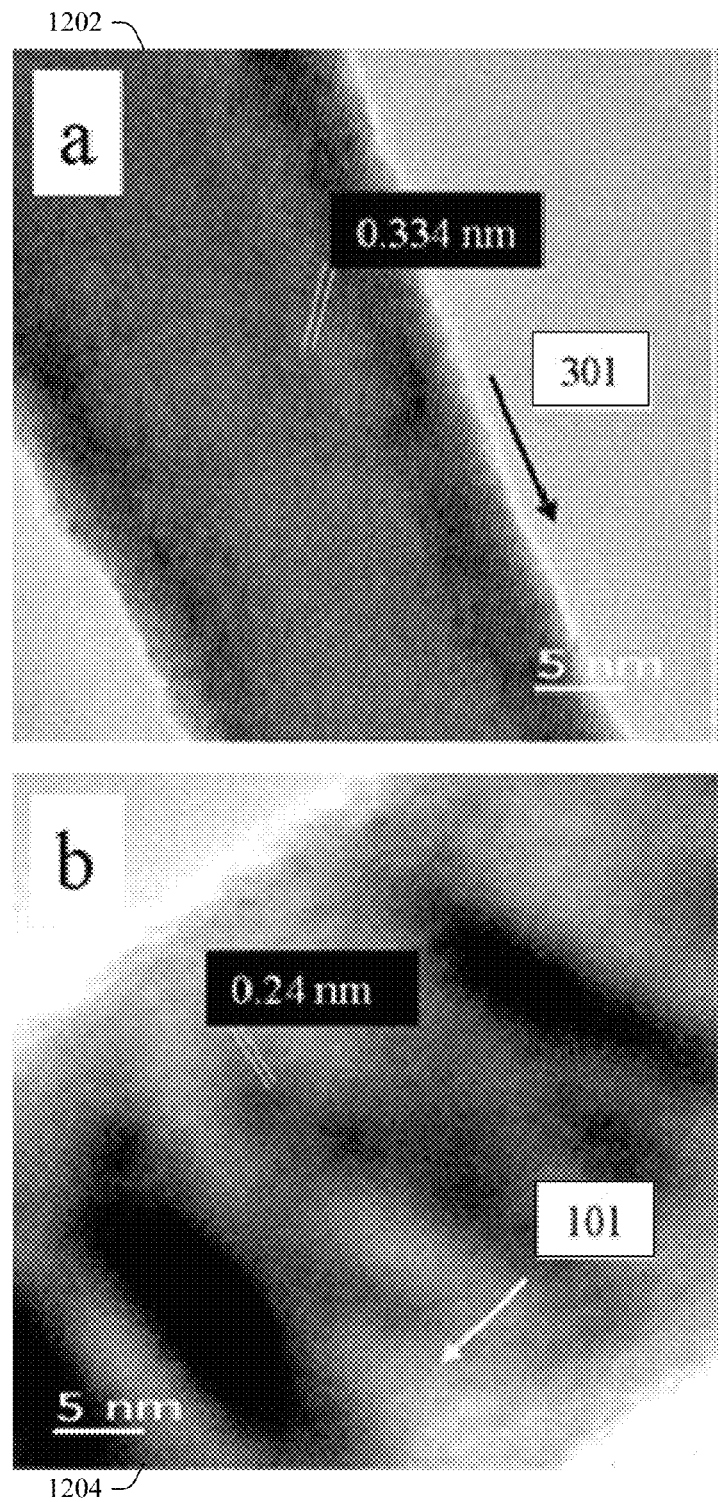
FIG. 12 shows high-resolution transmission electron microscopy (HRTEM) images illustrating the above differences for the $SnO_2$ nanowires formed via the VLS mechanism and the VS mechanism.
Figure 13:
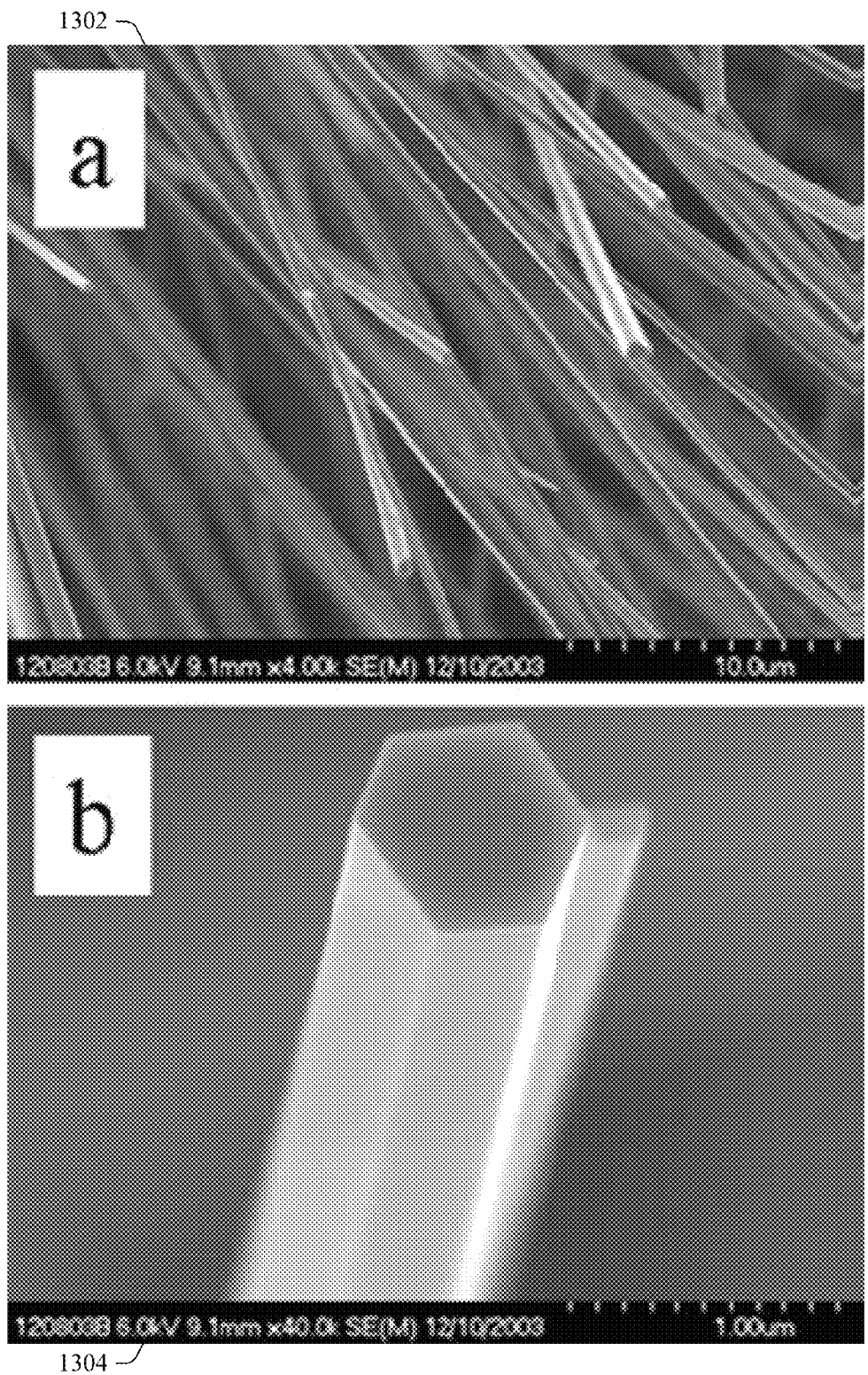
FIG. 13 shows single-crystal ZnO nanowires in low resolution and high resolution.

FIG. 12 shows high-resolution transmission electron microscopy (HRTEM) images illustrating the above differences for the $SnO_2$ nanowires formed via the VLS mechanism at 1202 and the VS mechanism at 1204. The boxed numbers inside the images are Miller indices, indicating crystal planes. While thermodynamic control can lead to the most energetically favorable structure, kinetic control can permit growth along different (non-equilibrium) crystalline facets. Control via either mechanism can permit uniform growth rates that can be used to optimize crystalline structure and eliminate grain boundaries and crystalline defects. Highly crystalline materials result. This is particularly well illustrated for more complex crystallographies, such as the wurtzite structure of ZnO, as illustrated in FIG. 13, which shows single-crystal ZnO nanowires in low resolution at 1302 and high resolution at 1304. The hexagonal faces visible in image 1304 clearly mark the equivalency of the surface facets with growth occurring along the c-axis.

By either method, the semiconducting metal oxide nanostructures may be grown in various geometries, for example, producing rectangular cross sections resembling nanoribbons or nanobelts as opposed to radially symmetric nanowires. Variation of the vapor supply rate, binary reagents, and/or eutectic forming catalysts can lead to more complex structures such as ferns, combs, and trees.

Figure 14:
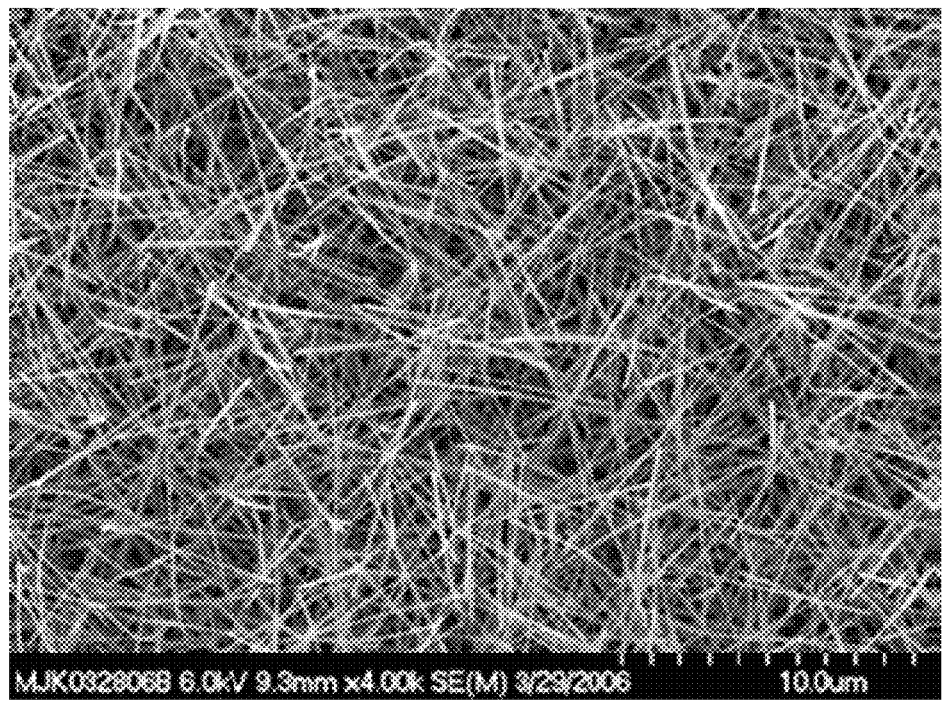
FIG. 14 illustrates $TiO_2$ nanowires grown upon Ti foil using the controlled oxidation method.
Figure 15:
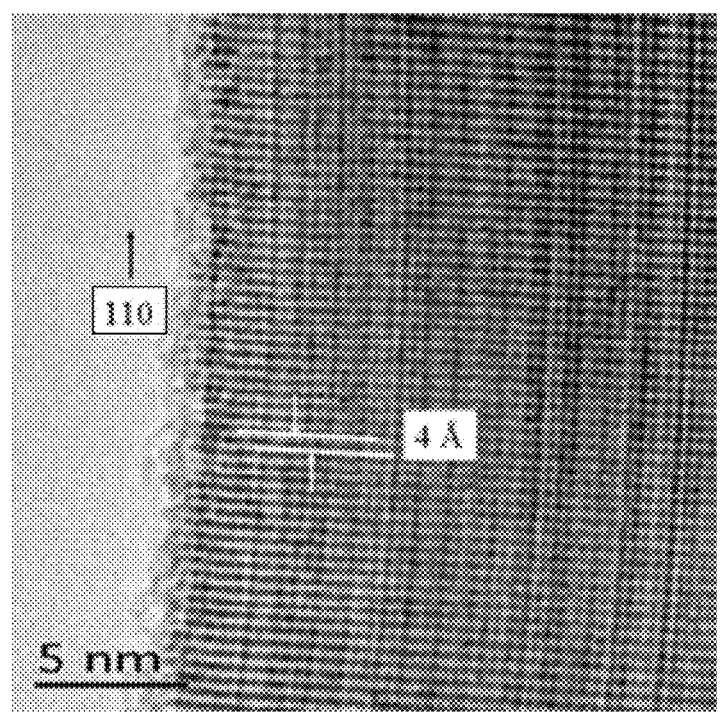
FIG. 15 shows a HRTEM image of a $TiO_2$ nanowire, from which the crystallography is readily apparent.

FIG. 14 illustrates $TiO_2$ nanowires grown upon Ti foil using the controlled oxidation method. The substrate was exposed to conditions facilitating breakup, a necessary step for synthesis. High density and morphological uniformity is apparent. FIG. 15 shows a HRTEM image of a $TiO_2$ nanowire, from which the crystallography is readily apparent. As above, the boxed number in the image is a Miller index. Nanostructures fabricated by means of controlled oxidation have many potential uses as fabricated upon the substrate, for example, solar cells. Harvesting of these materials can be difficult as they are integrally attached to the substrate. Simple mechanical methods such as doctor-blading can both break the rods and rip up chunks of substrate. Nevertheless, the method can be invaluable for nanowire synthesis of refractory metal oxides.

Figure 16:
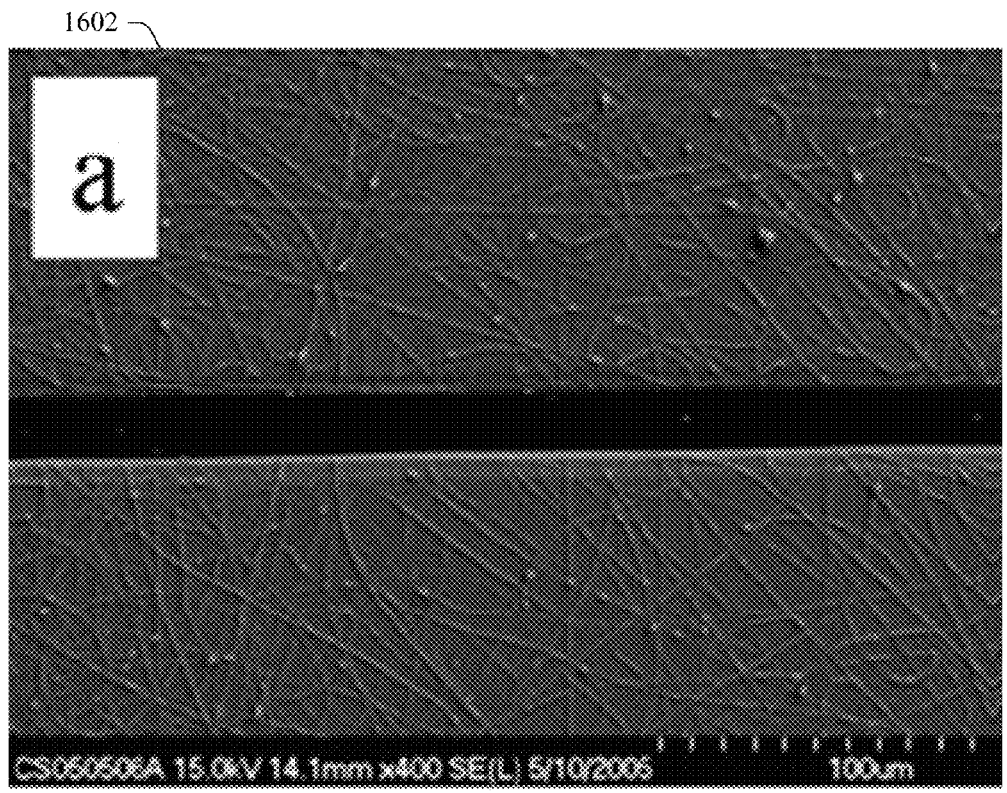
FIG. 16 is an optical micrograph of electrospun nanofibers bridging across opposing electrodes that in reflectance mode are white.
Figure 16:
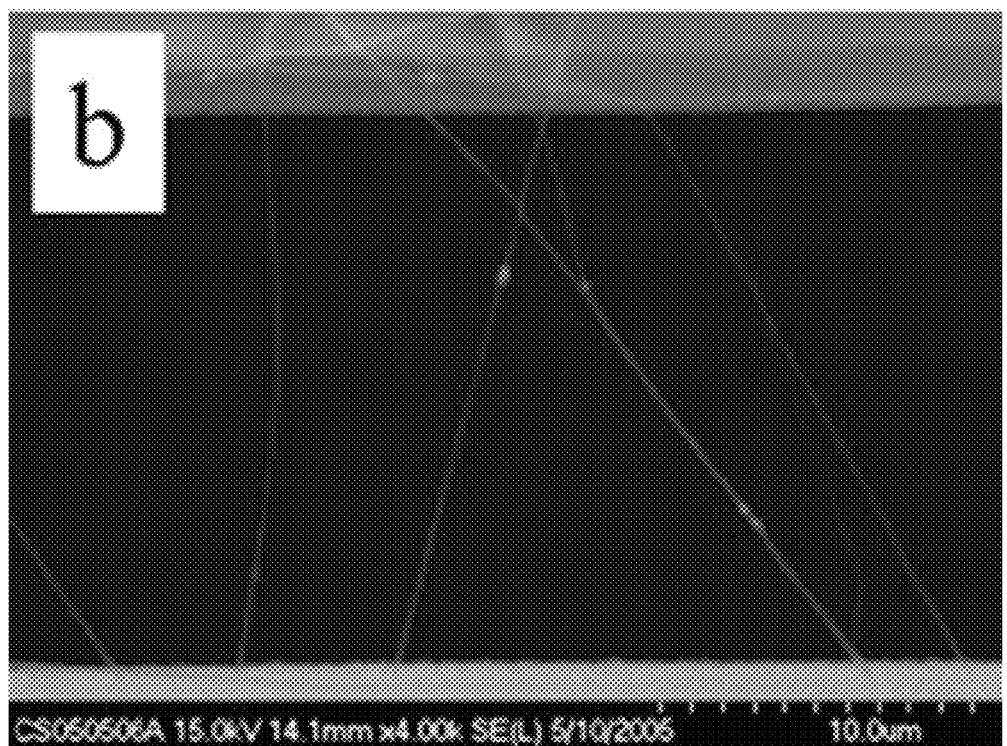
Figure 17:
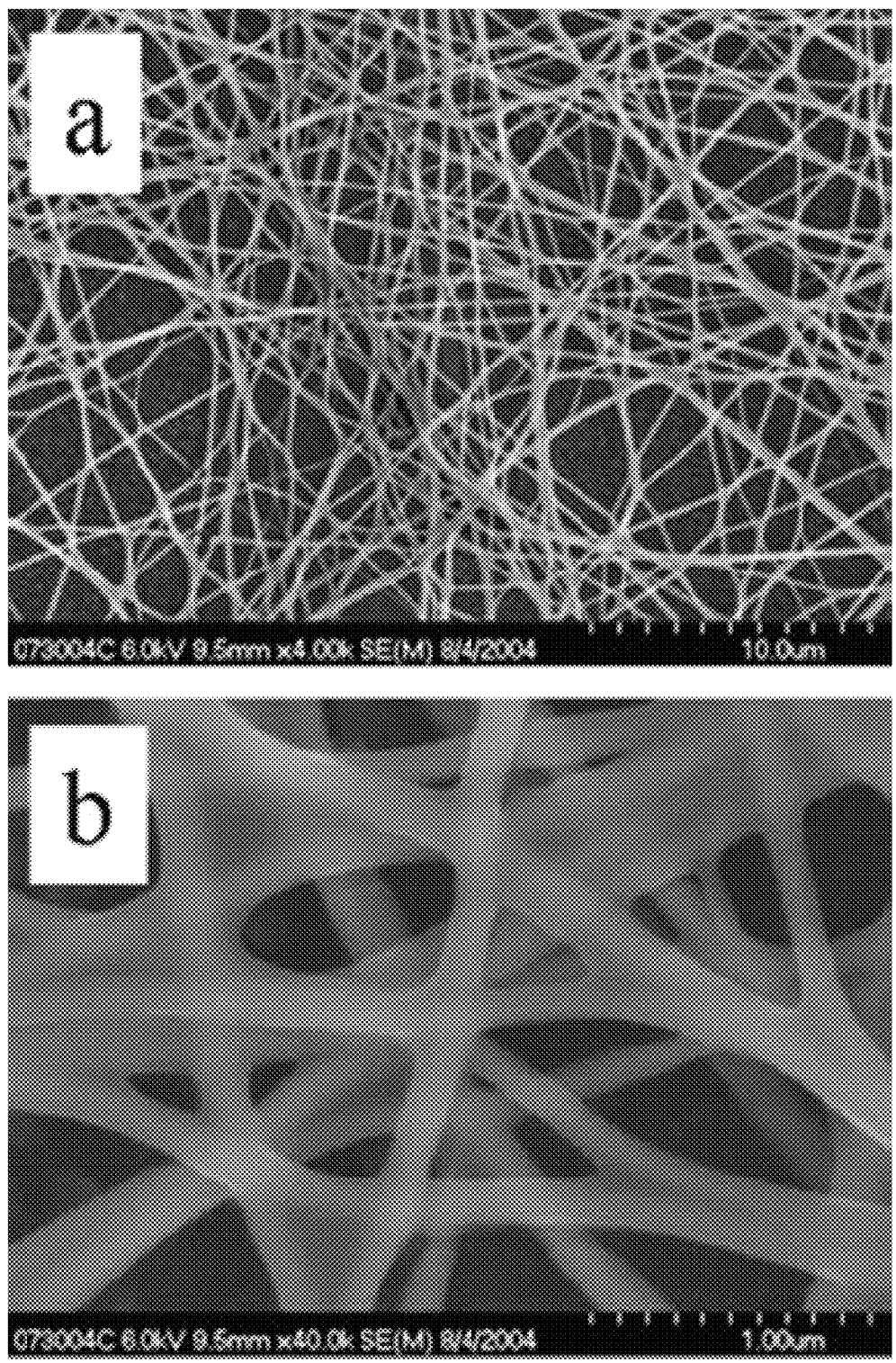
FIG. 17 shows SEM images of noncalcined $SnO_2$ nanofibers.
Figure 18:
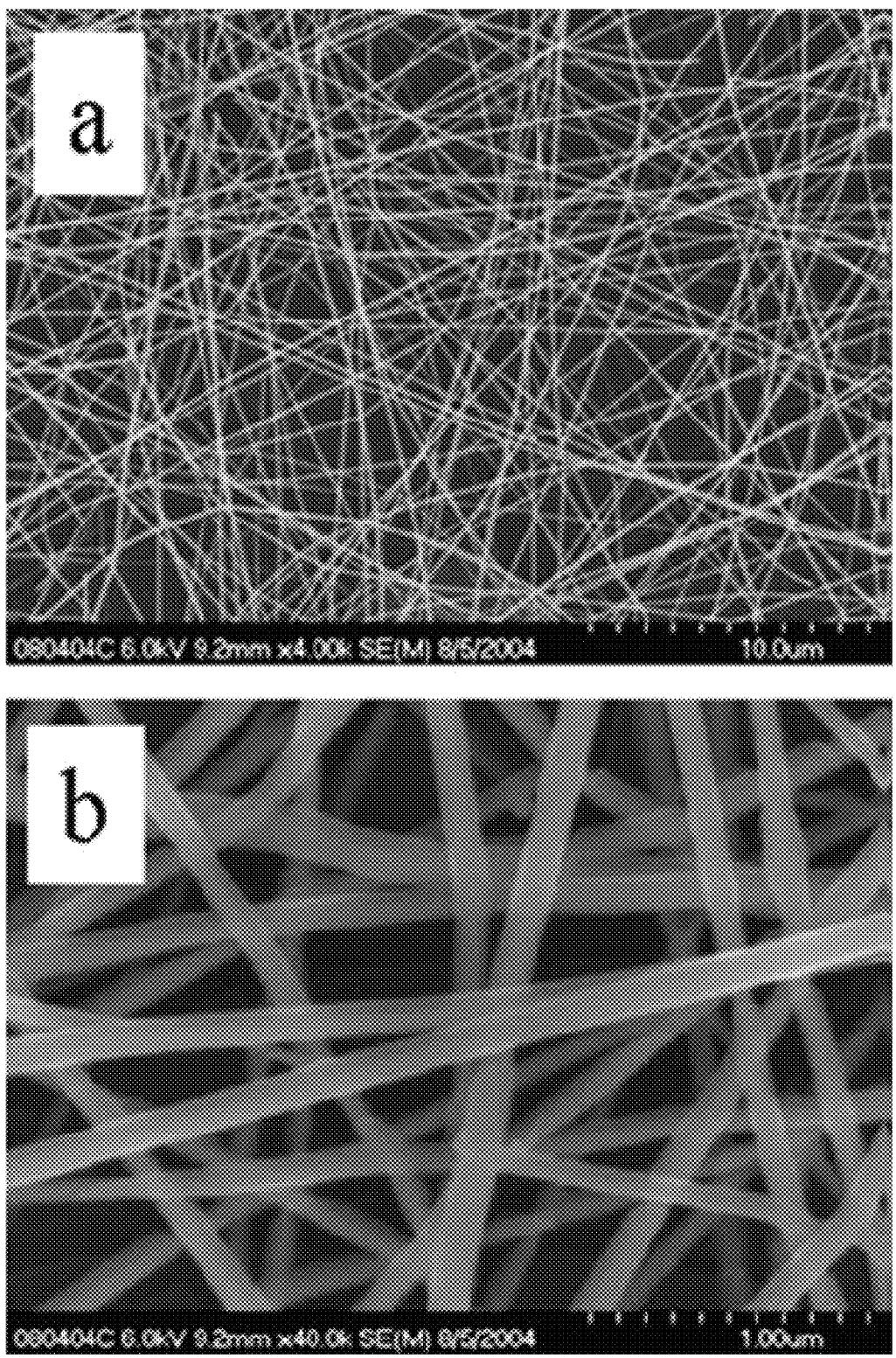
FIG. 18 shows SEM images calcined $SnO_2$ nanofibers.

FIG. 16 is an optical micrograph of electrospun nanofibers bridging across opposing electrodes that in reflectance mode are white. $SnO_2$ nanofibers were grown using the electrospinning method, and can be seen in a lower magnification image 1602 and higher magnification image 1604. The higher magnification image 1604 shows the nanofibers as "grass" with preferential alignment. Visible in images 1602 and more clearly in image 1604 are nanofibers bridging a trench in a silicon wafer. The suspended feature illustrates the mechanical integrity of the nanofibers and suggests the capability for alternative sensor geometries for monitoring flows. FIG. 17 shows SEM images of noncalcined $SnO_2$ nanofibers. An ordinary metal plate was used as the ground plane, which accounts for the intertwined nature of the nanofibers. Depending upon the deposition time, varying degrees of fill may be produced. FIG. 18 shows SEM images calcined $SnO_2$ nanofibers. Significant in FIG. 18 is the demonstrated mechanical preservation of the one-dimensional form of the nanofiber. As judged by comparison to the scale marker, the nanofibers were ~100 nm in diameter. As TEM images discussed below indicate, these nanofibers were not solid but possess many gaps and spaces between the crystalline particles comprising the nanofiber. As clearly seen by the optical and SEM images in FIGS. 16-18, the nanofibers produced by means of electrospinning were very uniform in morphology and size. This stands in stark contrast to the plethora of TEC-produced metal oxide nanostructures where only microscopic amounts possess such uniformity. Such quality control can be beneficial in defining structure-property relationships and for achieving consistent sensor response by quality control of the sensing element.

Figure 19:
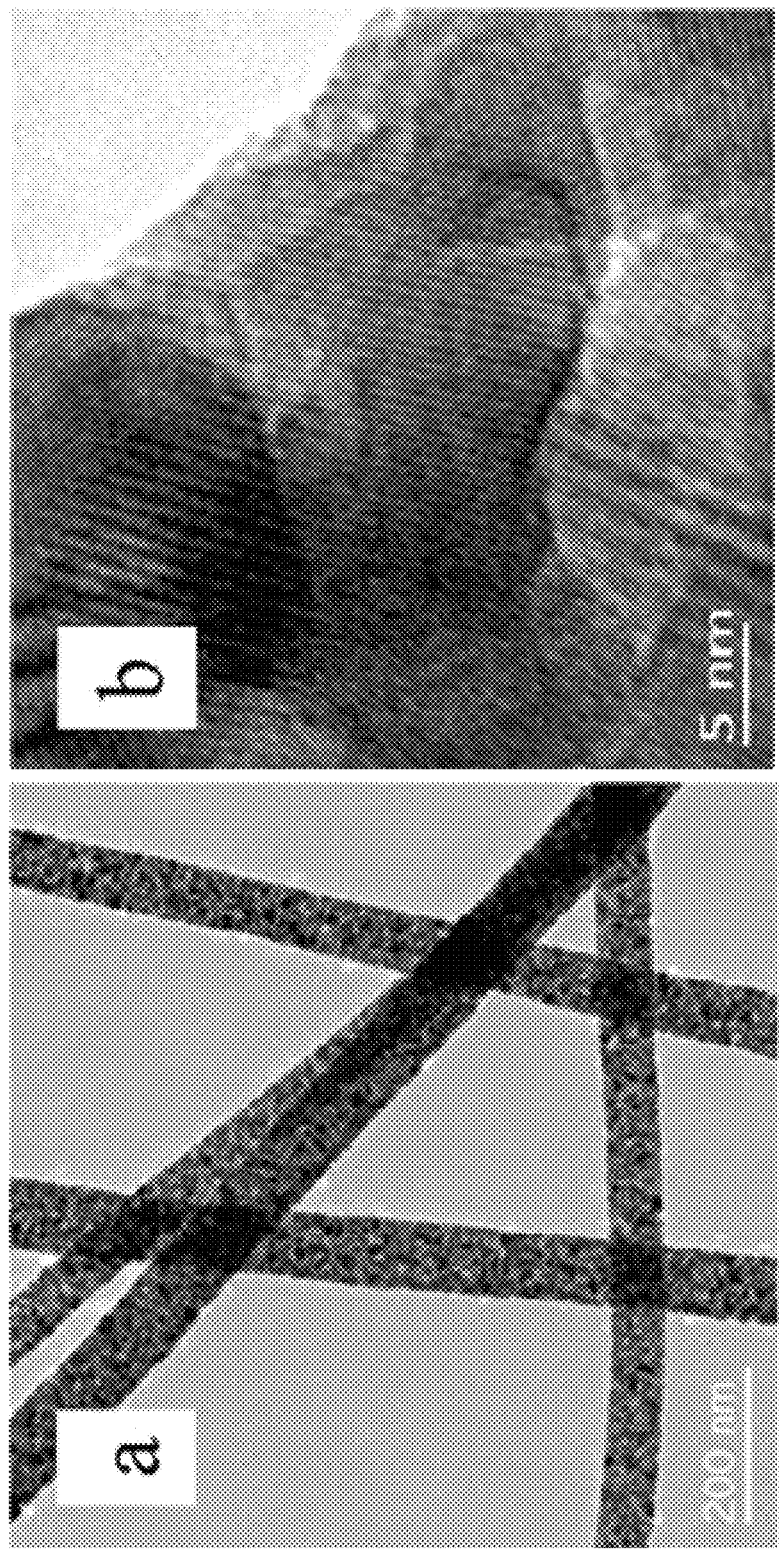
FIG. 19 illustrates TEM images of calcined nanofibers at two different resolutions, as indicated by the scales on the images.

FIG. 19 illustrates TEM images of calcined nanofibers at two different resolutions, as indicated by the scales on the images. To obtain the samples shown in the images in FIG. 19, nanofibers were removed from the substrate and dispersed upon a TEM grid. The granular structure is readily apparent from both images. The HRTEM images of FIG. 19 reveal the crystallinity of each individual grain comprising the nanofiber. Each particle was single-crystalline as indicated by the visible lattice planes in each particle. The cross-hatching apparent in some particles arises from overlaid particles with resulting multiple diffraction of the electron beam leading to a Moire effect. The integrity of the nanofiber and multiple grain boundaries, each modulated by gas adsorption, is clear from the images.

For many applications, nanowires are harvested and to obtain sufficient (macro)scale quantities, harvesting is conducted over length scales of many millimeters to even centimeters. Because of this, there is considerable potential for morphological heterogeneity. Removal from the substrate can introduce considerable artifacts. It can expose considerable undergrowth not apparent in a top-view SEM.

Figure 20:
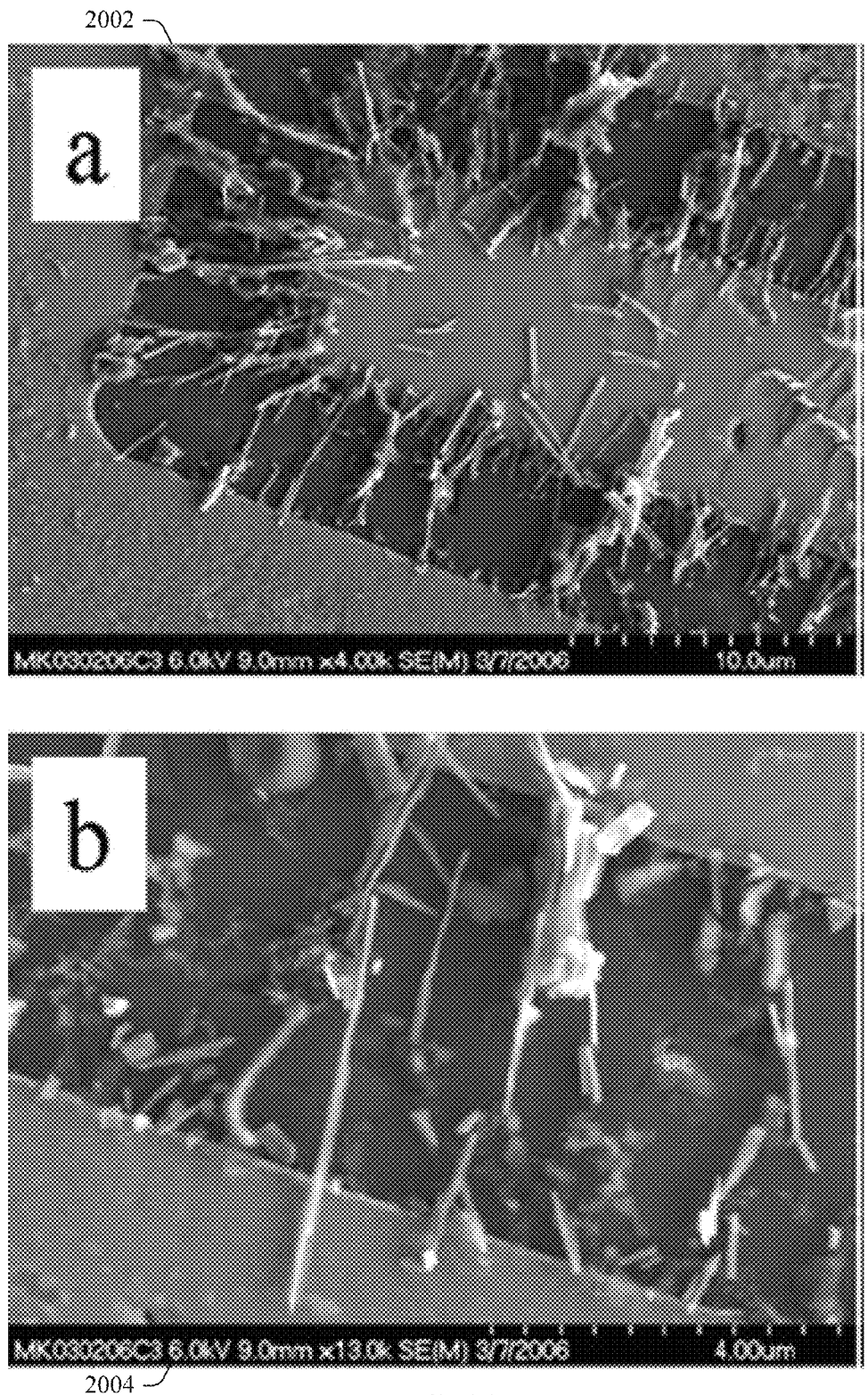
FIG. 20 shows two SEM images illustrating difficulties that can be associated with collection of nanowires.
Figure 21:
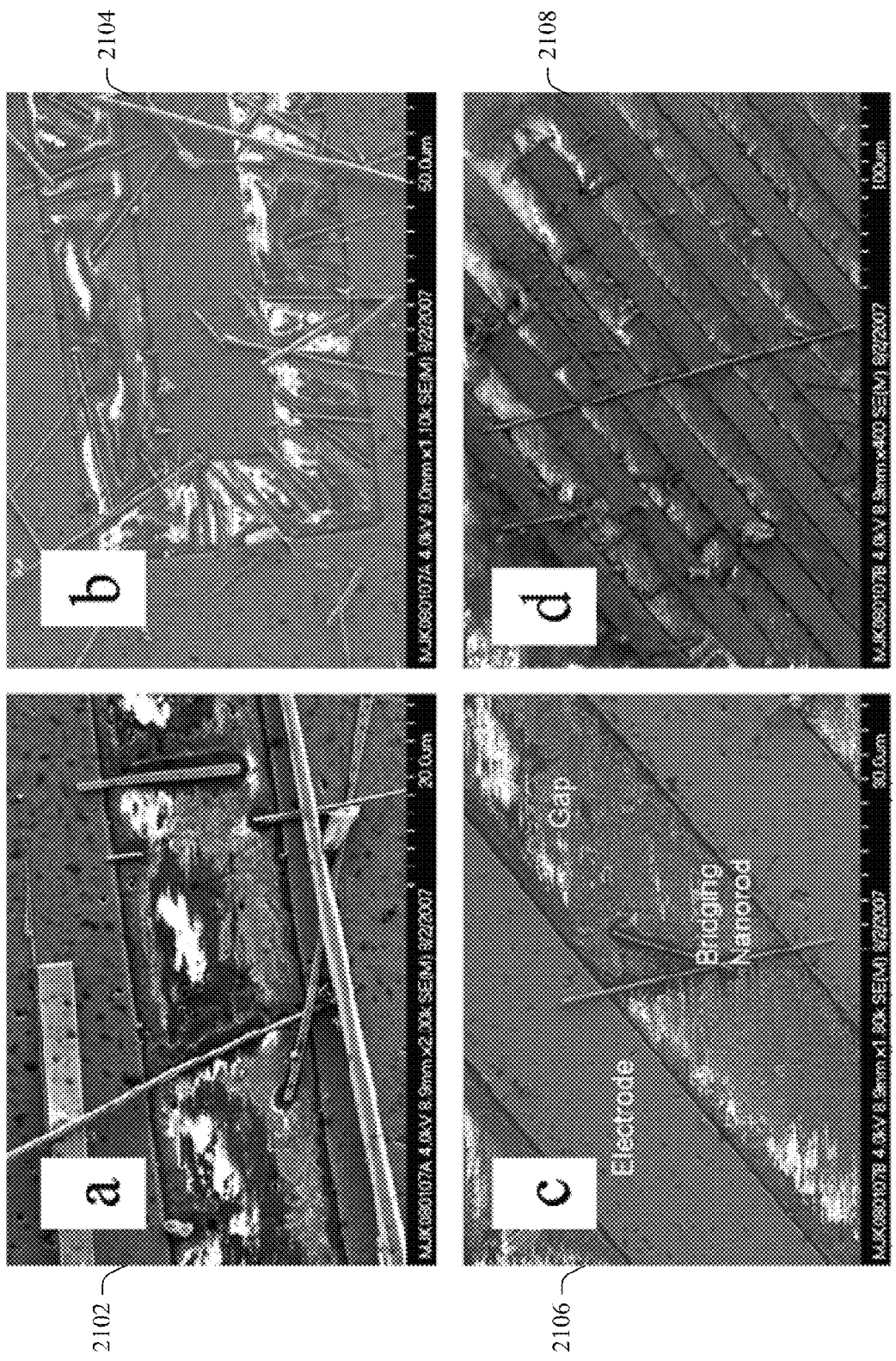
FIG. 21 shows a series of SEM images indicating the implications of varied morphologies in connection with an interdigitated electrode pattern used as a sensor platform.
Figure 22:
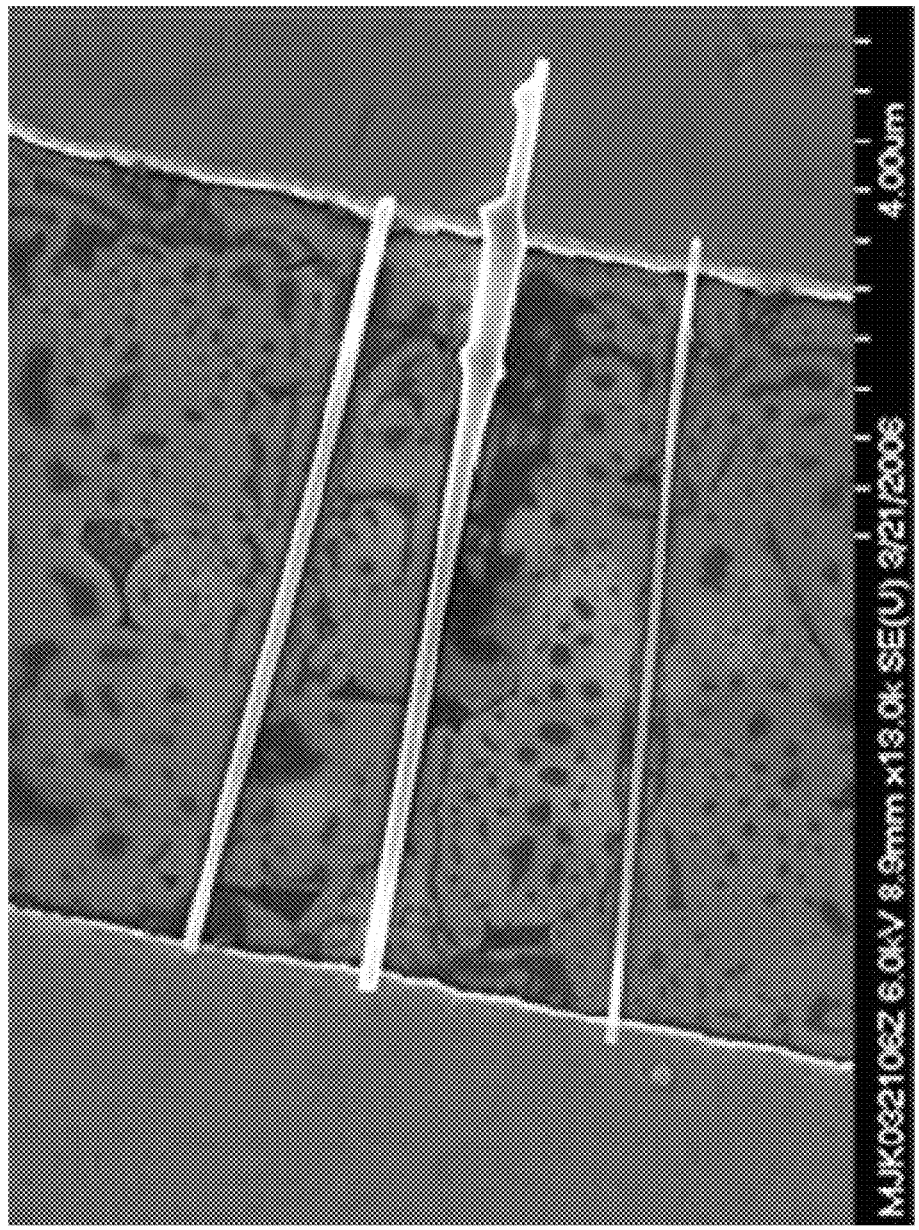
FIG. 22 shows the bridging of single nanowires in parallel alignment, with each nanowire forming individual contacts across electrodes.

Shown in FIG. 20 are two SEM images 2002 and 2004 illustrating difficulties that can be associated with collection of nanowires. Though nascent material appears homogeneous and uniform in SEM images taken prior to collection, collection can bring significant thatch. Pillars, tapered nanowires, short nanowires, and branched morphologies can all contribute to irregular contacts upon incorporation into sensor platforms. Even the removal of the nanowire from the substrate can bring a "base" comprised of substrate material. Without adequate purification, irregular objects can also be deposited. Image 2002 illustrates the varied morphologies that can be produced by harvesting nanowires grown by controlled oxidation. Image 2004 shows the unsuitability to bridge opposing electrodes of these varied morphologies. FIG. 21 shows a series of SEM images 2102-2108 indicating the implications of these varied morphologies in connection with an interdigitated electrode pattern used as a sensor platform. Images 2102 and 2104 show failure to bridge and multiple junction contacts between nanowires, image 2106 shows suspended nanowires, and image 2108 demonstrates multiple bridging by a single nanowire. In contrast to the varying morphologies and complications shown in FIGS. 20-21, FIG. 22 shows the bridging of single nanowires in parallel alignment, with each nanowire forming individual contacts across electrodes. FIG. 22 demonstrates that a combination of spatially selective and careful harvesting, along with purification, can yield vastly improved uniformity.

As is apparent from the foregoing discussion, integration entails more than simple dispersal. Using simple deposition, aggregation and pileups leading to poor contacts and multiple nanowire crossings and junctions occur, and poor contacts result. High dispersal is essential to successful integration. Congregation in regions of nonuniform E-field can result in multiple junctions and variable bridging. Nanowires may overlap, cross, and form multiple bridges across a series of electrodes if particularly long. The most common problem is the formation of overlapping nanowires that then bridge contacts. Such physical contacts between nanowires are not mechanically rigid, thereby diminishing device stability. Poor connections with electrodes may result where a nanowire by virtue of an elevation angle essentially "touches" the electrode. Apart from issues with device reproducibility, such contacts will degrade device performance over time. There is no straightforward "fix" for such irregular bridging by secondary photolithography or other processes.

Figure 23:
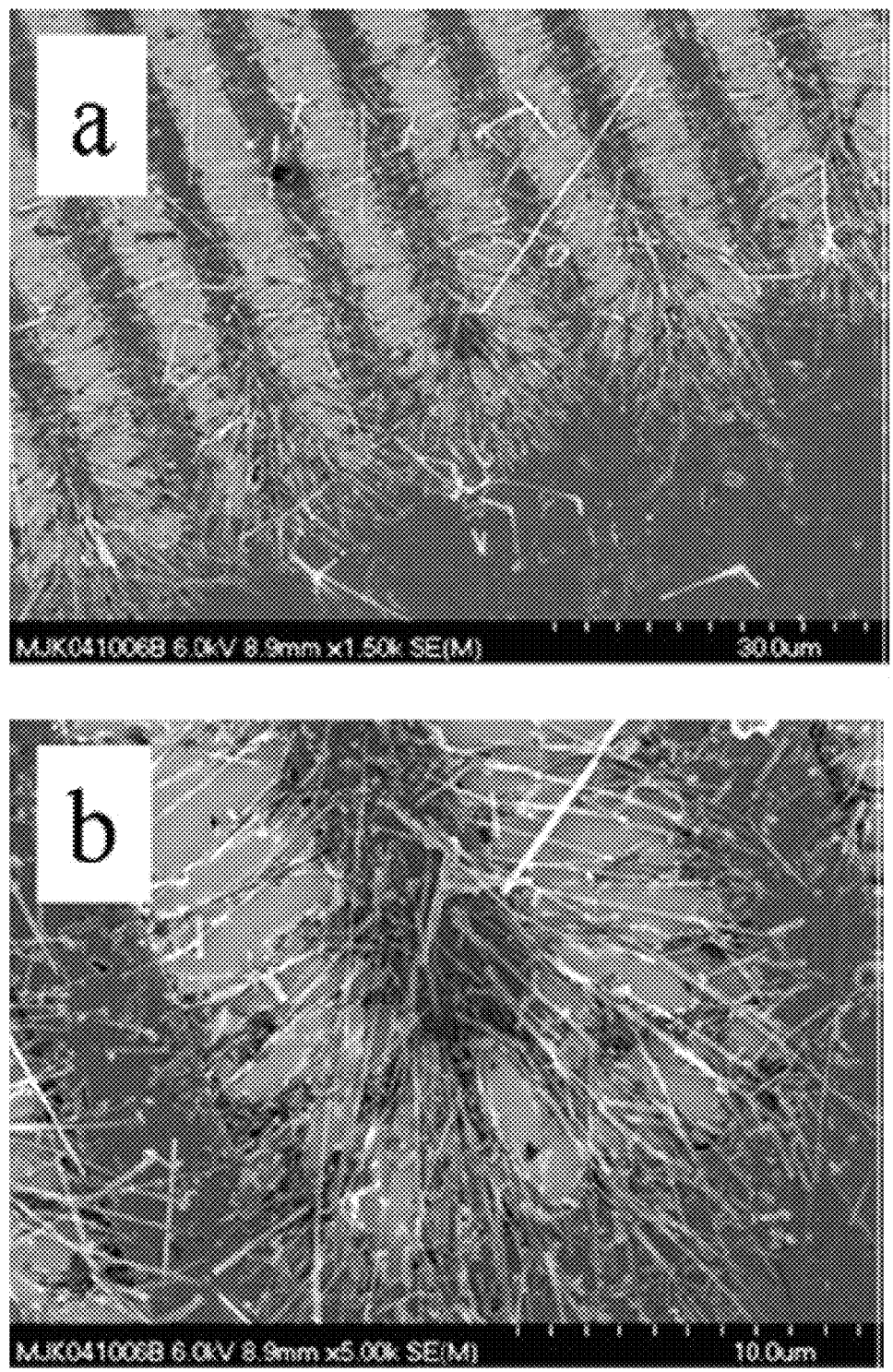
FIG. 23 is an SEM image illustrating concentrated collection of $TiO_2$ nanowires by dielectrophoresis, acting preferentially in the region of highest E-field gradient.
Figure 24:
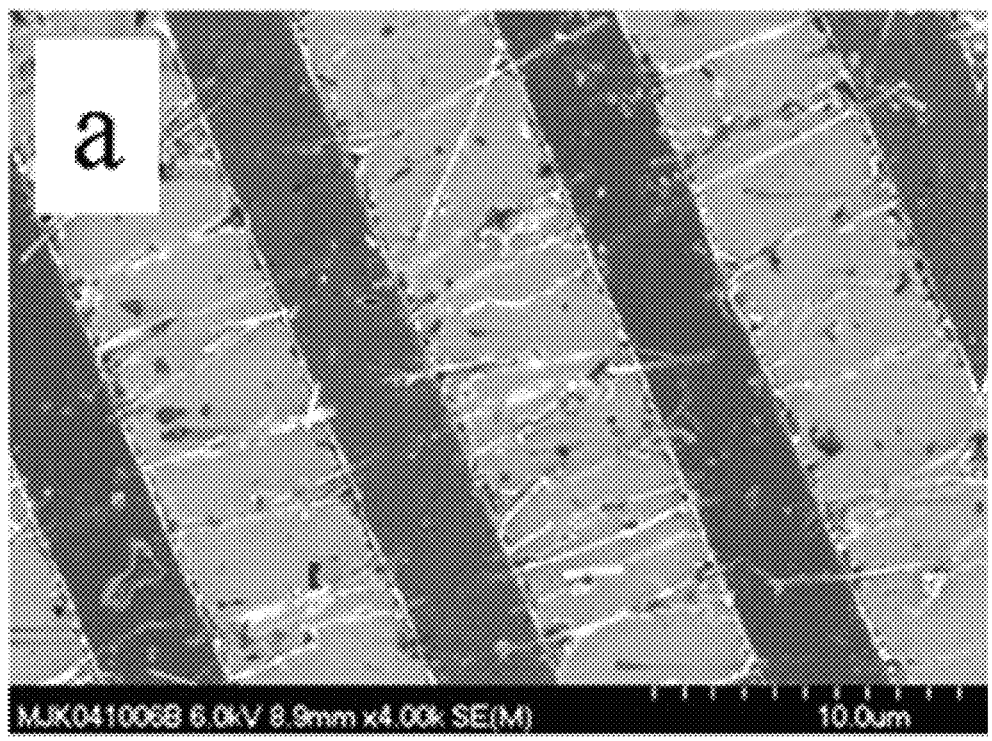
FIG. 24 shows SEM images illustrating more homogeneous dispersion and alignment by E-field induced torque in concert with dielectrophoresis of harvested nanowires.
Figure 24:
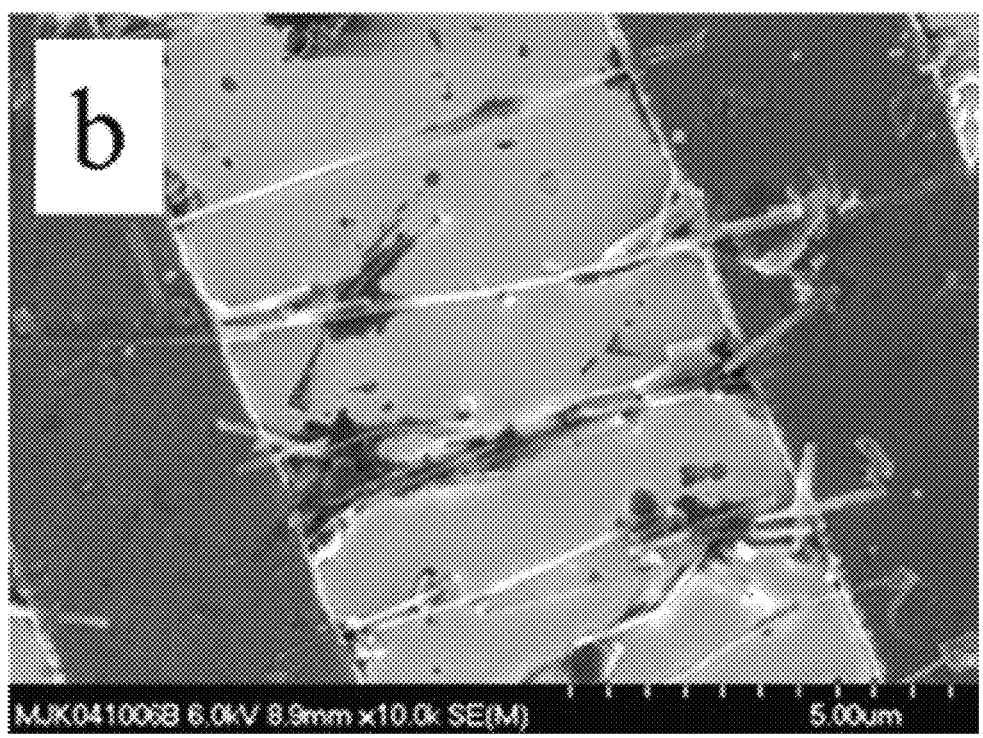

FIG. 23 is an SEM image illustrating concentrated collection of $TiO_2$ nanowires by dielectrophoresis, acting preferentially in the region of highest E-field gradient. This image shows that congregation occurs in areas of nonuniform E-field, illustrating positive dielectrophoresis. Similar nanowire-electrode contact and bridging problems may occur, as discussed above. However, with suitably dilute suspensions and well-implemented purification according to aspects of the subject innovation, reasonably uniform dispersal may be achieved. Purification can permit uniform integration by disallowing numerous particles, chunks, and nanowire segments from interfering with contacts between opposing electrodes by bridging nanowires. FIG. 24 shows SEM images illustrating more homogeneous dispersion and alignment by Efield induced torque in concert with dielectrophoresis of harvested nanowires.

Catalytic reaction sites were engineered into these nanostructures by the addition of nanoparticles atop the nanowires or nanofibers in a "bottom-up" fabrication approach.

Physical vapor deposition (PVD) was applied using radiofrequency-magnetron sputtering of various metal targets. A quartz crystal thickness monitor provided 0.1 nm deposition accuracy. With this control, individual particles were formed for effective "film thicknesses" of <1 nm, as verified by SEM. Catalyst deposition was applied after nanowires had been deposited upon the sensor platform. Electrical continuity checks of deposits upon reference substrates possessing only the interdigitated pattern showed no conductivity for deposits that were <2 nm in effective thickness. In some samples, deposition was applied after initial testing so as to quantify the gains using the catalyst nanoparticles relative to bare nanowires.

Figure 25:
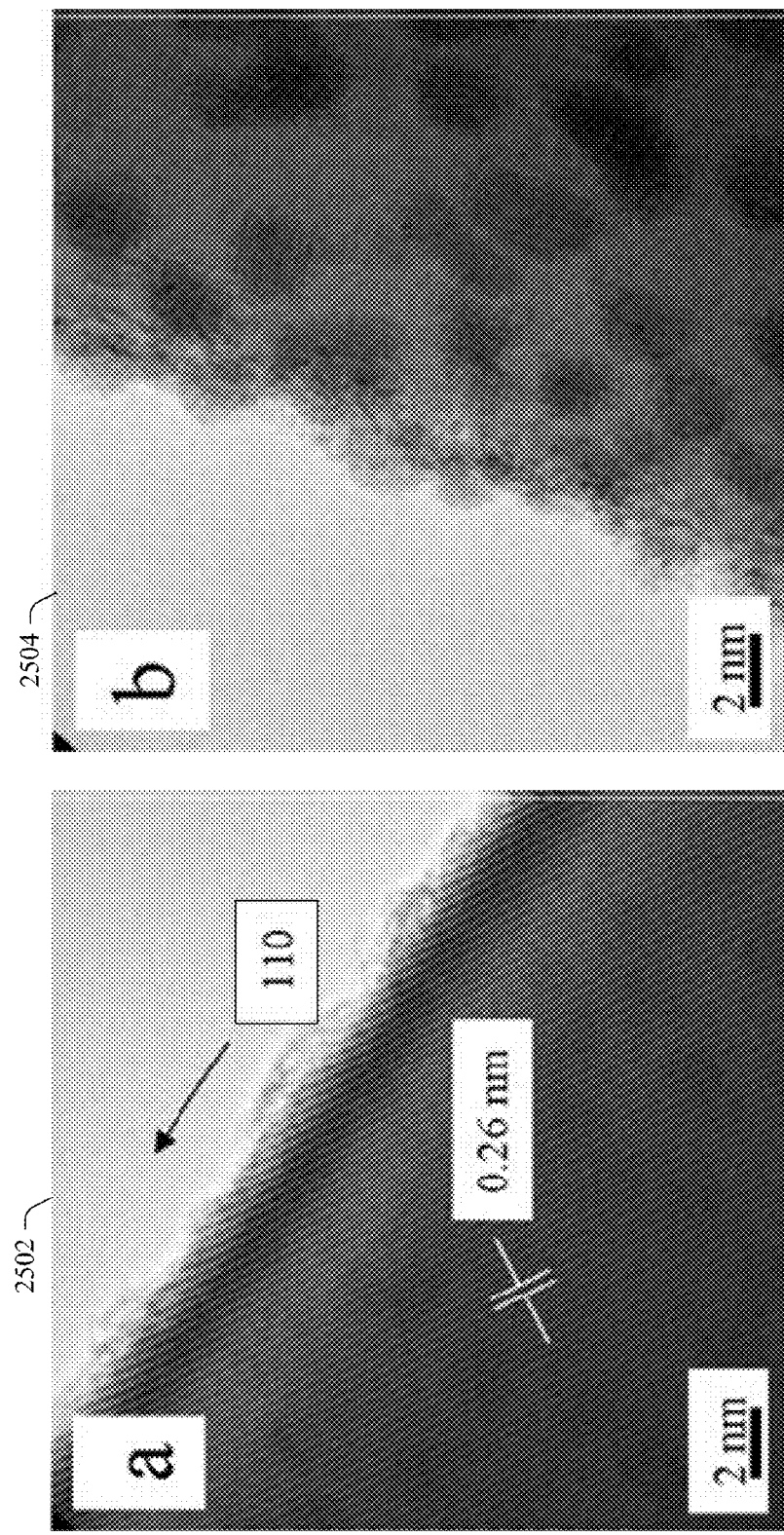
FIG. 25 shows HRTEM images of Pd deposited on $SnO_2$ nanowires.

FIG. 25 shows HRTEM images 2502 and 2504 of Pd deposited on $SnO_2$ nanowires. Again, the boxed number in image 2502 is a Miller index. As can be seen in images 2502 and 2504 the catalyst particles are relatively uniform in size and shape. The very high magnification image, 2504, shows the single-crystal structure of the deposited catalyst. The lattice planes of the nanowire extend to the surface, as seen in image 2502. With the appropriate focusing of the TEM instrument, the crystallinity of the nanoparticles is apparent in image 2504.

Gas testing was conducted in a test chamber connected to a gas-flow chamber. The sensor temperature was controlled by a heating element. Electrical contact was established with probes, voltages were applied across the interdigitated electrodes and currents were measured using current-voltage instrumentation with dedicated data acquisition and software. A typical test comprised the sequential application of air, $N_2$, 0.5% $H_2$ in $N_2$, and terminated with air.

Figure 26:
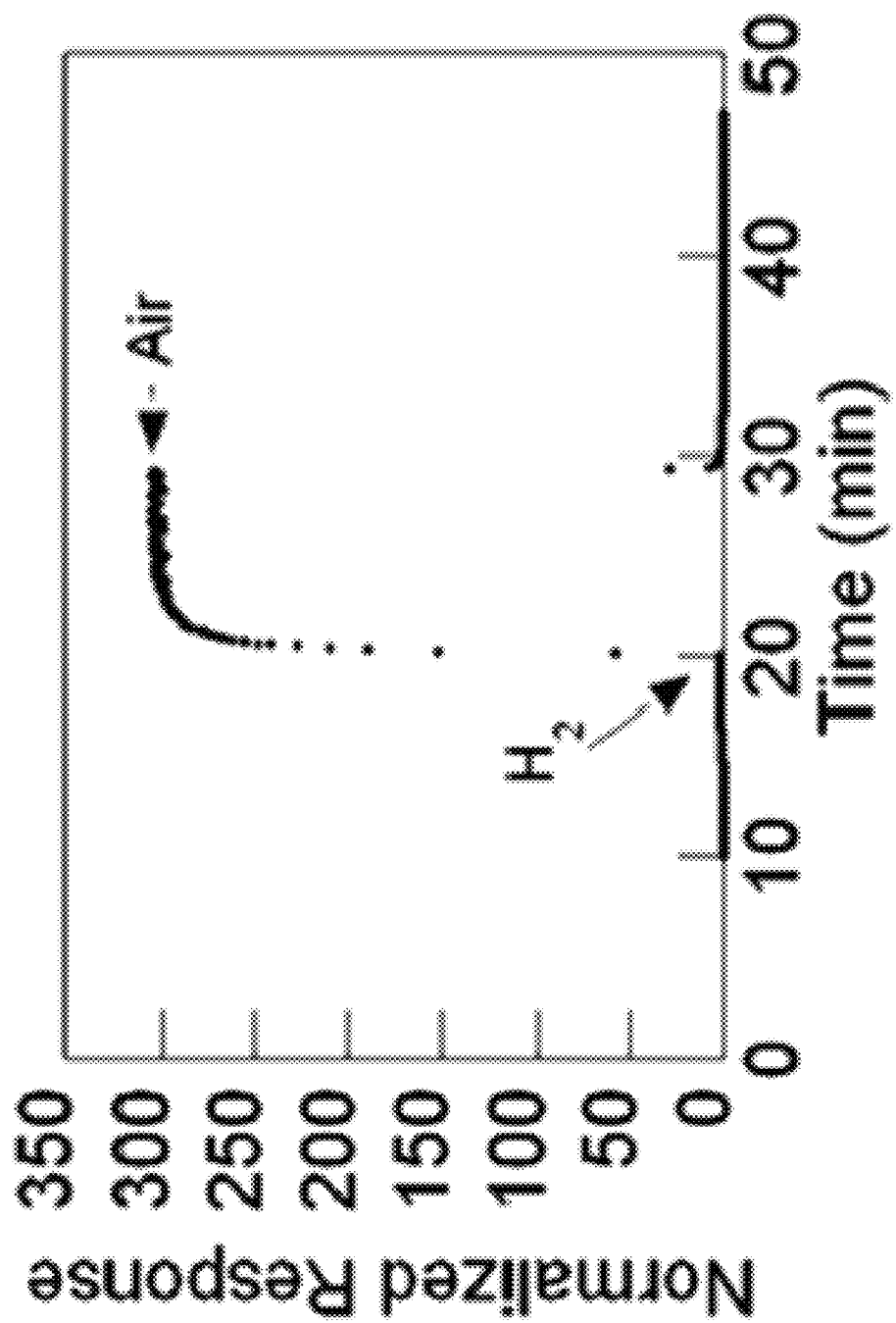
FIG. 26 shows the conductance versus time response at 200° C. of a Pd-coated $SnO_2$ nanowire sensor upon exposure to 0.5 percent $H_2$ in $N_2$.

Shown in FIG. 26 is the conductance versus time response at 200° C. of a Pd-coated $SnO_2$ nanowire sensor upon exposure to 0.5 percent $H_2$ in $N_2$. The $SnO_2$ nanowires were grown using the TEC method. The sensor's normalized response to the reducing gas was defined as the difference between the maximum and baseline conductivity normalized by the baseline conductivity. The maximum as well as the baseline conductivity value was obtained from averaged data in order to decrease noise sensitivity.

Figure 27:
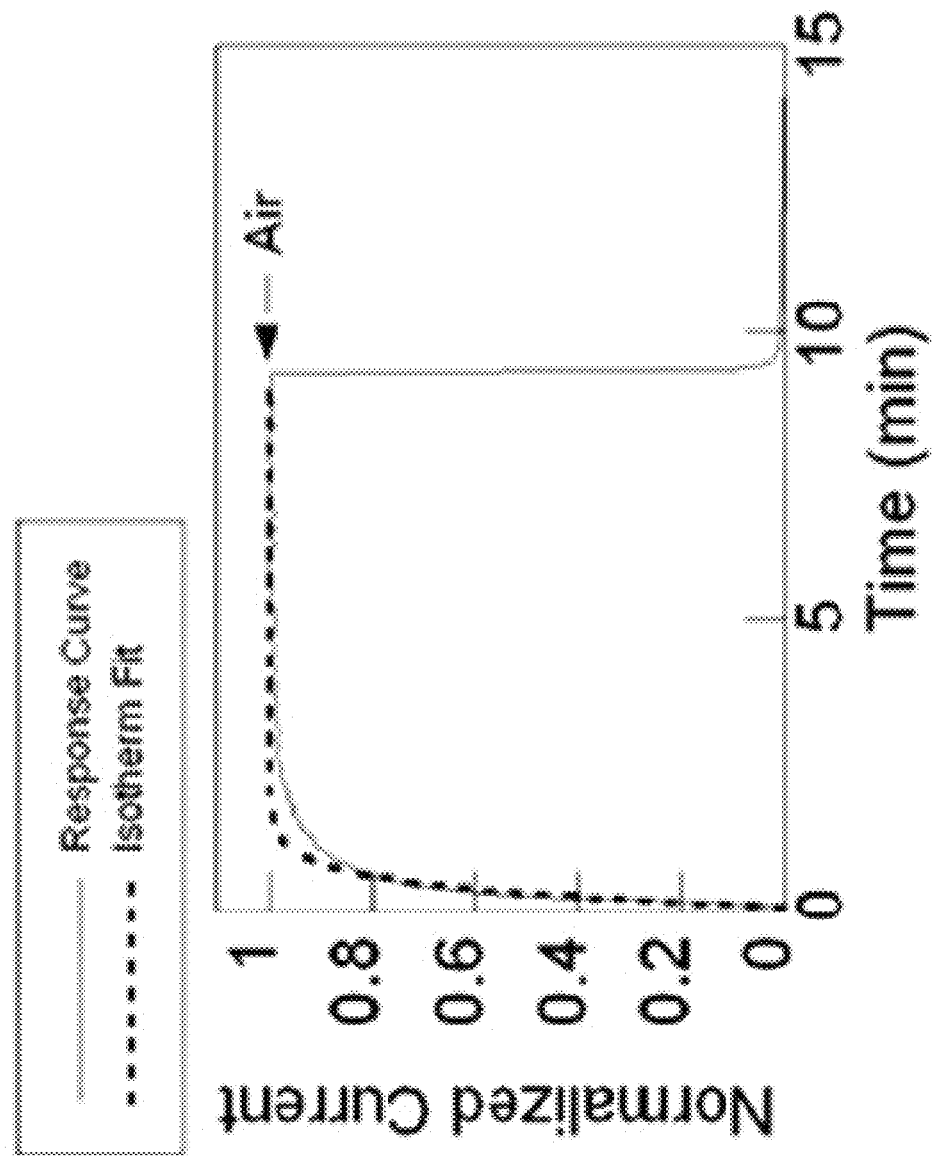
FIG. 27 shows an example of a response curve fitted with the isotherm for a Pd-coated $SnO_2$ sensor to 0.5% $H_2$ in $N_2$.

The expression for gas-surface adsorption rate based on collision kinetics characterizes the adsorption of hydrogen on the metal oxide surface (and reaction with pre-existing chemi-sorbed oxygen species), as shown in equation 8:

$$\theta = [1 - \exp(-Kt)] \quad (8)$$

where θ is the fractional adsorbate coverage, K is the rate constant, and t is time in seconds. The rate constant K is defined by equation 9 as, $$K = K_A P N \quad (9)$$

where $K_A$ is the adsorption rate, P is the adsorbate partial pressure, and N is the number of adsorption sites. The current value of the waveform was rescaled from 0 to 1 in order to curve fit the function. FIG. 27 shows an example of a response curve fitted with the isotherm for a Pd-coated $SnO_2$ sensor to 0.5% $H_2$ in $N_2$. Before fitting, the response curve was baseline corrected and normalized to unity.

The analysis described above presumes that the limiting step in the surface redox reaction(s) is the gas adsorption while the rates of surface diffusion (of either redox species) and the reaction(s) are comparatively fast. Physically, this analysis is valid, based upon chemisorbed oxygen species reacting and hence being removed as a reaction site. This is analogous to physical adsorption where available surface sites are consumed by occupancy during the formation of a monolayer.

In general, three factors could influence the observed response rise time: gas-surface adsorption (and dissociation of adsorbing species), surface diffusion of (atomic or fragment) species, and the actual redox reaction between such species. That such an analysis well describes rise times for SnO2 nanowires and nanofibers, with and without catalysts, supports the assumption that reaction between hydrogen (atoms) and chemisorbed oxygen is fast and consequently the reaction rate does not affect the observed temporal (conductivity) response. In other words, the catalyst does not change the model's fit to the observed time response, which it would if it affected the reaction rate between reducing gas (here H-atoms) and chemisorbed oxygen species. Therefore, the redox reaction and its rate must be independent of the catalyst. Moreover, the increased response rate with catalysts (for both nanowires and nanofibers) compared to the noncatalyst system further implicates adsorption and dissociation as governing the observed response. This is consistent with Pd's well-known role as a catalyst causing dissociation of $H_2$ with H-atom spillover to the metal-oxide interface and surrounding oxide.

A second possible contribution to the sensor response rate is surface diffusion of adsorbed (and dissociated) species. Again, the good agreement of the adsorption fit with experimentally observed conductivity rise times suggests that surface migration of species is not contributing to the observed response rates. If surface migration of species governed the response rate, a $\sqrt{t}$ dependence would be observed, reflecting a diffusion mechanism. Surface diffusion need not even occur in this simple adsorption/dissociation model.

If gas adsorption governs the observed temporal response as the rate-limiting step, the effect of temperature is to facilitate dissociation of adsorbing species. This is because the only observation of gas adsorption is a change in $SnO_2$ conductivity, the net result of the reaction between dissociated $H_2$ and chemisorbed oxygen species. Such dissociative chemisorption can be described by a single step Arrhenius activation energy.

The activation energy was determined from the temperature dependence on the rate constant. The Arrhenius equation is expressed in equation 10, $$K = A e^{-E_a / K_b T} \quad (10)$$

where A is the pre-exponential, $E_a$ is the activation energy, T is the temperature, and $K_b$ is the Boltzmann constant. By plotting the natural logarithm of K versus inverse T and linearly fitting the data, $E_a$ was determined from the slope of the fit.

Figure 28:
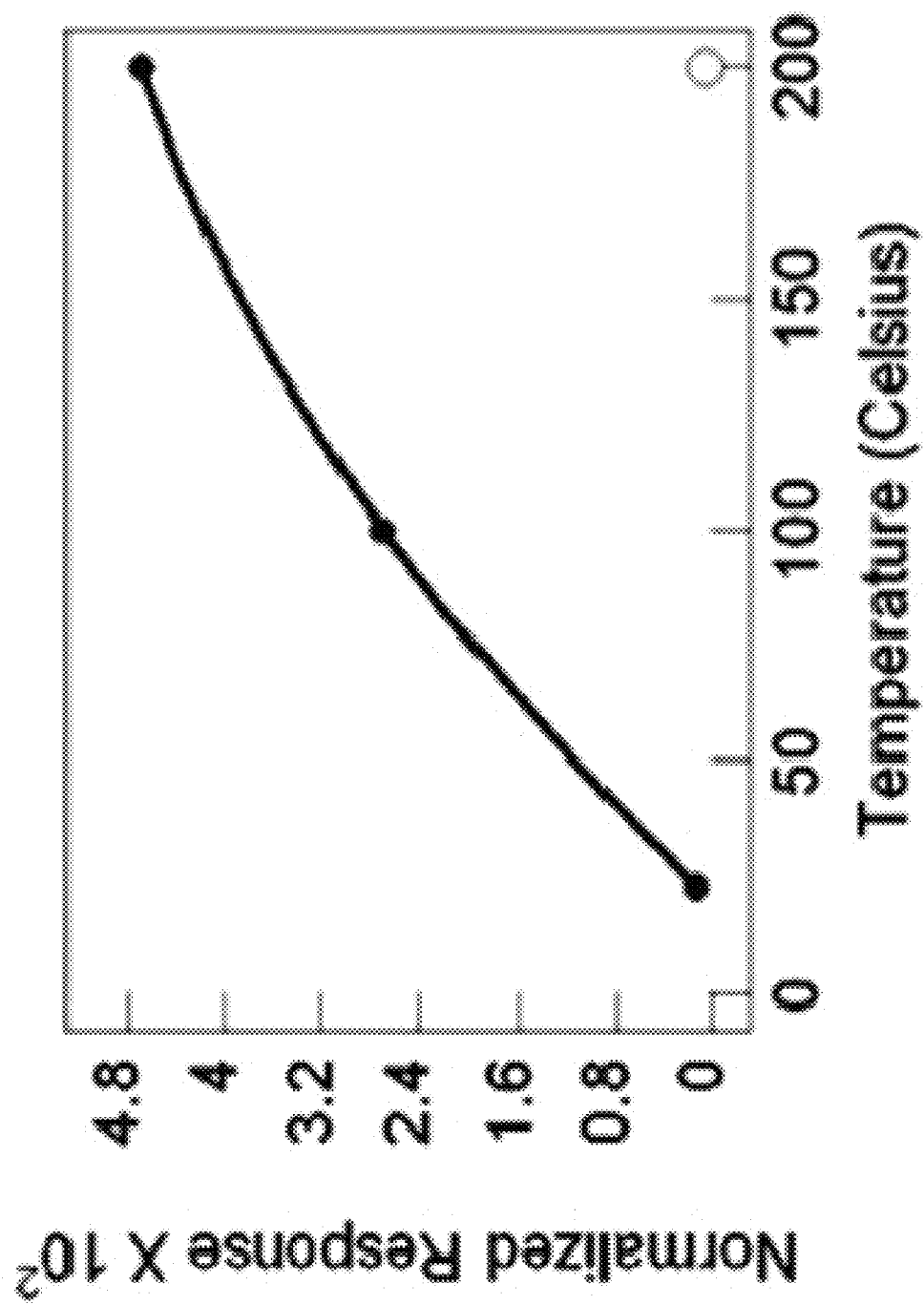
FIG. 28 shows $SnO_2$ nanowire sensor response versus temperature.
Figure 29:
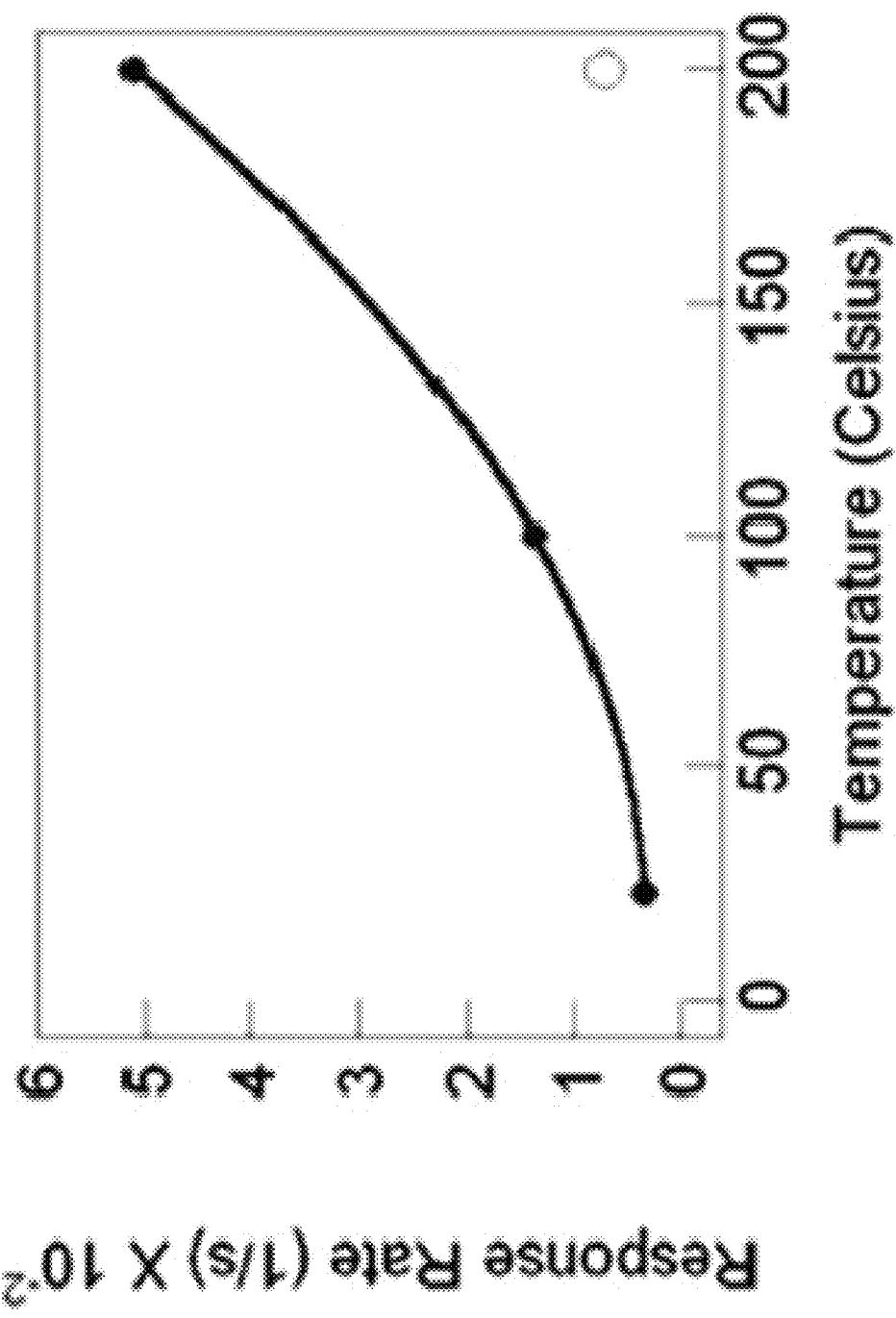
FIG. 29 shows $SnO_2$ nanowire sensor response rate versus temperature.

For the sensors with $SnO_2$ nanowires grown by TEC, the response magnitude and the response rate increased with increasing temperature. Substantial gains in response were realized with the deposition of 0.5 nm Pd catalyst, as illustrated by the best-fit quadratic curve, to highlight the response trend. FIG. 28 shows $SnO_2$ nanowire sensor response versus temperature. Compared to the nascent $SnO_2$ nanowires at 200° C. with a response gain of ~5, Pd deposition brought a response gain of ~500 at 200° C. and nearly 15 at 23° C., as shown in FIG. 28. In FIG. 28 and elsewhere, the filled circles represent results with the catalyst (Pd in FIG. 28), while the unfilled circle represents the results without the catalyst. Similarly, as seen in FIG. 29, which shows $SnO_2$ nanowire sensor response rate versus temperature, the nanowire sensor's response rate with Pd catalyst improved with increasing temperature and there was a response rate gain of nearly 7-fold at 200° C. with catalyst as compared to nascent $SnO_2$.

Metal nanoparticles can promote catalytic dissociation of $H_2$ with H-atom spillover to the metal-oxide interface, thereby facilitating reaction with chemisorbed oxygen in the interfacial region. With increasing temperature, H-atom migration via surface diffusion can extend further from the Pd nanoparticle and bring about greater removal of chemisorbed oxygen from the species. In other words, the zone of influence of the catalytic island is increased. If the conductivity change is limited to strictly a surface depletion region in the nanowires, an increased diffusional distance with increasing temperature would account for the sensitivity gains with temperature of the $SnO_2$ nanowires with Pd catalyst. Essentially, more chemisorbed oxygen species are accessible at elevated temperature. Additionally, the reaction yield may be increased, as more reaction pairs can surmount the activation energy.

Figure 30:
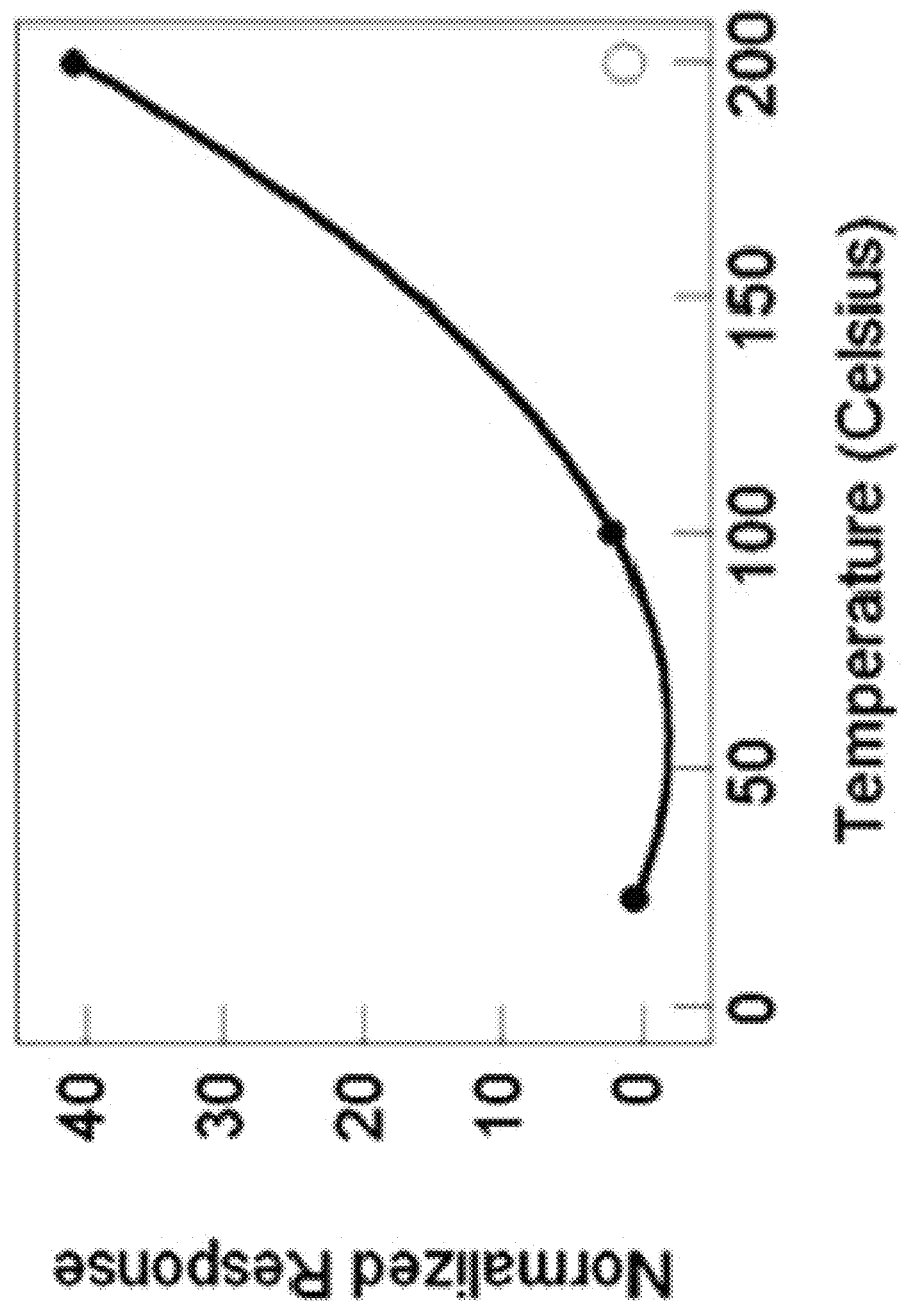
FIG. 30 illustrates $TiO_2$ nanowire sensor response versus time.
Figure 31:
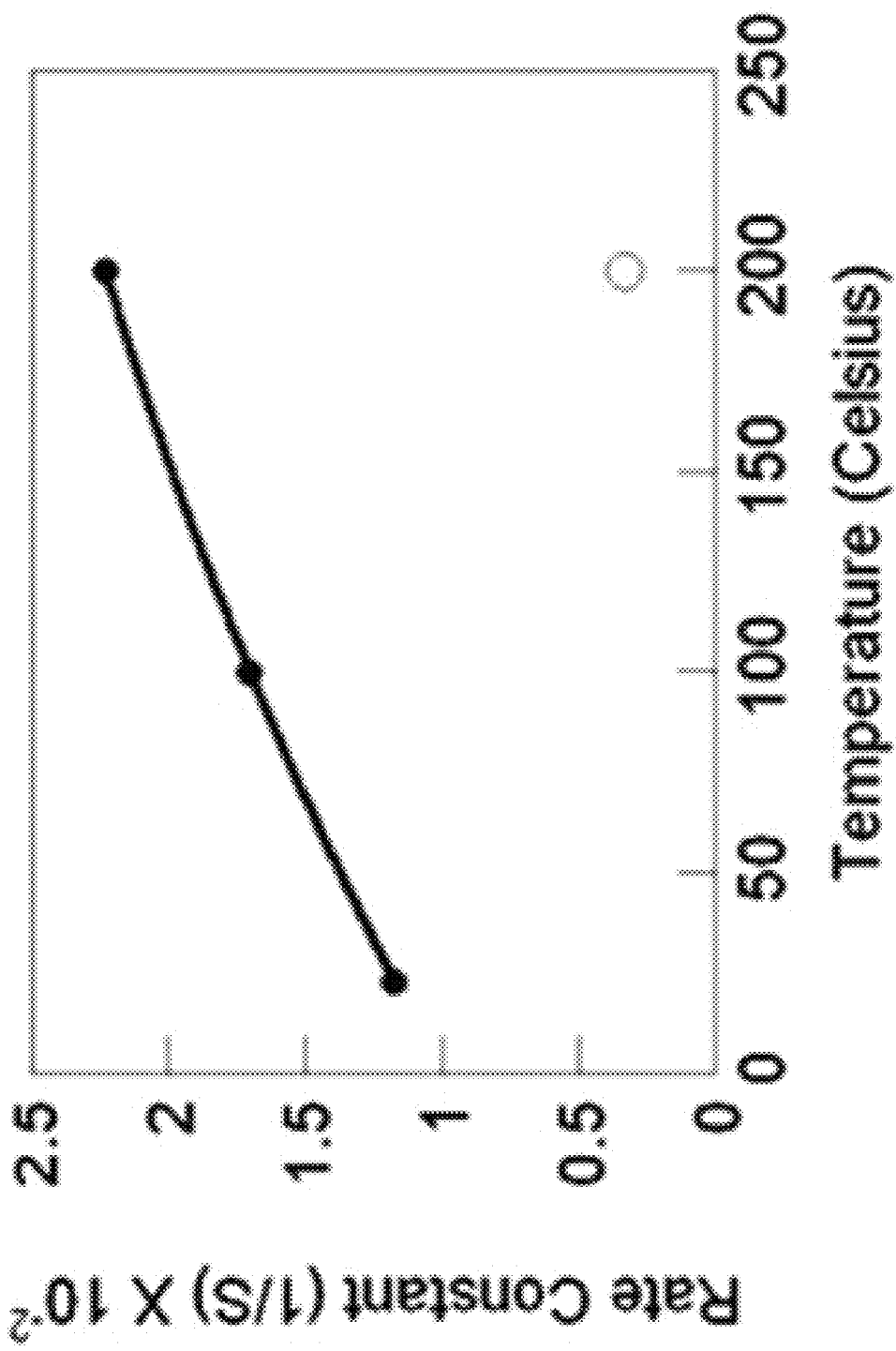
FIG. 31 illustrates $TiO_2$ nanowire sensor response rate versus temperature.

As was the case for the sensors with $SnO_2$ nanowires grown by TEC, the response magnitude and the response rate for sensors with $TiO_2$ nanowires formed via controlled oxidation increased with increasing temperature. Likewise, as shown by FIG. 30, which illustrates $TiO_2$ nanowire sensor response versus time, substantial gains were realized with the deposition of 0.5-nm Pt catalyst, again as illustrated by the best-fit quadratic curve, to highlight the response trends. Again, and in subsequent Figures, the filled circle indicates results obtained with the catalyst, and the unfilled circle those obtained without. As shown in FIG. 30, the catalyst yielded approximately a 100-fold increased response and nearly a 10-fold increase in response rate at 200° C. Notably, the Pt catalyst enabled operation at ambient temperature with the same response level as the nascent $TiO_2$ showed at 200° C. More generally, as seen in FIG. 31, illustrating $TiO_2$ nanowire sensor response rate versus temperature, Pt nanoparticles catalysts yielded an increased sensitivity and increased temporal response with temperature. Even at ambient temperature, the temporal response was dramatically improved relative to the nascent material (at 200° C.) by nearly a factor of 4.

Figure 32:
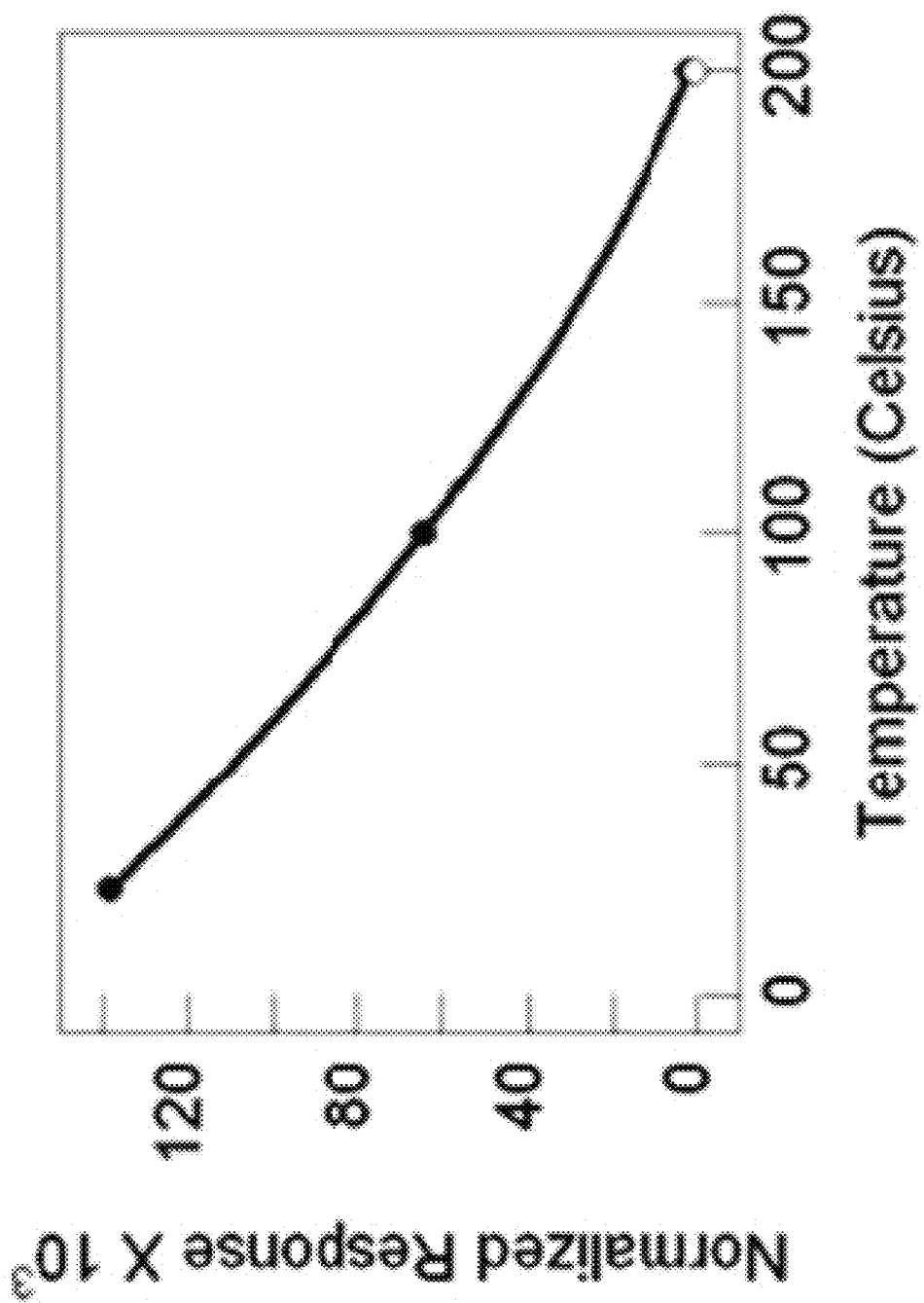
FIG. 32 shows $SnO_2$ nanofiber sensor response versus temperature.
Figure 33:
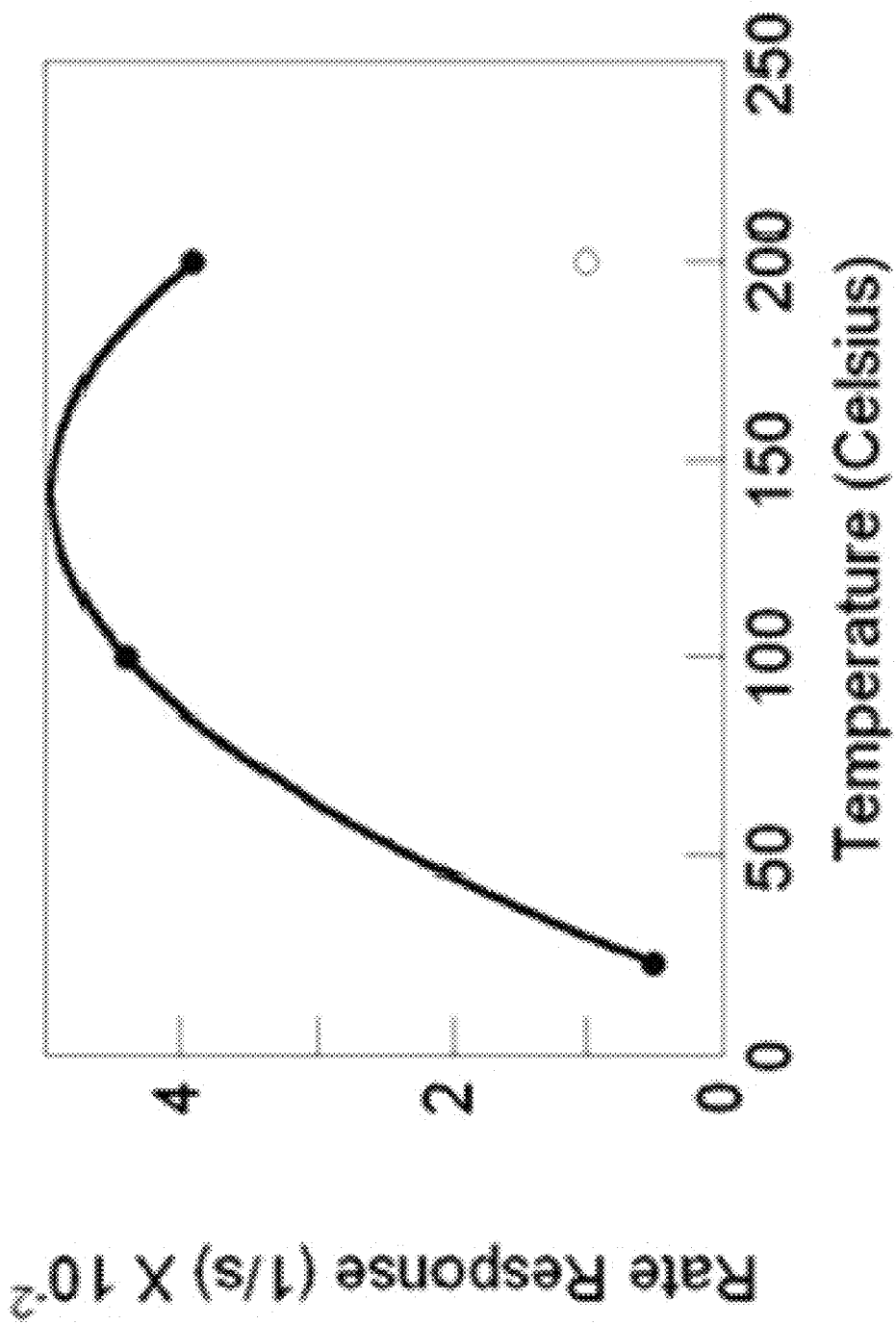
FIG. 33 illustrates $SnO_2$ nanofiber sensor response rate versus temperature.

For the sensors with $SnO_2$ nanofibers formed by electrospinning, the temperature dependence on the response magnitude was reversed as compared to that of the sensor with $SnO_2$ nanowires grown by TEC. As demonstrated by the results shown in FIG. 32, which shows $SnO_2$ nanofiber sensor response versus temperature, the response magnitude decreased with increasing temperature. However, FIG. 33, illustrating the $SnO_2$ response rate versus temperature, shows that the response rate increased with temperature. As in all other cases, there were substantial gains with the deposition of Pd catalyst, as illustrated by the best-fit quadratic curves. The magnitude of the response was enormous compared to the sensor with $SnO_2$ nanowires, a $10^4$-fold difference at 23° C., for example.

There are several aspects that may explain the enormous response relative to the nanowire-based sensors. First, the potential barrier modulation between the grains of a nanofiber acted to amplify the resistance change in the presence of $H_2$. Although the nanofiber was comparable in diameter to the nanowire, its open porosity and more exposed volumetric surface area likely facilitated chemisorptions processes throughout the nanofiber. Both carrier concentration and mobility were then modulated in the majority of particles. The constituent particle size of the nanofiber would permit the depletion layer to extend throughout the particle volumetrically, thereby avoiding conducting shorts in parallel with the near-surface layer as can be common for thick film materials. The nanowire morphology is not necessarily the limiting form of a polycrystalline chain as suggested by comparison of equations 5 and 6.

The temperature dependence on the response magnitude can be explained by considering the temperature effect on the adsorbed oxygen. Higher operating temperature will increase reaction rates but may lower response by removing physisorbed species and possibly some fraction of chemisorbed oxygen such as $O_2$ (or transforming them into more strongly adsorbed species such as O). Notably, this transformation begins at ~150° C. The result is a lower baseline resistance and a decreased dynamic response. Tests at higher temperature support this interpretation by a further diminishing response.

A comparison of the above results indicates that the decreased sensitivity response with temperature of the nanofibers with Pd catalyst is not apparently operative for the nanowires with Pd catalyst, where instead response gains are observed. Part of the reason for this is that varied crystallographic surfaces presented by the nanofiber's polycrystalline structure coupled with porosity may increase chemisorbed oxygen loss (or again their transformation to O) with increasing temperature. This effect, coupled with no gain in surface accessibility to migrating H-atoms with increasing temperature can account for the declining response with temperature. Based on the above results, increased reactivity of chemisorbed oxygen species was not comparable relative to these considerations. In contrast, for the nanowire, the increased number of chemisorbed oxygen sites accessible by surface diffusion with increasing temperature could outweigh their decreased surface concentration (and/or reactivity) at the moderate temperature of 200° C. Finally, the reciprocal migration of chemisorbed oxygen species towards the metal-oxide interface can also be a contributing factor to the observed response magnitudes.

Single-crystal metal oxide nanowires exposing uniform crystal surfaces without grain boundaries or defects were used for comparative measurements of metal oxides and catalysts. Junction effects and their potential interaction with catalyst nanoparticles were avoided. Four comparisons, each at 200° C., are summarized in the following results.

Tests with the same metal oxide but different catalyst provided a measure of the catalyst activity. Tests between different metal oxides with the same catalyst provided a measure of the oxide reactivity. Analysis results are summarized in Table 1 below, which compares the normalized responses and rate constants for the indicated metal oxide, catalyst systems operating at 200° C. upon exposure to 0.5 percent $H_2$ in $N_2$. In each case, the metal nanoparticle sources H-atoms by the well-known spillover effect. The metal oxide supplies oxygen atoms through chemisorbed species. Both processes can be activated by temperature. Together both processes comprise the coupled redox reactions between reducing species and oxidizing (chemisorbed) oxygen.

TABLE 1

| Material | Normalized Response | Rate constant, $s^{-1}$ | Activation energy, kJ/mol |
|---|---|---|---|
| $TiO_2$/Pt | $4.08 \times 10^1$ | $2.23 \times 10^{-2}$ | 7.1 |
| $TiO_2$/Pd | 1.5 | $3.13 \times 10^{-2}$ | N/A[a] |
| $SnO_2$/Pt | $1.04 \times 10^5$ | $2.27 \times 10^{-2}$ | 4.7 |
| $SnO_2$/Pd | $4.68 \times 10^2$ | $5.10 \times 10^{-2}$ | 17.7 |
| ZnO/Pt | $1.90 \times 10^1$ | $1.80 \times 10^{-2}$ | N/A[a] |
| ZnO/Pd | $2.21 \times 10^1$ | $7.00 \times 10^{-3}$ | 3.3 |

[a]Insufficient data.

Figure 34:
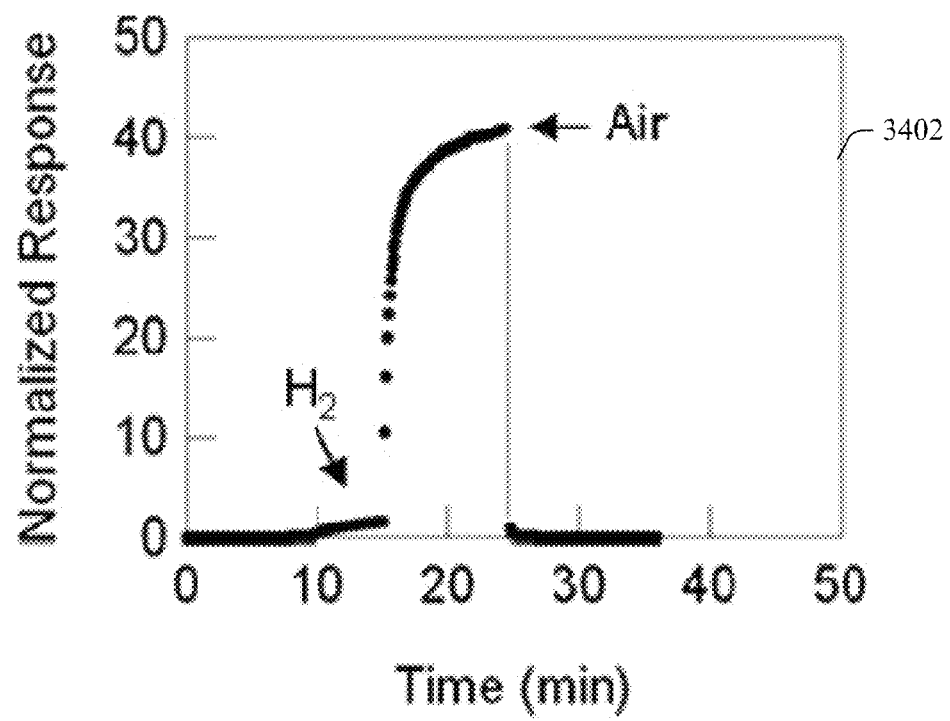
FIG. 34 shows a comparison between a $TiO_2$ nanowire with a Pt catalyst and an SnO2 nanowire with a Pt catalyst.
Figure 34:
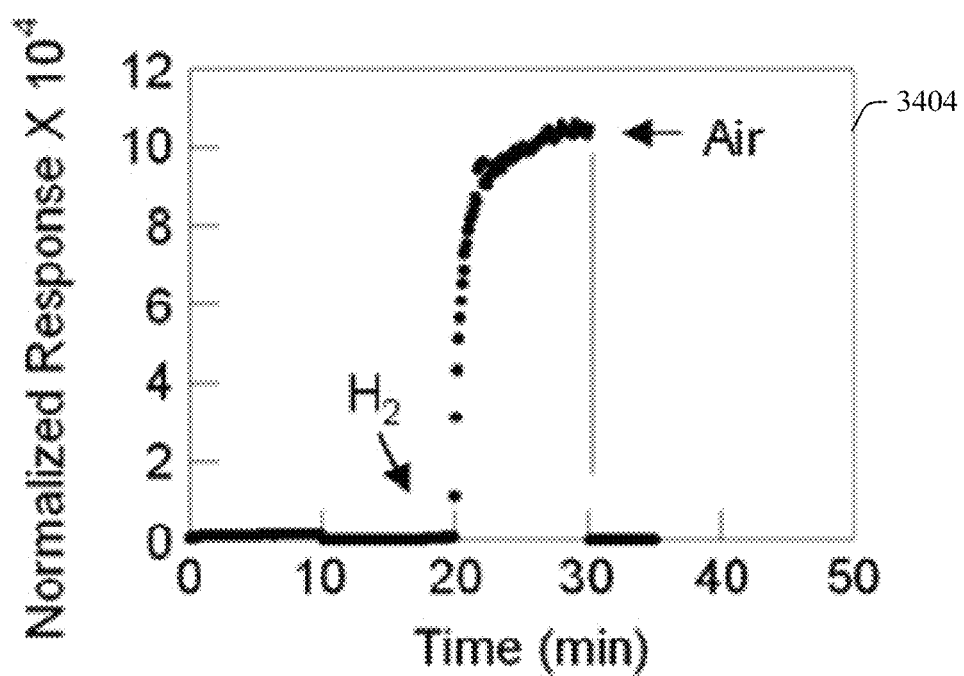

FIG. 34 shows a comparison between a $TiO_2$ nanowire with a Pt catalyst at 3402 and $SnO_2$ with a Pt catalyst at 3404. Sensors based upon these materials differ dramatically in their response. As seen by comparing graphs 3402 and 3404, the $SnO_2$/Pt system exhibited nearly a 2500-fold greater normalized response. The response rates were nearly identical, as shown in Table 1 above. This latter feature is due to the presence of Pt as the common catalyst. It confirms the response difference as being due to the metal oxide. Multiple factors contributed to the greater response for $SnO_2$, including: a more reactive chemisorbed oxygen species, greater chemisorbed species concentration, more mobile/reactive lattice oxygen, and a more polarized interface with the Pt catalyst.

Figure 35:
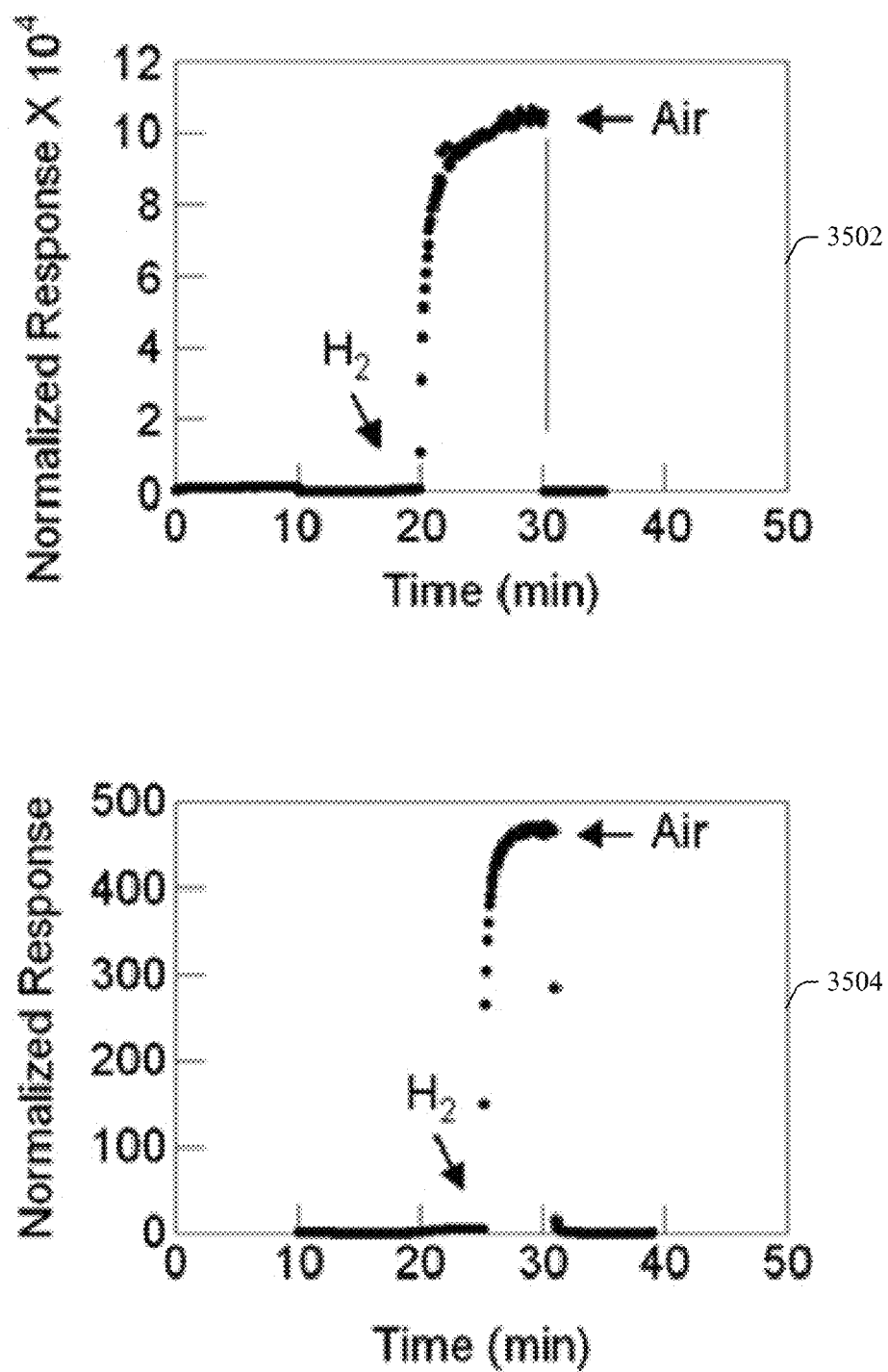
FIG. 35 illustrates a comparison between an $SnO_2$ nanowire with Pt as the catalyst and an $SnO_2$ nanowire with Pd as the catalyst.

FIG. 35 illustrates a comparison between $SnO_2$ with Pt as the catalyst in graph 3502, and $SnO_2$ with Pd as the catalyst in graph 3504. Although Pd has been considered a superior catalyst for $H_2$ sensing because of its ability to dissolve hydrogen in the form of H-atoms at ambient temperature, Pt was found to be superior the superior catalyst upon the $SnO_2$ nanowires in FIG. 35. At 200° C., it yielded a 200-fold greater response than the corresponding $SnO_2$ nanowires sensitized with Pd catalyst. In fact, these responses were comparable in magnitude to the electrospun nanofiber with Pd catalyst at 100° C. and 10-fold greater at 200° C. The rates, shown in Table 1, were faster by roughly a factor of 2. Interestingly, despite the greater response, for $SnO_2$, the Pt catalyzed rate is only ~½ that of the Pd catalyzed system at 200° C., as seen in Table 1.

These results show that there is strong interaction between the catalyst and oxide nanostructure for $SnO_2$. Both the $SnO_2$/Pt and $SnO_2$/Pd systems exhibited the trend common to nanowires with increasing response magnitude and temporal rate with increasing temperature. Such a trend is consistent with catalytic dissociative adsorption governing the reaction rate, as discussed above. For the same deposition conditions, similar dispersions should be realized for each catalyst. Therefore, while the rate suggests which catalyst was more active, the response magnitude (for the same oxide, nanostrucure and gas exposure conditions) reflects the increased reactivity of the chemisorbed oxygen as facilitated by the catalyst.

Figure 36:
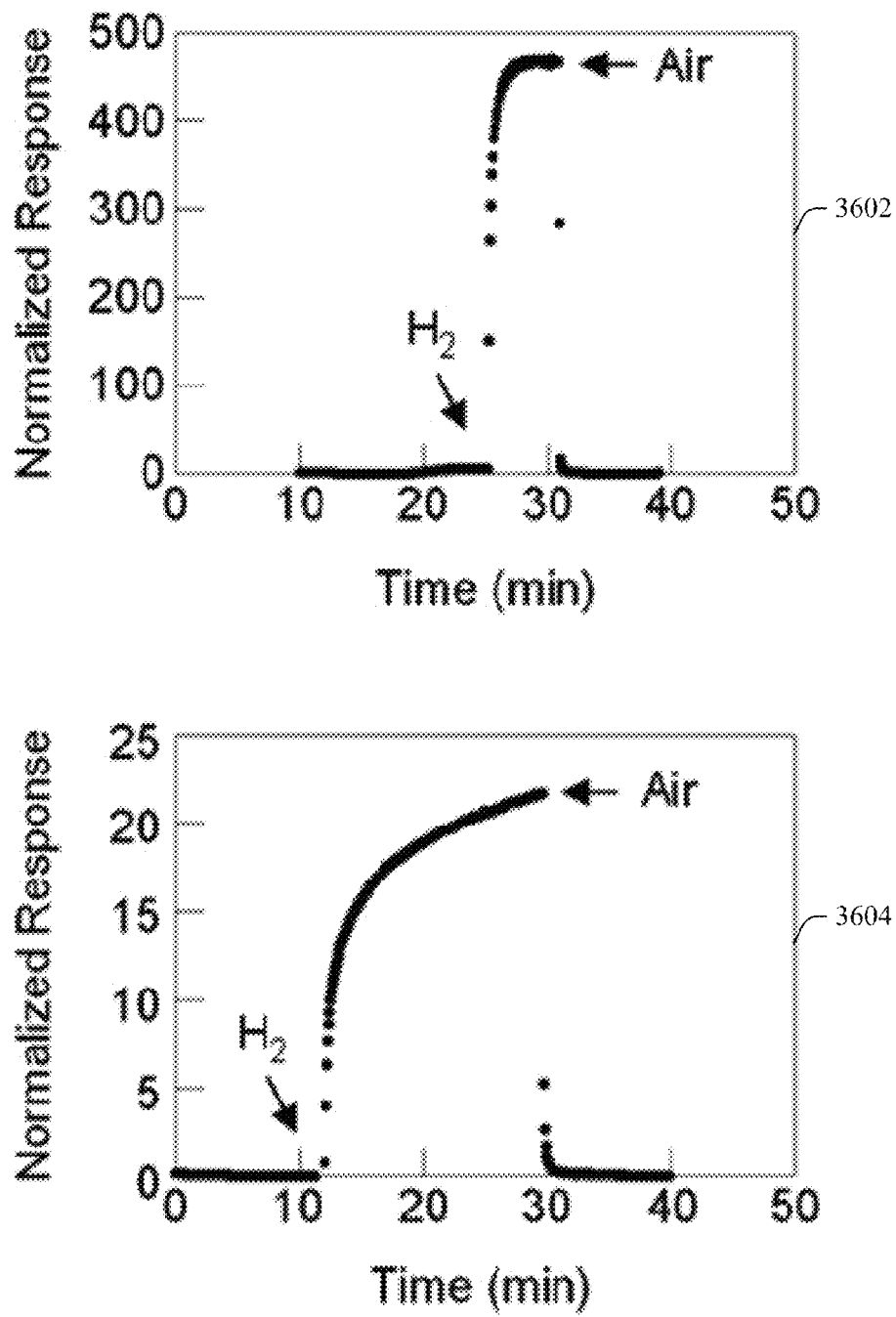
FIG. 36 shows a comparison between an $SnO_2$ nanowire with Pd as the catalyst and a ZnO nanowire with Pd as the catalyst.

FIG. 36 shows a comparison between $SnO_2$ with Pd as the catalyst in graph 3602 and ZnO with Pd as the catalyst in graph 3604. Synthesis of ZnO, as discussed above, is straightforward and yields single-crystal morphologies. This material afforded an opportunity to further test a different single crystal, and its response relative to the $SnO_2$ nanowires. The $SnO_2$/Pd system, shown in graph 3602, responded by a factor of 20-fold greater than the ZnO/Pd system of graph 3604, with a 7-fold faster rate at 200° C., as seen in Table 1 above. At 100° C., the SnO2/Pd response magnitude was roughly 70 times greater than the ZnO/Pd, but only about 1.5 times as fast. These differences illustrate the relative inertness of ZnO, since the Zn cation does not exhibit variable oxidation states, as does SnO2 and other oxides. The results suggested that the ZnO material produced here possessed comparatively few defects. Its response magnitude also increased with increasing operating temperature. The same factors as listed for the SnO2/Pt system above are considered applicable here. The response rate for ZnO/Pd declines with temperature. One possible explanation for this is transformation and/or loss of chemisorbed oxygen species. As with the other nanowire and catalyst combinations, the response magnitude increased with operating temperature, consistent with catalytic dissociation and/or activation of chemisorbed oxygen species.

Based on the above comparisons, $SnO_2$ was clearly the more active oxide material compared to $TiO_2$ and ZnO, for nanowires of each of these materials. Comparison of Pd and Pt catalysts across these oxides indicates that Pt was the more active catalyst for $H_2$. Results with Pd upon electrospun material demonstrate the importance of oxide nanostructure. Based on the above results and analysis, the catalyst/oxide combination is best considered as a coupled system. Tests for identification of the best catalyst or oxide can include nanostructure as a consideration to the extent that surface and lattice defects contribute to conductivity and reactivity, and synthesis methods are also a relevant consideration.

The above results highlight the synergy of catalyst with metal oxide nanostructure. Catalysts can contribute to an enhanced sensitivity response via an electronic or chemical contribution. Electronically, the metal can remove electron density from the metal oxide by virtue of its electronegativity. With reduced charge carrier concentration and mobility, the metal oxide is thereby sensitized to reducing gases. Alternatively, the metal nanoparticle can actively catalyze the decomposition of adsorbates such as $H_2$ molecules. The resulting H-atoms will undergo "spillover" to the oxide, react with either chemisorbed or lattice oxygen and release charge to the semiconductor resulting in an increased conductivity. The relative contributions will depend upon the catalyst, reducing gas and operating temperature.

Also apparent from the above results is that catalyst nanoparticles substantially improved sensor time constants relative to the nascent oxide. This is a clear indication that they provide a bypass to the rate-limiting step, namely dissociation of the reducing gas. Beyond this, the temporal response of the sensor with temperature is the convolution of several competing factors. First, the form of chemisorbed oxygen species changes with temperature; below ~150° C., it is $O_2 \ldots$, between ~150 to 300° C., $O \ldots$, and above ~300° C., $O_2$. Second, the concentration of weakly absorbed chemisorbed species will decrease with increasing temperature. Third, the catalytic dissociation rate of $H_2$ upon the catalyst Pd nanoparticles and associated H-atom spillover will increase. In this more reactive form, reaction of reducing species with chemisorbed oxygen will occur more rapidly and at lower temperatures than in the absence of the catalysts. Fourth, the migration distance for chemisorbed species along both surfaces increases.

Of the above four factors, factors one and two could slow the response rate, while factors three and four will increase the response rate. More strongly absorbed chemisorbed species with lower concentrations will slow the surface redox reaction rates. Conversely, faster reactant diffusion and generation (H-atoms) will increase the surface reaction rates. Potentially, the size and composition of the nanoparticles can be used to tailor both sensitivity and selectivity. By selection of material composition, physical form (nanowire versus nanofiber, each of which offer very different crystallinity), and nanoparticles (noble metals, e.g., Pt and Pd), the adsorption sites and energies of the nanostructured element may be tailored towards specific gases to the exclusion of common interferents.

For the sensing elements described above, the activation energies were determined and are listed in Table 1, with the exception of $TiO_2$/Pd and ZnO/Pt, as indicated in Table 1. In general, the activation energy represents a global average of a multistep mechanism. Among the more identifiable steps are $H_2$ dissociation, surface atom migration (either H-atom or surface/lattice oxygen species), and reaction. The extent to which the overall activation energy represents each of these steps can be seen by comparison of the activation energy for single-crystal metal oxide nanowires with and without catalyst. However, the activation energies for the nascent metal oxide nanowires without catalyst were not available because of the lack of sensor response at the lower temperatures. This fact reinforces that the deposition of metal nanoparticles as catalysts is clearly advantageous as it can allow lower temperature operation, which, in turn, can reduce the power requirement and extends the lifetime of the sensor. From the discussion above, the fact that catalyst nanoparticles improved the sensor response time at 200° C. indicates that the rate-limiting step is most likely the $H_2$ dissociation, as the catalyst provided an alternative reaction path for this step.

Figure 37:
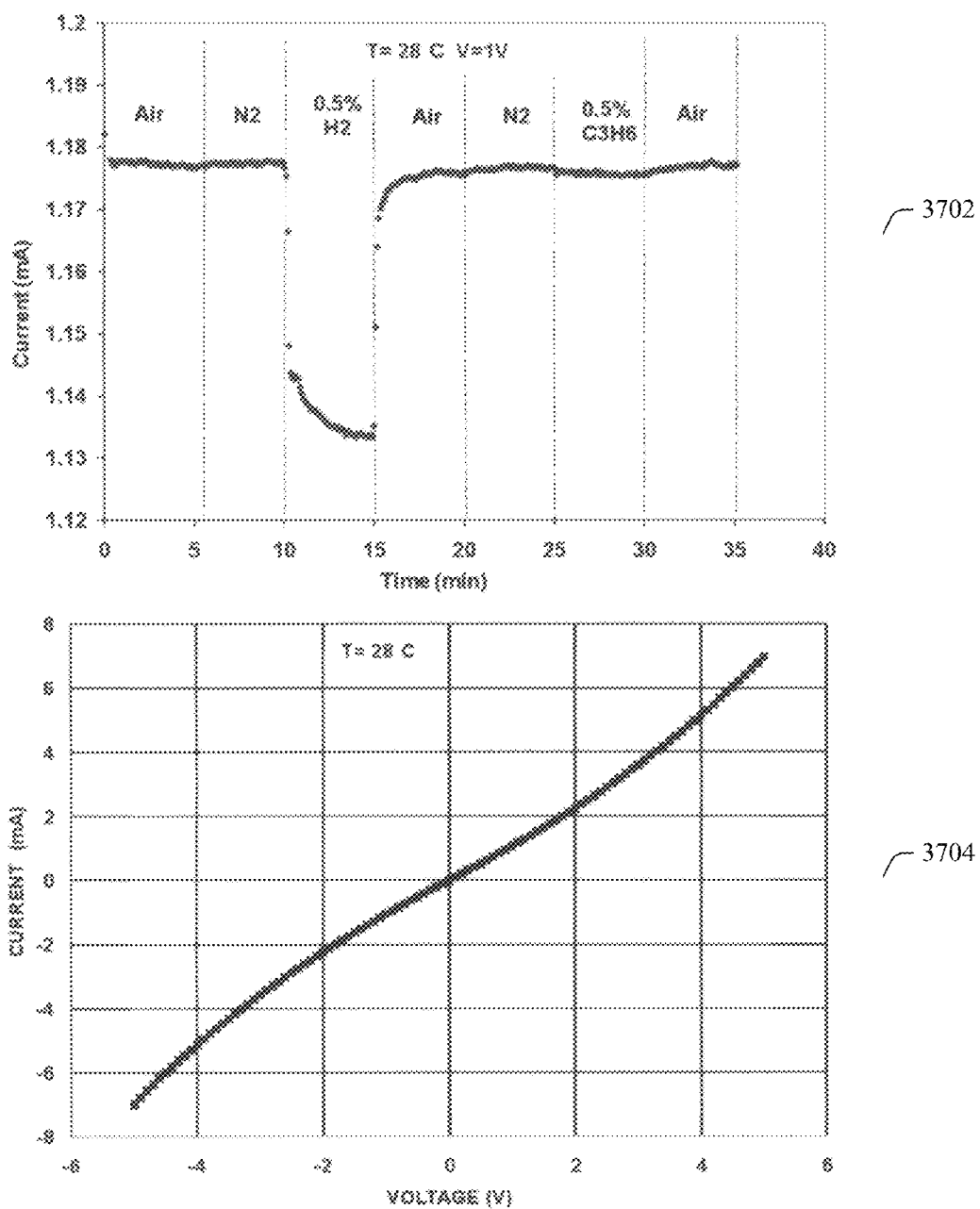
FIG. 37 shows the current response against time and voltage of a MWCNT sensor to various gases at room temperature.

FIG. 37 shows the current response against time and voltage of a MWCNT sensor to various gases at room temperature. Current against time at 1V is shown in graph 3702. The sensor was exposed to air, nitrogen, 0.5% hydrogen in nitrogen (hydrogen/nitrogen), followed by air for 5 minute time intervals. The process was then repeated, with propylene ($C_3H_6$) in nitrogen (propylene/nitrogen) in place of the hydrogen/nitrogen. The data shown in graph 3702 indicates that the sensor established a baseline in air with minimal response to nitrogen, and a decrease in current (p-type response) upon exposure to hydrogen. There was no response to propylene/nitrogen. The effective resistance of the sensor at 1V was seen to be on the order of magnitude of 1000 ohms (1000Ω). Graph 3704 shows the current against voltage response of the sensor from the range of −5V to 5V. As shown in graph 3704, the sensor response was predominantly ohmic below 1V with deviations from that behavior above 2V.

Figure 38:
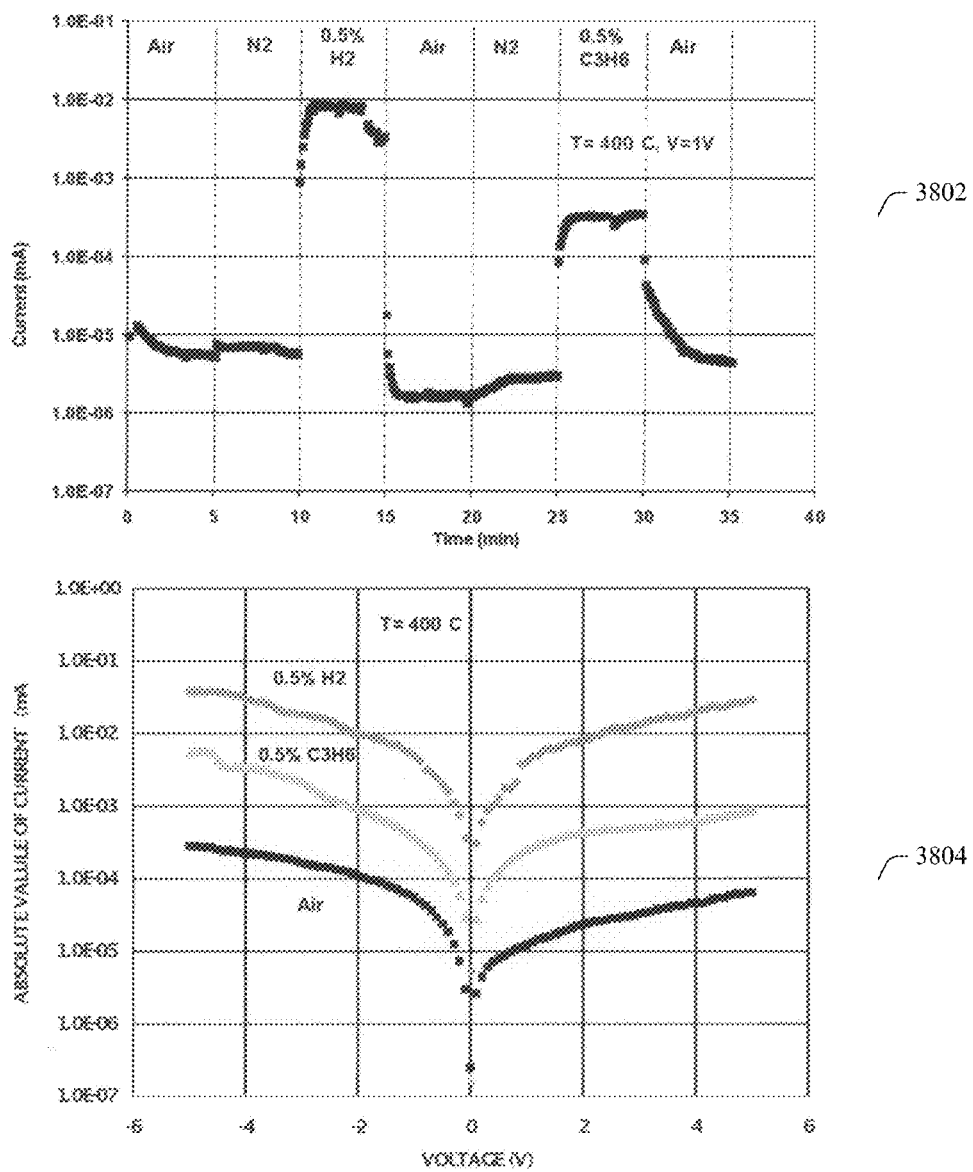
FIG. 38 shows the current response against time and voltage of a $SnO_2$ sensor to various gases at a temperature of 400° C.

FIG. 38 shows the current response against time and voltage of a $SnO_2$ sensor to various gases at a temperature of 400° C. Graph 3802 shows the current against time response at 1V. A strong response of the $SnO_2$ sensor to hydrogen and propylene can be seen in graph 3802, with a current response that was two and three orders of magnitude larger than the air baseline upon hydrogen/nitrogen and propylene/nitrogen exposure, respectively. Graph 3802 shows that the sensor established a baseline in air with minimal response to nitrogen, and a strong increase in current upon exposure to hydrogen/nitrogen (consistent with n-type response). After the exposure to hydrogen/nitrogen, there was a small change in the baseline, followed by a minimal response to nitrogen, and a strong increase in current upon exposure to propylene/nitrogen, but notably smaller than that for hydrogen/nitrogen. Comparing FIG. 38 with FIG. 37 shows a significant contrast between the response of the $SnO_2$ and MWCNT sensors, as may be expected given the chemical differences between carbon and oxide materials.

Additionally, some experiments examined the behavior of $SnO_2$ nanowires prepared via electrophoresis on Pt electrodes, but without a top layer to form buried electrical contacts between the nanostructure and the electrodes. Such a sensor showed a diminished response at 400° C. compared to lower temperatures, which may be due to a degradation of electrical contacts. In contrast, the results of FIG. 38 show a continued strong response at 400° C., and comparison with data at 300° C. for the same sensor (not shown) indicates sensor response did not decrease as the temperature increased from 300° C. to 400° C., indicating that burying the contacts can improve sensor performance.

Graph 3804 shows the current against voltage (I-V) curves associated with the $SnO_2$ sensor used to obtain the results of FIG. 38. These curves demonstrate the continuity of the sensor electrical contact and significant differences between the I-V curves for air, hydrogen/nitrogen, and propylene/nitrogen. The absolute value of the current against voltage was plotted from −5V to 5V. The current for hydrogen/nitrogen was the largest, with nearly 2 orders of magnitude of response compared with a near order of magnitude response to propylene/nitrogen above the air baseline consistent across the voltage range. The I-V curves also show an asymmetry between the positive and negative voltages, with large current at negative bias. Asymmetry in I-V curves were also noted for nanostructures with unburied contacts.

Discussion of Results

As explained above, nanostructures forms of metal oxide semiconducting materials provide a variety of benefits over other structures, for reasons including size, surface area relative to depletion depth, stability, and sensitivity. However, very different nanostructures exist, either single-crystal or polycrystalline, each with their own considerations, as discussed above: the unknown defect density of single-crystal nanowires, and the variable response of junction potentials of the polycrystalline nanofiber.

These different forms of one-dimensional morphology sensing elements can require very different fabrication and integration processes for commercial sensing devices. Electrospinning can offer direct deposition, composition control, and potentially a very reactive surface reflecting the polycrystallinity of the material. Precursors can be expensive, and calcination will involve the entire substrate. TEC-synthesized nanowires can offer uniform crystal surfaces, resistance to sintering, and their synthesis may be done apart from the substrate. However, with higher crystalline perfection, potentially fewer chemisorption sites may exist, resulting in lower sensitivity and dynamic range. Electrospun nanofibers can offer a dry fabrication process on the sensor chip apart from the sol-gel plus polymer precursor solution. TEC nanowires can require liquid phase deposition as a washcoat and perhaps an additional binder such as a sol-gel solution. A consideration is that the substrate temperature can elevates, as with TEC, unless collection with subsequent dispersal and deposition is applied. Also, while individual particles may be singlecrystalline, the film will necessarily be polycrystalline. Thus, fewer chemisorption sites and susceptibility to sintering may result. Controlled oxidation can offer a synthesis route for nanowires of materials not readily accessible via a TEC approach, for example, refractory oxides such as $Fe_2O_3$, $WO_3$, $TiO_2$, $MoO_3$, etc. However, the method can be extremely sensitive to both the nascent metal grain structure and process conditions, in particular, the oxidizer concentration. Potential complications can arise in both harvesting and purification, given the adhesion strength of the nanowires to the supporting (oxidized) metal substrate.

As seen in the above results, nascent materials without catalyst exhibited divergent responses. The TEC-produced nanowire response was very low, even at the operating temperature of 200° C. In contrast, the nanofiber response was high (~500), suggesting that junction potentials are superior to a continuous surface depletion layer as a transduction mechanism for chemisorption. Using a catalyst deposited upon the surface in the form of nanoparticles, yielded dramatic gains in sensitivity for both nanostructured one-dimensional forms. For the nanowire materials, the response magnitude and response rate uniformly increased with increasing operating temperature. Such changes can be interpreted in terms of accelerated surface diffusional processes, yielding greater access to chemisorbed oxygen species and faster dissociative chemisorption, respectively.

Conversely, the normalized response of the nanofibers with catalyst decreased with increasing temperature, being the highest at ambient, 23° C. This decreasing response can be interpreted as reflecting the open porosity created by the polycrystalline structure of the nanofiber in conjunction with its small radius. Adsorbates can access all exposed surfaces already at ambient temperature. Accessible surface area, as nominally governed by diffusional processes, did not increase with increasing temperature. Rather, with increasing temperature, chemisorbed oxygen species may be lost (desorbed) and/or transformed into more strongly chemisorbed species, thereby accounting for the decreasing response with increasing temperature. Nevertheless, the temporal response of the electrospun nanofibers improved with operating temperature, reflecting faster dissociation of adsorbing hydrogen. Regardless of operating temperature, sensitivity of the nanofibers was a factor of 10 to 100 greater than that of nanowires with the same catalyst for the same test condition. Based on these differing results, nanostructure can be critical to governing the reactivity, as measured by electrical resistance of $SnO_2$ towards reducing gases. With regards to the sensitivity of the different nascent nanostructures, the electrospun nanofibers provided more favorable results.

For both morphological forms, catalyst nanoparticles were necessary to produce a high response amplitude, but their effect was strongly moderated by the metal oxide nanostructure. Significantly, the Pd catalyst enabled operation at ambient temperature. In concert with Pd catalyst, the polycrystalline nanostructure of the electrospinning-produced nanofibers for gas sensing was superior to the singlecrystal TEC-produced nanowires in the experimental results discussed above for Pd as the catalyst. As indicated above, testing of $SnO_2$ nanowires with Pt as catalyst has shown either comparable or superior responses compared to the nanofibers with Pd catalyst, suggesting that the nanostructure of the metal oxide couples strongly.

Comparisons of polycrystalline and single crystalline materials (e.g., comparisons between materials produced via electrospinning and CVD or TEC) in experimental results as discussed above demonstrate that grain structure (i.e., grain boundaries) control material sensing properties. For one-dimensional nanostructures (e.g., the nanowires and nanofibers used to obtain the experimental results above), the grain structure is equivalent to the grain size. Two and three dimensional nanostructures, such as in thin or thick films, can be used for liquid or gas sensing and can be made from one dimensional elements.

Because of the effect of grain structure on material sensing properties, control over grain structure can be highly desirable. Control over grain structure through synthesis can be difficult to control due to the size or length scale involved, and can lead to undesirable results.

However, in aspects of the present innovation, other methods can be used to control the grain structure by applying a sufficient force to larger grains in order to form grains of a desired size. Various methods can be employed to apply such a force. For example, this force can be generated by light, by sound, hydrodynamically, by mechanical impact, or thermally. Specific examples include sonication (e.g., via horn or bath ultrasound), mechanical grinding, impaction (e.g., as assisted by air or liquid processes), light-induced breakup, rapid thermal shock, or other physical processes.

By controlling grain structure as explained above, material properties can be selected for. Additionally, this can be employed in conjunction with other aspects of the subject innovation, for example, it can optionally be combined with selecting varying lengths of nanostructures based on the response to AC frequency, in order to facilitate selective manipulation of nanostructures at one or more points on the pattern of bottom electrodes. Additionally, because two and three dimensional nanostructures can be composed of one dimensional nanostructure elements, the properties of two and three dimensional nanostructures (e.g., thin or thick films) can be controlled via the grain size of the one dimensional elements they are composed of.

Systems and methods of the subject innovation allow for microfabrication of devices incorporating nanostructures. One potential use is microfabrication of nanostructure sensors, which could have applications include emissions monitoring, engine monitoring, security, fire detection, EVA applications, personal health monitoring, and environmental monitoring. The resulting sensors can be used in applications where presently micro sensors are used, but the use of nanostructured materials can improve sensor system capabilities.

Additionally, these systems and methods can be applied in a wide range of contexts beyond sensors. For example, dispersing metal oxide semiconductors using standard photolithographic techniques can allow for ease of integration of the nanostructure into thin films for conductive coatings requiring electrical connections. Another example is to potentially replace fluor-doped $SnO_2$ (FTO) used as anode backing in bulk heterojunction solar cells. Moreover, the systems and methods described herein are compatible with low temperature, thin film supports, such as flexible backings for electronics.

Additionally, numerous other applications exist, as the systems and methods described herein can be used to incorporate nanostructures into microdevices in a reliable and reproducible manner irrespective of the ultimate application. Thus, systems and methods in accordance with the subject innovation can be employed in fabricating microdevices incorporating nanostructures for substantially any application in which such microdevices could be used. Additionally, while specific examples and uses of the techniques and systems described herein have been noted, it is to be understood that alternative embodiments exist. These alternatives are to be included within the scope of this specification and claims appended hereto.

In other words, what has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of creating a microstructure incorporating nanotechnology, comprising:
   forming a pattern of bottom electrodes on a substrate of the microstructure, wherein one or more regions of the pattern of bottom electrodes has a relatively high electric field gradient;
   applying a suspension of nanostructures in a photoresist to the microstructure;
   creating at least one aligned nanostructure via performing dielectrophoresis on the suspension of nanostructures in the photoresist;
   exposing the photoresist; and
   creating a top electrode deposition that covers both the nanostructure and the pattern of bottom electrodes.

2. The method of claim 1, wherein the one or more regions form a pattern with a sawtoothed design.

3. The method of claim 1, further comprising forming a pattern of top electrodes that buries one or more contacts of the at least one aligned nanostructure.

4. The method of claim 1, wherein the nanostructures comprise at least one of a metal oxide, a chemically reactive metal, an alloy of palladium, platinum, gold or silver, or a carbon-based material.

5. The method of claim 1, wherein the electrodes comprise at least one of platinum, gold, palladium, copper, rhodium, silver, titanium, or tungsten, or an alloy thereof.

6. The method of claim 1, wherein the photoresist is used for further processing of the microstructure.

7. The method of claim 1, wherein the substrate comprises at least one of silicon, silicon carbide, silicon dioxide, silicon on insulator, gallium nitride, aluminum oxide, quartz, sapphire, germanium, gallium arsenide, an alloy of silicon and germanium, indium phosphide, or an insulator coated metal.

* * * * *